(12) United States Patent
Hay et al.

(10) Patent No.: US 10,966,414 B2
(45) Date of Patent: Apr. 6, 2021

(54) POPULATION CONTROL USING ENGINEERED TRANSLOCATIONS

(71) Applicant: California Institute of Technology, Pasadena, CA (US)

(72) Inventors: Bruce A. Hay, Encino, CA (US); Omar S. Akbari, Pasadena, CA (US); Anna B. Buchman, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 191 days.

(21) Appl. No.: 15/164,452

(22) Filed: May 25, 2016

(65) Prior Publication Data

US 2016/0345556 A1 Dec. 1, 2016

Related U.S. Application Data

(60) Provisional application No. 62/166,281, filed on May 26, 2015.

(51) Int. Cl.
*A01K 67/033* (2006.01)
*C12N 15/85* (2006.01)

(52) U.S. Cl.
CPC ...... *A01K 67/0339* (2013.01); *C12N 15/8509* (2013.01); *A01K 2217/15* (2013.01); *A01K 2227/706* (2013.01); *A01K 2267/02* (2013.01)

(58) Field of Classification Search
CPC .................................................. A01K 67/0339
See application file for complete search history.

(56) References Cited

U.S. PATENT DOCUMENTS

| 5,753,434 A | 5/1998 | Ryner et al. |
| 2003/0213005 A1 | 11/2003 | Alphey et al. |
| 2007/0056051 A1 | 3/2007 | Alphey |
| 2009/0183269 A1 | 7/2009 | Alphey |
| 2013/0298266 A1 | 11/2013 | Alphey et al. |
| 2014/0223591 A1 | 8/2014 | Hay et al. |
| 2014/0283155 A1 | 9/2014 | Akbari et al. |
| 2015/0237838 A1 | 8/2015 | Hay et al. |
| 2016/0060358 A1 | 3/2016 | Hay |
| 2016/0345556 A1 | 5/2016 | Hay et al. |
| 2018/0320164 A1 | 11/2018 | Hay et al. |

FOREIGN PATENT DOCUMENTS

| JP | 2544120 B2 | 10/1996 |
| KR | 10-2017-0041640 A | 4/2017 |
| WO | WO 1999/065520 A1 | 12/1999 |
| WO | WO 2008/009960 A2 | 1/2008 |
| WO | WO 2010/049777 A1 | 5/2010 |
| WO | WO 2012/143401 A1 | 10/2012 |
| WO | WO 2014/120975 A8 | 8/2014 |
| WO | WO 2016/049230 A1 | 3/2016 |
| WO | WO 2018/204722 A1 | 11/2018 |

OTHER PUBLICATIONS

Akbari, O.S. et al., A synthetic gene drive system for local, reversible modification and suppression of insect populations, Curr. Biol., vol. 23 No. 8, pp. 671-677. 2013.

Akbari, O.S. et al., Novel synthetic Medea selfish genetic elements drive population replacement in *Drosophila*; a theoretical exploration of Medea-dependent population suppression, ACS Synth Biol. vol. 3 No. 12, pp. 915-928; 2014.

Alphey, L. et al., Malaria Control with Genetically Manipulated Insect, Nature vol. 415, 702; 2002.

Altrock, P. M. et al., Stability properties of underdominance in finite subdivided populations, PLoS Comput. Biol., vol. 7 No. 11, e1002260; 2011.

Altrock, P. M. et al., Using underdominance to bi-stably transform local populations, J Theor Biol, vol. 267 No. 1, pp. 62-75; 2010.

Arndt, K. M. et al., Helix-stabilized Fv (hsFv) antibody fragments: substituting the constant domains of a Fab fragment for a heterodimeric coiled-coil domain, J Mol Biol, vol. 312 No. 1, pp. 221-228.; 2001.

Asman, S. M. et al., Field studies of genetic control systems for mosquitoes, Annu Rev Entomol., vol. 26 No. 1, pp. 289-318; 1981.

Baker, R.H., Chromosome Rearrangements in the Control of Mosquitos, Prev Vet Med 2, pp. 529-540; 1984.

Bergmann, A. et al., The *Drosophila* gene hid is a direct molecular target of Ras-dependent survival signaling, Cell, vol. 95 No. 3, pp. 331-341; 1998.

Beumer, K. J. et al., "Induced chromosomal exchange directs the segregation of recombinant chromatids in mitosis of *Drosophila*. Genetics," Genetics, vol. 150 No. 1, pp. 173-188; (1998).

Bier V.M.G.A.E. et al., The mutagenic chain reaction: A method for converting heterozygous to homozygous mutations, Science, vol. 348 No. 6233, pp. 442-444; 2015.

Billeter, J. C. et al., Specialized cells tag sexual and species identity in *Drosophila melanogaster*, Nature, vol. 461 No. 7266, pp. 987-991; 2009.

Boete C. et al., A theoretical approach to predicting the success of genetic manipulation of malaria mosquitoes in malaria control, Malar J, vol. 1 No. 3; 2002.

Boete C. et al., Evolutionary ideas about genetically manipulated mosquitoes and malaria control, Trends Parasitol, vol. 19 No. 1, pp. 32-38; 2003.

Bohannon J., Food aid. Zambia rejects GM corn on scientists' advice, Science, vol. 298 No. 5596, pp. 1153-1154; 2002.

Borycz J. et al., ABC transporter mutants white, brown and scarlet have altered contents and distribution of biogenic amines in the brain, J Exp Biol, vol. 211 No. 21, pp. 3454-3466; 2008.

Braig, H. R. et al., The spread of genetic constructs in natural insect populations. In D. K. Letourneau & B. E. Burrows (Eds.) Genetically Engineered Organisms: Assessing Environmental and Human Health Effects (pp. 251-314). Cleveland, OH/Boca Raton, FL: CRC Press; 2002.

(Continued)

*Primary Examiner* — Thaian N. Ton
*Assistant Examiner* — David A. Montanari
(74) *Attorney, Agent, or Firm* — Knobbe, Martens, Olson & Bear LLP

(57) ABSTRACT

Embodiments provided herein relate to systems for synthetically-engineered reciprocal chromosomal translocation for gene insertion into a population of organisms such as insects.

12 Claims, 32 Drawing Sheets

Specification includes a Sequence Listing.

(56) References Cited

OTHER PUBLICATIONS

Carvajal-Vallejos P. et al., Unprecedented rates and efficiencies revealed for new natural split inteins from metagenomic sources, J Biol Chem, vol. 287 No. 34, pp. 28686-28696; 2012.

Carvalho D.O. et al., Two step male release strategy using transgenic mosquito lines to control transmission of vector-borne diseases, Acta Trop 132S, S170-S177; 2014.

Chen C.H. et al., A synthetic maternal-effect selfish genetic element drives population replacement in *Drosophila*, Science, vol. 316 No. 5824, pp. 597-600; 2007.

Cheriyan, M. et al., Faster protein splicing with the Nostoc punctiforme DnaE intein using non-native extein residues, J Biol Chem, vol. 288 No. 9, pp. 6202-6211; 2013.

Cook, R. K. et al., The generation of chromosomal deletions to provide extensive coverage and subdivision of the *Drosophila melanogaster* genome, Genome Biol, vol. 13 No. 3, R21; 2012.

Corby-Harris, V. et al., Activation of Akt signaling reduces the prevalence and intensity of malaria parasite infection and lifespan in *Anopheles stephensi* mosquitoes, PLoS Pathog, vol. 6 No. 7, e1001003; 2010.

Crompton, P. D. et al., Malaria immunity in man and mosquito: insights into unsolved mysteries of a deadly infectious disease, Annu Rev of Immunol, vol. 32 No. 1, pp. 157-187; 2014.

Curtis C.F. et al., "Computer simulation of the use of double translocations for pest control," Genetics, vol. 69 No. 1, 97-113; 1971.

Curtis, C. F., Possible use of translocations to fix desirable genes in insect pest populations, Nature, vol. 218 No. 5139, pp. 368-369; 1968.

Dantuma N.P. et al., Short-lived green fluorescent proteins for quantifying ubiquitin/proteasome-dependent proteolysis in living cells, Nat Biotechnol., vol. 18 No. 5, pp. 538-543; 2000.

Davis S. et al., Engineered underdominance allows efficient and economical introgression of traits into pest populations, J Theor Biol., vol. 212 No. 1, pp. 83-98; 2010.

De Jesus C. et al., Use of genetic modified mosquitoes to fight dengue in Brazil, International Journal of Research in Pharmaceutical and Nano Sciences, vol. 2 No. 6, pp. 811-816; 2000.

De La Rocque S. et al., A review of trends in the distribution of vector-borne diseases: is international trade contributing to their spread? Rev Sci Tech, vol. 30 No. 1, pp. 119-130; 2011.

De Lara Capurro M. et al., Virus-expressed, recombinant single-chain antibody blocks sporozoite infection of salivary glands in Plasmodium gallinaceum-infected Aedes aegypti, Am J Trop Med Hyg., vol. 62 No. 4, pp. 427-433; 2000.

De N. et al., Highly complementary target RNAs promote release of guide RNAs from human Argonaute2, Mol Cell, vol. 50 No. 3, pp. 344-355; 2013.

Deredec A et al., The population genetics of using homing endonuclease genes in vector and pest management, Genetics, vol. 179 No. 4, pp. 2013-2026; 2008.

Dhar T. et al., Modification of transmembrane and GPI-anchored proteins on living cells by efficient protein trans-splicing using the Npu DnaE intein, Chem Commun (Camb), vol. 47 No. 11, pp. 3063-3065; 2011.

Egli D et al., An efficient method to generate chromosomal rearrangements by targeted DNA double-strand breaks in *Drosophila melanogaster*, Genome Res., vol. 14 No. 7, pp. 1382-1393; 2004.

Enayati A. et al., Malaria management: past, present, and future, Annu Rev Entomol., vol. 55, pp. 569-591; 2010.

Engler, C. et al., A one pot, one step, precision cloning method with high throughput capability, PLoS one, vol. 3 No. 11, e3647; 2008.

Engler, C. et al., Golden gate shuffling: a one-pot DNA shuffling method based on type IIs restriction enzymes, PLoS one, vol. 4 No. 5, e5553; 2009.

Eppstein, M. J., Payne, J. L., & Goodnight, C. J. (2009). Underdominance, multiscale interactions, and self-organizing barriers to gene flow. Journal of Artificial Evolution and Applications 5, 1-13.

Esvelt, K.M. et al., Concerning RNA-guided gene drives for the alteration of wild populations, Elife, e03401; 2014.

Fields, S. et al., A novel genetic system to detect protein-protein interactions, Nature, vol. 340 No. 6230, pp. 245-246; 1989.

Filipowicz, W. et al., Post-transcriptional gene silencing by siRNAs and miRNAs, Curr Opin Struct Biol., vol. 15 No. 3, pp. 331-341; 2005.

Forster, A. et al., Chromosomal translocation engineering to recapitulate primary events of human cancer, Cold Spring Harb Symp Quant Biol, vol. 70, pp. 275-282; 2005.

Foster, G.et al., Chromosome rearrangements for the control of insect pests, Science, vol. 176 No. 4037, pp. 875-880; 1972.

Franz, A. W. et al., Engineering RNA interference-based resistance to dengue virus type 2 in genetically modified Aedes aegypti, Proc Natl Acad Sci U S A, vol. 103 No. 11, pp. 4198-4203; 2006.

Fu, G. et al., Female-specific flightless phenotype for mosquito control, Proc Natl Acad Sci USA, vol. 107 No. 10, pp. 4550-4554; 2010.

Gallup, J.L. et al., The economic burden of malaria, Am J Trop Med Hyg, vol. 64 No. 1-2 Suppl, pp. 85-96; 2001.

Gdula, D.A. et al., Genetic and molecular analysis of the gypsy chromatin insulator of *Drosophila*, Proc Natl Acad Sci USA, vol. 93 No. 18, pp. 9378-9383; 1996.

Gibson, D. G. et al., Enzymatic assembly of DNA molecules up to several hundred kilobases, Nat Methods, vol. 6 No. 5, pp. 343-345; 2009.

Githeko, A. K. et al., Climate change and vector-borne diseases: a regional analysis, Bulletin of the World Health Organization, vol. 78, No. 9, pp. 1136-1147, 2000.

Gong, W. J. et al., Ends-out, or replacement, gene targeting in *Drosophila*, Proceedings of the National Academy of Sciences, vol. 100, No. 5, pp. 2556-2561, 2003.

Gould, F. et al., Population genetics of autocidal control and strain replacement, Annu Rev Entomol, vol. 49, pp. 193-217, 2004.

Gould, F. et al., A Killer-Rescue system for selflimiting gene drive of anti-pathogen constructs, Proceedings of the Royal Society B: Biological Sciences, vol. 275, No. 1653, pp. 2823-2829, 2008.

Gould, F. et al., Genetic strategies for controlling mosquitoborne diseases: engineered genes that block the transmission of malaria and dengue can hitch a ride on selfish DNA and spread into wild populations, American scientist, pp. 238-246, 2006.

Groth, A. C. et al., Construction of transgenic *Drosophila* by using the site-specific integrase from phage φC31, Genetics, vol. 166, No. 4, pp. 1775-1782, 2004.

Gubler, D. J. et al., Climate variability and change in the United States: potential impacts on vector- and rodent-borne diseases, Environmental health perspectives, vol. 109, Suppl 2, pp. 223, 2001.

Gubler, D. J., Resurgent vector-borne diseases as a global health problem, Emerging infectious diseases, vol. 4, No. 3, pp. 442, 1998.

Gutierrez, E. et al., Specialized hepatocytelike cells regulate *Drosophila* lipid metabolism, Nature, vol. 445, No. 7125, pp. 275-280, 2007.

Han, Z. et al., Hand is a direct target of Tinman and GATA factors during *Drosophila* cardiogenesis and hematopoiesis, Development, vol. 132, No. 15, pp. 3525-3536, 2005.

Harris, A. F. et al., Field performance of engineered male mosquitoes, Nature biotechnology, vol. 29, No. 11, pp. 1034-1037, 2011.

Harris, A. F. et al., Successful suppression of a field mosquito population by sustained release of engineered male mosquitoes, Nature biotechnology, vol. 30, No. 9, pp. 828-830, 2012.

Hartl, D.L. et al., Principles of Population Genetics, Sunderland, MA: Sinauer Associates, Inc., 1997.

Hay, B. A. et al., Engineering the genomes of wild insect populations: challenges, and opportunities provided by synthetic Medea selfish genetic elements, J Insect Physiol, vol. 56, No. 10, pp. 1402-1413, 2010.

Hoffmann, A. A. et al., Successful establishment of Wolbachia in Aedes populations to suppress dengue transmission, Nature, vol. 476, No. 7361, pp. 454-457, 2011.

Ito, J. et al. Transgenic anopheline mosquitoes impaired in transmission of a malaria parasite, Nature, vol. 417, No. 6887, pp. 452-455, 2002.

Jacobs-Lorena, M. Genetic approached for malaria control. In Bogers, R.J. (ed.), Bridging Laboratory and Field Research for

(56) References Cited

OTHER PUBLICATIONS

Genetic Control of Disease Vectors, pp. 52-65, Retrieved from http://library.wur.nl/frontis/, 2004.
James, A. A, Gene drive systems in mosquitoes: rules of the road, Trends Parasitol, vol. 21, No. 2, pp. 64-67, 2005.
Jansen V.A. et al., Stochastic spread of Wolbachia, Proc Biol Sci, vol. 275 No. 1652, pp. 2769-2776; 2008.
Kaiser, P.E. et al., Radiation induced reciprocal translocations and inversions in Anopheles albimanus, Can J Genet Cytol, vol. 24 No. 2, pp. 177-188; 1982.
Kim, W. et al., Ectopic expression of a cecropin transgene in the human malaria vector mosquito *Anopheles gambiae* (Diptera: Culicidae): effects on susceptibility to Plasmodium, Journal of medical entomology, vol. 41, No. 3, pp. 447-455, 2004.
Knols, B. G. et al., Transgenic mosquitoes and the fight against malaria: managing technology push in a turbulent GMO world, Am J Trop Med Hyg., vol. 77, 6 Suppl, pp. 232-242, 2007.
Krafsur, E. S. et al., Sterile insect technique for suppressing and eradicating insect populations: 55 years and counting, J. Agr. Entomol., vol. 15, 303-317, 1998.
Krstic, D. et al., Influence of the White Locus on the Courtship Behavior of *Drosophila* Males, PLoS one, vol. 8, No. 10, e77904, 2013.
Kwit, C. et al, Transgene introgression in crop relatives: molecular evidence and mitigation strategies. Trends Biotechnol, vol. 29, No. 6, pp. 284-293, 2011.
Kyrchanova, O., et al, Orientation-dependent interaction between *Drosophila* insulators is a property of this class of regulatory elements, Nucleic acids research, vol. 36, No. 22, pp. 7019-7028, 2008.
Lambrechts, L. et al., Can transgenic mosquitoes afford the fitness cost? Trends Parasitol, vol. 24 No. 1, pp. 4-7; 2008.
Lemon, S. M. et al., Vector-Borne Diseases: Understanding the Environmental, Human Health, and Ecological Connections, Workshop Summary (Forum on Microbial Threats), National Academies Press, 2008.
Lin, H. et al., Cellular toxicity induced by SRFmediated transcriptional squelching, Toxicological sciences, vol. 96, No. 1, pp. 83-91, 2007.
Lo, P. C. et al., A role for the COUP-TF-related gene seven-up in the diversification of cardioblast identities in the dorsal vessel of *Drosophila*, Mech Dev, vol. 104, pp. 49-60, 2001.
Lockless, S. W. et al., Traceless protein splicing utilizing evolved split inteins, Proc Natl Acad Sci U S A, vol. 106, No. 27, pp. 10999-11004, 2009.
Luan, H. et al., Refined spatial manipulation of neuronal function by combinatorial restriction of transgene expression, Neuron, vol. 52, No. 3, pp. 425-436, 2006.
Lyon, M. F. et al., Mutagenic effects of repeated small radiation doses to mouse spermatogonia I. Specific-locus mutation rates, Mutation Research/Fundamental and Molecular Mechanisms of Mutagenesis, vol. 15, No. 2, pp. 185-190, 1972.
Magori, K. et al., Genetically engineered underdominance for manipulation of pest populations: a deterministic model. Genetics, vol. 172, No. 4, pp. 2613-2620, 2006.
Marris, E., Transgenic fish go large, Nature, vol. 467, No. 7313, pp. 259, 2010.
Marshall, J. M. et al., Confinement of gene drive systems to local populations: a comparative analysis, J Theor Biol, vol. 294, pp. 153-171, 2012.
Marshall, J. M. et al., Inverse Medea as a novel gene drive system for local population replacement: a theoretical analysis, J Hered, vol. 102, No. 3, pp. 336-341, 2011.
Marshall, J. M. et al., Perspectives of people in Mali toward genetically-modified mosquitoes for malaria control, Malar J, vol. 9, No. 128, 2010a.
Marshall, J. M. et al., Towards a quantitative assessment of public attitudes to transgenic mosquitoes: Questions based on a qualitative survey in Mali, Asia Pacific J. Mol. Biol. Biotechnol, vol. 18, pp. 251-273, 2010b.
Marshall, J. M., The Cartagena Protocol and genetically modified mosquitoes, Nat. Biotechnol., vol. 28, No. 9, pp. 896-897, 2010.
Marshall, J. M., The effect of gene drive on containment of transgenic mosquitoes, J. of Theor. Biol., vol. 258, No. 2, pp. 250-265, 2009.
Marshall, J.M. et al., General principles of single-construct chromosomal gene drive, Evolution; vol. 66 No. 7, pp. 2150-2166; 2012b.
Marshall, J.M. et al., Semele: a killer-male, rescue-female system for suppression and replacement of insect disease vector populations, Genetics, vol. 187 No. 2, pp. 535-551; 2011.
Marygold, S. J. et al., The ribosomal protein genes and Minute loci of *Drosophila melanogaster*, Genome Biol, vol. 8, No. 10, R216, 2007.
Matzen, K.J. Engineering of Dengue virus refractoriness in Aedes aegypti and development of an underdominant gene drive system (Doctoral dissertation), California Institute of Technology, Pasadena, CA, 2012.
McManus, M. T. et al., Gene silencing using micro-RNA designed hairpins, RNA, vol. 8, No. 6, 842-850, 2002.
Miller, L. H. et al., Perspective on malaria eradication: is eradication possible without modifying the mosquito? Journal of Infectious Diseases, vol. 200, No. 11, pp. 1644-1645, 2009.
Miller, T. A., Let high-tech genetically modified insects counter dengue, BioScience, vol. 61, No. 8, pp. 586-587, 2011.
Moreira, L. A. et al., Bee venom phospholipase inhibits malaria parasite development in transgenic mosquitoes, J Biol Chem, vol. 277, No. 43, pp. 40839-40843, 2002.
Moreno, E., Design and construction of "synthetic species," PLoS One, vol. 7, No. 7, e39054, 2012.
Morrison, N. I. et al., Genetic improvements to the sterile insect technique for agricultural pests, Asia-Pacific Journal of Molecular Biology and Biotechnology, vol. 18, No. 2, pp. 275-295, 2010.
Mumford, J. D. Science, regulation, and precedent for genetically modified insects, PLoS neglected tropical diseases, vol. 6, No. 1, e1504, 2012.
Murray, C. J. et al., Global malaria mortality between 1980 and 2010: a systematic analysis, The Lancet, vol. 379, No. 9814, pp. 413-431, 2012.
Nath, R., Generation and characterisation of plant produced recombinant antibodies specific to LHRH for treatment of sex hormone dependent diseases. (MS thesis), Fachhochschule Aachen, Aachen, Germany, 2003.
Ndiath, M. O., et al., Resistance to DDT and pyrethroids and increased kdr mutation frequency in An. gambiae after the implementation of permethrin-treated nets in Senegal, PloS one, vol. 7, No. 2, e31943, 2012.
Neely, G. G. et al., A Global In Vivo *Drosophila* RNAi Screen Identifies NOT3 as a Conserved Regulator of Heart Function, Cell, vol. 141, No. 1, pp. 142-153, 2010.
Nern, A. et al., Multiple new site-specific recombinases for use in manipulating animal genomes, Proceedings of the National Academy of Sciences, vol. 108, No. 34, pp. 14198-14203, 2011.
Ni, J. Q. et al., A genome-scale shRNA resource for transgenic RNAi in *Drosophila*, Nat Methods, vol. 8, No. 5, pp. 405-407, 2011.
Nicholson, G.M. et al., Fighting the global pest problem: preface to the special Toxicon issue on insecticidal toxins and their potential for insect pest control, Toxicon, vol. 49 No. 4, pp. 413-422; 2007.
Oye, K.A. et al., Biotechnology. Regulating gene drives, Science vol. 345 No. 6197, pp. 626-628; 2014.
Pardo, R. et al., The role of means and goals in technology acceptance, A differentiated landscape of public perceptions of pharming, EMBO Rep, vol. 10, No. 10, pp. 1069-1075, 2009.
Parvy, J. P. et al, *Drosophila melanogaster* Acetyl-CoA-Carboxylase Sustains a Fatty Acid-Dependent Remote Signal to Waterproof the Respiratory System, PLoS genetics, vol. 8, No. 8, e1002925, 2012.
Perrimon, N. et al., In vivo RNAi: today and tomorrow, Cold Spring Harbor perspectives in biology, vol. 2, No. 8, a003640, 2010.
Pfeiffer, B. D. et al, Refinement of tools for targeted gene expression in *Drosophila*, Genetics, vol. 186, No. 2, pp. 735-755, 2010.

(56) References Cited

OTHER PUBLICATIONS

Pfeiffer, B. D. et al., Using translational enhancers to increase transgene expression in *Drosophila*. Proc Natl Acad Sci U S A, vol. 109, No. 17, pp. 6626-6631, 2012.
Ran, F. A. et al., Genome engineering using the CRISPR-Cas9 system, Nature protocols, vol. 8, No. 11, pp. 2281-2308, 2013.
Randolph, S.E. et al., "The arrival, establishment and spread of exotic diseases: patterns and predictions," Nat Rev Microbiol., vol. 8 No. 5, pp. 361-371; (2010).
Riehle, M. M. et al., Anopheles gambiae APL1 is a family of variable LRR proteins required for Rel1-mediated protection from the malaria parasite, *Plasmodium berghei*, PLoS One, vol. 3, No. 11, e3672, 2008.
Ringrose, L., et al., Quantitative comparison of DNA looping in vitro and in vivo: chromatin increases effective DNA flexibility at short distances, The EMBO Journal, vol. 18, No. 23, 6630-6641, 1999.
Robinson A.S., A reassessment of the use of chromosome inversions for insect control, Journal of Heredity, vol. 66, pp. 35-37, 1975.
Robinson, A. S. et al., Insect transgenesis and its potential role in agriculture and human health, Insect biochemistry and molecular biology, vol. 34, No. 2, pp. 113-120, 2004.
Robinson, A.S. et al., Controlled Crosses and Cage Experiments with a Translocation in *Drosophila*, Genetica, vol. 44, pp. 591-601; 1973.
Robinson, A.S., Progress in the use of chromosomal translocations for the control of insect pests. Biological Reviews, vol. 51, No. 1, pp. 1-24, 1976.
Rong, Y. S. et al., The homologous chromosome is an effective template for the repair of mitotic DNA double-strand breaks in *Drosophila*, Genetics, vol. 165, No. 4, pp. 1831-1842, 2003.
Rørth, P, Gal4 in the *Drosophila* female germline, Mechanisms of development, vol. 78, No. 1, pp. 113-118, 1998.
Schmid-Hempel, P., Evolutionary ecology of insect immune defenses, Annu Rev Entomol, vol. 50, pp. 529-551, 2005.
Schnutgen, F. et al., Adopting the good reFLEXes when generating conditional alterations in the mouse genome, Transgenic research, vol. 16, No. 4, pp. 405-413, 2007.
Schwartz, E. C. et al., Post-translational enzyme activation in an animal via optimized conditional protein splicing, Nat Chem Biol, vol. 3, No. 1., pp. 50-54, 2007.
Sellin, J. et al., Dynamics of heart differentiation, visualized utilizing heart enhancer elements of the *Drosophila melanogaster* bHLH transcription factor Hand, Gene Expr Patterns, vol. 6, No. 4, pp. 360-375, 2006.
Sherizen, D. et al., Meiotic recombination in *Drosophila* females depends on chromosome continuity between genetically defined boundaries, Genetics, vol. 169, No. 2, pp. 767-781, 2005.
Sinkins, S. P. et al., Gene drive systems for insect disease vectors, Nat Rev Genet, vol. 7, No. 6, pp. 427-435, 2006.
Spradling, A. C. et al., Transposition of cloned P elements into *Drosophila* germ line chromosomes. Science, vol. 218, No. 4570, pp. 341-347, 1982.
Szymczak, A. L. et al., Correction of multi-gene deficiency in vivo using a single 'self-cleaving' 2A peptide-based retroviral vector, Nature biotechnology, vol. 22, No. 5, pp. 589-594, 2004.
Tatem, A.J. et al., Global transport networks and infectious disease spread, Adv Parasitol, vol. 62, pp. 293-343; 2006.
Theilmann, D.A. et al., Molecular analysis of the trans-activating IE-2 gene of Orgyia pseudotsugata multicapsid nuclear polyhedrosis virus, Virology, vol. 187, No. 1, pp. 84-96, 1992.
Thomas, D. D. et al., Insect population control using a dominant, repressible, lethal genetic system. Science, vol. 287, No. 5462, pp. 2474-2476, 2000.
Thorpe, H. M. et al., Control of directionality in the sitespecific recombination system of the Streptomyces phage φC31, Molecular microbiology, vol. 38, No. 2, pp. 232-241, 2000.
Tolle, M. A., Mosquito-borne diseases. Current problems in pediatric and adolescent health care, vol. 39, No. 4, pp. 97-140, 2009.
Tripet, F. et al., Ecological immunology of mosquito-malaria interactions, Trends Parasitol vol. 24 No. 5-3, pp. 219-227; 2008.
Uemura, M. et al., Chromosomal manipulation by site-specific recombinases and fluorescent protein-based vectors, PloS one vol. 5 No. 3, e9846; 2010.
Van Dyke, D. L. et al., The frequency and mutation rate of balanced autosomal rearrangements in man estimated from prenatal genetic studies for advanced maternal age, American journal of human genetics, vol. 35, No. 2, pp. 301-308, 1983.
Walker, T. et al., The wMel Wolbachia strain blocks dengue and invades caged Aedes aegypti populations, Nature, vol. 476, No. 7361, pp. 450-453, 2011.
Wang, S. et al., Genetic approaches to interfere with malaria transmission by vector mosquitoes, Trends in biotechnology, vol. 31, No. 3, pp. 185-193, 2013.
Weber, E. et al, A modular cloning system for standardized assembly of multigene constructs, PLoS one, vol. 6, No. 2, e16765, 2011.
Whitten, M. J., Insect control by genetic manipulation of natural populations, Science, vol. 171, No. 3972, pp. 682-684, 1971.
Willis, N.L. et al., Reciprocal translocations and partial correlation of chromosomes in the stable fly, J Hered vol. 72 No. 2, pp. 104-106; 1981.
Windbichler, N. et al., A synthetic homing endonuclease-based gene drive system in the human malaria mosquito, Nature, vol. 473, No. 7346, pp. 212-215, 2011.
World Health Organization Global Burden of Disease Study, Retrieved Apr. 30, 2014, from who.int/evidence/bod, 2000.
Yu, Y. et al., Engineering chromosomal rearrangements in mice, Nat Rev Genet, vol. 2, No. 10, pp. 780-790, 2001.
Zettler, J. et al., The naturally split Npu DnaE intein exhibits an extraordinarily high rate in the protein trans-splicing reaction, FEBS Lett, vol. 583, No. 5, pp. 909-914, 2009.
Zhou, X. et al., Optimization of the Tet-On system for regulated gene expression through viral evolution, Gene therapy, vol. 13, No. 19, pp. 1382-1390, 2006.
Zhu, X. D. et al., Cleavage-dependent ligation by the FLP recombinase; characterization of a mutant flp protein with an alteration in a catalytic amino acid, Journal of Biological Chemistry, vol. 270, No. 39, pp. 23044-23054, 1995.
International Search Report and Written Opinion dated Apr. 25, 2014 in International Application No. PCT/US2014/013943.
International Search Report and Written Opinion dated Aug. 31, 2018 in International Application No. PCT/US2018/030990.
Notice of Allowance dated Feb. 13, 2017 in U.S. Appl. No. 14/206,011.
Office Action dated Apr. 9, 2015 in U.S. Appl. No. 14/206,011.
Office Action dated Sep. 21, 2015 in U.S. Appl. No. 14/206,011.
Office Action dated Feb. 4, 2016 in U.S. Appl. No. 14/631,171.
Office Action dated Apr. 7, 2016 in U.S. Appl. No. 14/206,011.
Office Action dated Sep. 2, 2016 in U.S. Appl. No. 14/206,011.
Office Action dated Jun. 2, 2016 in U.S. Appl. No. 14/170,118.
Office Action dated Aug. 18, 2016 in U.S. Appl. No. 14/631,171.
Office Action dated Dec. 28, 2016 in U.S. Appl. No. 14/170,118.
Office Action dated Apr. 6, 2017 in U.S. Appl. No. 14/631,171.
Office Action dated Sep. 21, 2017 in U.S. Appl. No. 14/837,941.
Office Action dated Jan. 26, 2018 in U.S. Appl. No. 14/837,941.
Office Action dated May 30, 2018 in U.S. Appl. No. 14/170,118.
Office Action dated Aug. 24, 2018 U.S. Appl. No. 14/837,941.
Office Action dated Oct. 19, 2018 in U.S. Appl. No. 14/170,118.
File History of U.S. Appl. No. 14/170,118.
File History of U.S. Appl. No. 14/206,011.
File History of U.S. Appl. No. 14/631,171.
File History of U.S. Appl. No. 14/837,941.
File History of U.S. Appl. No. 15/970,728.
Hu et al., A Large Gene Family in Fission Yeast Encodes Spore Killers That Subvert Mendel's Law, 2017.
Advisory Action dated Dec. 31, 2015 in U.S. Appl. No. 14/206,011.
Advisory Action dated Nov. 21, 2016 in U.S. Appl. No. 14/206,011.
Alphey, L. Genetic Control of Mosquitoes. Annu. Rev. Entomol, vol. 59, pp. 205-224, (2014).
Amin et al., "Organization of the *Drosophila melanogaster* hsp70 heat shock regulation unit," Molecular and Cellular Biology 7:1055-1062 (1987).

(56) References Cited

OTHER PUBLICATIONS

Ant et al., "Control of the olive fruit fly using genetics-enhanced sterile insect technique," BMC Biology 10:51 (2012).
Baker et al., "Genetic sexing for a mosquito sterile-male release", The Journal of Heredity, vol. 7, No. 2, pp. 216-218, 1981.
Beaghton, A., et al., Gene Drive through a Landscape: Reaction-Diffusion Models of Population Suppression and Elimination by a Sex Ratio Distorter, Theoretical Population Biology, vol. 108, pp. 51-69, (2016).
Beaghton, A., et al., Requirements for Driving Antipathogen Effector Genes into Populations of Disease Vectors by Homing, Genetics, vol. 205 (4), pp. 1587-1596, (2017).
Ben-David, E. et al., A Maternal-Effect Selfish Genetic Element in Caenorhabditis Elegans, Science 356 (6342), pp. 1051-1055, (2017).
Bischof, J. et al., An Optimized Transgenesis System for *Drosophila* Using Germ-Line-Specific phiC31 Integrases., Proceedings of the National Academy of Sciences of the United States of America 104 (9): 3312-17, (2007).
Boerjan et al., "Lignin biosynthesis," Annu Rev Plant Biol 54:519-546 (2003).
Bossin et al., "Somatic transformation efficiencies and expression patterns using the JcDNV and piggyBac transposon gene factors in insects," Insect Mol. Biol. 16:37-47 (2007).
Brelesfoard, C. et al., Wolbachia-based strategies to control insect pests and disease vectors. Asia Pac J Mol Biol Biotechnol vol. 17, pp. 55-63 (2009.
Brunel et al., "Cloning and sequencing of pseudomonas genes encoding vanillate demethylase," J. Bacteriol. 170:4924-4930 (1988).
Buchman, A., et al., Engineered Reciprocal Chromosome Translocations Drive High Threshold, Reversible Population Replacement in *Drosophila*, ACS Synthetic Biology, (2018).
Burt, A. et al., Homing endonuclease genes: the rise and fall and rise again of a selfish element. Curr. Opin. Genet. Dev. vol. 14, pp. 609-615 (2004).
Burt, A. et al Genetic Conflicts in Genomic Imprinting. Proceedings. Biological Sciences / The Royal Society 265 (1413): pp. 2393-2397, (1998).
Burt, A.., Site-Specific Selfish Genes as Tools for the Control and Genetic Engineering of Natural Populations, Proceedings. Biological Sciences / The Royal Society 270 (1518): pp. 921-928. (2003).
Bushland et al., "Eradication of Screw-Worms through Release of Sterilized Males", Science, vol. 122, No. 3163, pp. 287-288, 1955.
Carvalho et al., "Mass Production of Genetically Modified Aedes aegypti for Field Releases in Brazil", Journal of Visualized Experiments vol. 83, e3579, pp. 1-10, 2014.
Castillo, J. et al., Complex interaction between dengue virus replication and expression of miRNA-133a., BMC Infect. Dis. 16, (2016).
Champer, J et al., Novel CRISPR/Cas9 Gene Drive Constructs Reveal Insights into Mechanisms of Resistance Allele Formation and Drive Efficiency in Genetically Diverse Populations., PLoS Genetics, (2017).
Chan, Y. et al. Optimising Homing Endonuclease Gene Drive Performance in a Semi-Refractory Species: The *Drosophila melanogaster* Experience, (2013).
Chan, Yuk-Sang, Daniel A. Naujoks, David S. Huen, and Steven Russell. 2011. "Insect Population Control by Homing Endonuclease-Based Gene Drive: An Evaluation in *Drosophila melanogaster*." Genetics 188 (1): 33-44.
Clark, A. et al., "Evolution of Genes and Genomes on the *Drosophila* Phylogeny." Nature 450 (7167), pp. 203-218. (2007).
Collins et al., "Effects of irradiation dose rate on quality and sterility of Queensland fruit flies, *Bactrocera tryoni* (Froggatt)," J. Appl. Entomol. 132:398-405 (2008).
Condon et al., "Genetic sexing through the use of Y-linked transgenes", Insect Biochemistry and Molecular Biology, vol. 37, pp. 1168-1176, 2007.
Curtis et al., "Genetic sex separation in Anopheles arabiensis and the production of sterile hybrids", Bulletin in the World of Health Organization, vol. 56, No. 3, pp. 453-454, 1978.

Curtis et al., "Genetic Sexing System in *Anopheles-gambiae* Species A", Mosquito News, vol. 36, No. 4, pp. 492-498, 1976.
Daborn et al., "Evaluating the insecticide resistance potential of eight *Drosophila melanogaster* cytochrome P450 genes by transgenic over-expression", Insect Biochemistry and Molecular Biology, vol. 37, pp. 512-519, 2007.
Dang, Y. et al. Optimizing sgRNA Structure to Improve CRISPR-Cas9 Knockout Efficiency. Genome Biology 16 (December): 280, (2015).
Dicarlo, J. E. et al., "Safeguarding CRISPR-Cas9 gene drives in yeast", Nature Biotechnology, vol. 33, No. 12, pp. 1250-1255, (2015).
Doench, J.G. et al., Optimized sgRNA Design to Maximize Activity and Minimize off-Target Effects of CRISPR-Cas9, Nature Biotechnology, vol. 34, No. 2, pp. 184-191, 2016.
Feng, et al. "Vanillic acid derivatives from the green algae *Cladophora socialis* as potent protein tyrosine phosphatase 1B inhibitors." Journal of natural products 70.11 (2007): 1790-1792.
Focks et al., "An improved separator for the developmental stages, sexes, and species of mosquitoes (Diptera: Culicidae)", Journal of Medical Entomology, vol. 17, No. 6, pp. 567-568, 1980.
Galizi, R. et al., A synthetic sex ratio distortion system for the control of the human malaria mosquito. Nat. Commun. vol. 5, (2014).
Galizi, R., A. Hammond, K. Kyrou, C. Taxiarchi, F. Bernardini, S. M. O'Loughlin, P. A. Papathanos, T. Nolan, N. Windbichler, and A. Crisanti. 2016. "A CRISPR-Cas9 Sex-Ratio Distortion System for Genetic Control." Scientific Reports 6: 31139.
Gantz, V. M. et al., Highly efficient Cas9-mediated gene drive for population modification of the malaria vector mosquito *Anopheles stephensi*, PNAS, vol. 112, No. 49, pp. E6736-E6743, (2015).
Gantz, V. M., N. Jasinskiene, O. Tatarenkova, A. Fazekas, V. M. Macias, E. Bier, and A. A. James. 2015. "Highly Efficient Cas9-Mediated Gene Drive for Population Modification of the Malaria Vector Mosquito *Anopheles stephensi*." Proceedings of the National Academy of Sciences of the United States of America 112 (49): E6736-43.
Gimble, F. Invasion of a multitude of genetic niches by mobile endonuclease genes. FEMS Microbiol. Lett. vol. 185, pp. 99-107 (2000).
Gitzinger et al., "The food additive vanillic acid controls transgene expression in mammalian cells and mice," Nucleic Acids Research 40 (2012).
Godfray, H. C. J., A. North, and A. Burt. 2017. "How Driving Endonuclease Genes Can Be Used to Combat Pests and Disease Vectors." BMC Biology 15 (1): 81.
Gokhale, Chaitanya S., Richard Guy Reeves, and Floyd A. Reed. 2014. "Dynamics of a Combined Medea-Underdominant Population Transformation System." BMC Evolutionary Biology 14: 98.
Gong et al., "A dominant lethal genetic system for autocidal control of the Mediterranean fruit fly," Nat. Biotechnol. 23:453-456 (2005).
Gossen et al., "Tight control of gene expression in mammalian cells by tetracycline-responsive promoters," Proc Natl Acad Sci USA 89:5547-5551 (1992).
Hagmann et al., "The VP16 paradox: Herpes simplex virus VP16 contains a long-range activation domain but within the natural multiprotein complex activates only from promoter-proximal positions," J Virol 71:5952-5962 (1997).
Hammond, A., R. Galizi, K. Kyrou, A. Simoni, C. Siniscalchi, D. Katsanos, M. Gribble, et al. 2016. "A CRISPR-Cas9 Gene Drive System Targeting Female Reproduction in the Malaria Mosquito Vector Anopheles Gambiae." Nature Biotechnology 34 (1): 78-83.
Handler et al., "Use of the piggyBac transposon for germ-line transformation of insects", Insect Biochemistry and Molecular Biology, vol. 32, pp. 1211-1220, 2002.
Harwood et al., "The beta-ketoadipate pathway and the biology of self-identity," Ann Rev Microbiol 50:553-590 (1996).
Heravi, et al. "Transcriptional regulation of the vanillate utilization genes (vanABK operon) of Corynebacterium glutamicum by VanR, a PadR-like repressor", Journal of Bacteriology, JB.02431-14, pp. 1-60., (2014).

(56) References Cited

OTHER PUBLICATIONS

Hendrichs et al., "Medfly area wide sterile insect technique programmes for preventions, suppression or eradication: The importance of mating behavior studies," Fla Entomol 85:1-13 (2002).
Hollingdale, M., et al., Nussenzweig, R. S. Inhibition of entry of Plasmodium falciparum and P. vivax sporozoites into cultured cells; an in vitro assay of protective antibodies. J. Immunol. 132, pp. 909-913, (1984).
Hongenboom, Melissa, "Genetically modified flies 'could save crops'", BBC News, Science and Environment, Aug. 12, 2014. 3 pages.
Huang, Y. et al. Introducing Desirable Transgnes into Insect Populations Using Y-Linked Meiotic Drive? A Tehoretical Assesement, Evolution vol. 61, pp. 717-726.
Issacs, A., et al. Engineered Resistance to Plasmodium falciparum Development in Transgenic Anopheles stephensi. PLOS Pathog. 7, e1002017 (2011).
Iwaki et al., "Rapid selection of Drosophila S2 cells with the puromycin resistance gene", Biotechniques, vol. 35, pp. 482-486, 2003.
Kakkar, et al., "A review on protocatechuic acid and its pharmacological potential." ISRN pharmacology 2014 (2014).
Kerremans et al., "Use of a Temperature-Sensitive Lethal Mutation Strain of Medfly (Ceratitis-capitata) for the Suppression of Pest Populations", Theoretical and Applied Genetics, vol. 90, pp. 511-518, 1995.
Kim et al., "A genetic sexing strain of Anopheles quadrimaculatus, species A", Journal of the American Mosquito Control Association, vol. 3, No. 1, pp. 50-53, 1987.
Kim, et al., "Vanillic acid glycoside and quinic acid derivatives from Gardeniae Fructus." Journal of natural products 69.4 (2006): 600-603.
Koonin, E., et al., Diversity, classification and evolution of CRISPR-Cas systems. Curr. Opin. Microbiol. 37, pp. 67-78, (2017).
Koonin, E., et al. Evolutionary Genomics of Defense Systems in Archaea and Bacteria. Annu. Rev. Microbiol. 71, 233-261 (2017).
Krafsur et al., "Screwworm eradication is what it seems," Nature 323:495-496 (1986).
Krafsur et al., "Screwworm eradication in North and Central America," Parasitology Today 3:131:137 (1987).
Kuhlman, et al. Combinatorial transcriptional control of the lactose operon of Escherichia coli, Proceedings of the National Academy of Sciences, USA, 104(14): 6043-48., (2007).
Labbe et al., "Female-specific flightless (fsRIDL) phenotype for control of Aedes albopictus," PLoS Negl Trop Dis 6, e1724 (2012).
Leftwich et al., "Genetic elimination of field-cage populations of Mediterranean fruit flies", Proc. R. Soc., vol. 281, No. 1792, 21 pages, 2014.
Lewin, Genes V, Oxford University Press, Oxford, pp. 847-873, Fifth Edition.
Li, F. et al. An Anti-Chitinase Malaria Transmission—Blocking Single-Chain Antibody as an Effector Molecule for Creating a Plasmodium falciparum—Refractory Mosquito. J. Infect. Dis. 192, pp. 878-887 (2005).
Lines et al., "Genetic sexing systems in Anopheles arabiensis Patton (Diptera: Culicidae)", Journal of Economic Entomology, vol. 78, pp. 848-851, 1985.
Lyttle, T. Experimental population genetics of meiotic drive systems I. Pseudo-Y chromosomal drive as a means of eliminating cage populations of Drosophila melanogaster, Genetics, vol. 86, pp. 413-445, (1977).
Magnusson et al., "Transcription regulation of sex-biased genes during ontogeny in the malaria vector Anopheles gambiae", PLoS One, vol. 6, No. 6, e21572, 2011.
Malavasi, A. Project Aedes transgenic population control in Juazeiro and, Jacobina Bahia, Brazil. BMC Proc. 8, O11 (2014).
Marois et al. High-throughput sorting of mosquito larvae for laboratory studies and for future vector control interventions, Malaria Journal, vol. 11, No. 1, pp. 302-308, 2012.
Marshall, J. et al The Impact of Dissociation on Transposon-Mediated Disease Control Strategies. Genetics vol. 178, pp. 1673-1682 (2008).
Martinez et al., Biodegradation of lignocellulosics: microbial, chemical, and enzymatic aspects of the fungal attack of lignin, Int Microbiol 8:195-204 (2005).
Mathur, G. et al., Transgene-mediated suppression of dengue viruses in the salivary glands of the yellow fever mosquito, Aedes aegypti. Insect Mol. Biol. 19, pp. 753-763 (2010).
McCauley, et al, Analysis of a Human Sperm CD52 Glycoform in Primates: Identification 1-30 of an Animal Model for Immunocontraceptive Vaccine.Development, Biology of Reproduction, vol. 66, pp. 1681-1688, (2002).
McDonald et al., "A Genetic-Sexing Strain Based on Malathion Resistance for Culex-Tarsalis", Mosquito News, vol. 42, No. 4, pp. 531-536, 1982.
Medici et al., "Studies on Aedes albopictus larval mass-rearing optimization", Journal of Economic Entomology, vol. 104, No. 1, pp. 266-273, 2011.
Merkens et al., Vanillate metabolism in Corynebacterium glutamicum, Curr Microbiol 51:59-65 (2005).
Morrison et al., "Engineered repressible lethality for controlling the pink bollworm, a lepidopteran pest of cotton," PLoS One 7:e50922 (2012).
Nishimura et al., "Molecular cloning of Streptomyces genes encoding vanillate demethylase," Biosci Biotech Bioch 70:2316-2319 (2006).
Noble, C. et al., "Evolutionary dynamics of CRISPR gene drives", Science Advances, 5, vol. 3, e1601964, (2017).
Nuckolls, N. L., M. A. Bravo Nunez, M. T. Eickbush, J. M. Young, J. J. Lange, J. S. Yu, G. R. Smith, S. L. Jaspersen, H. S. Malik, and S. E. Zanders. 2017. "Wtf Genes Are Prolific Dual Poison-Antidote Meiotic Drivers." eLife 6. https://doi.org/10.7554/eLife.26033.
Oberhofer, G. et al., Behavoir for Homin Endoclease Gene Drives targeting Genes Required for Viability or Femal Fertility with Multiplexted Guide RNAs, (2018).
Papathanos et al., "Sex Ratio Manipulation for Insect Population Control", Transgenic Insects: Techniques and Applications, pp. 83-100, Publication date Oct. 29, 2014.
Papathanos, et al., "Sex Separation Strategies: past experience and new approaches", Malaria Journal, vol. 8, Suppl 2, No. S5, 2009.
Pomiankowski et al., "The evolution of the Drosophila sex-determination pathway", Genetics, vol. 166, pp. 1761-1773, 2004.
Poindexter, "Biological properties and classification of the Caulobacter group," Bacteriol Rev 28:231-295 (1964).
Popovici, J. et al, Assessing key safety concerns of a Wolbachia-based strategy to control dengue transmission by Aedes mosquitoes. Mem. Inst. Oswaldo Cruz 105, pp. 957-964, (2010).
Port, F. et al., Optimized CRISPR/Cas Tools for Efficient Germline and Somatic Genome Engineering in Drosophila. Proceedings of the National Academy of Sciences of the United States of America 111 (29), pp. E2967-E2976. (2014).
Preston, Christine R., Carlos C. Flores, and William R. Engels. 2006. "Differential Usage of Alternative Pathways of Double-Strand Break Repair in Drosophila." Genetics 172 (2): 1055-68.
Reeves, R. G., J. Bryk, P. M. Altrock, J. A. Denton, and F. A. Reed. 2014. "First Steps towards Underdominant Genetic Transformation of Insect Populations." PLoS One 9 (5): e97557.
Rendon et al., "Medfly (Diptera: Tephritidae) genetic sexing: large-scale field comparison of males-only and bisexual sterile fly releases in Guatemala", Journal of Economic Entomology, vol. 97, No. 5, pp. 1544-1553, 2004.
Resnik, D., Ethical Issues in Field Trials of Genetically Modified Disease-Resistant Mosquitoes, Dev. World Bioeth, vol. 14, pp. 37-46, (2014).
Restriction Requirement dated Feb. 23, 2015 in U.S. Appl. No. 14/206,011.
Restriction Requirement dated Sep. 14, 2015 in U.S. Appl. No. 14/631,171.
Robinson et al., "Cytological, linkage and insecticide studies on a genetic sexing line in Anopheles stephensi Liston", Heredity, vol. 58, pp. 95-101, 1987.

(56) References Cited

OTHER PUBLICATIONS

Royden, C., et al., The Tko Locus, Site of a Behavioral Mutation in *D. melanogaster*, Codes for a Protein Homologous to Prokaryotic Ribosomal Protein S12. Cell 51 (2), pp. 165-173, (2004).
Sambrook et al., Molecular Cloning, A Laboratory Manual, Cold Springs Harbor Press, Cold Springs Harbor, N. Y. 1989, Second Edition.
Seawright et al., "Genetic method for the preferential elimination of females of anopheles albimanus", Science, vol. 200, No. 4347, pp. 1303-1304, 1978.
Sebrovskii, A. et al. A New Possible Method of Pest Control. Zool Zh, vol. 19, pp. 618-630, (1940).
Segura et al., "Genetic analysis of a chromosomal region containing vanA and vanB, genes required for conversion of either ferulate or vanillate to protocatechuate in Acinetobacter," J Bacteriol 181:3494-3504 (1999).
Seidel, H. S., M. Ailion, J. Li, A. van Oudenaarden, M. V. Rockman, and L. Kruglyak. 2011. "A Novel Sperm-Delivered Toxin Causes Late-Stage Embryo Lethality and Transmission Ratio Distortion in C. Elegans." PLoS Biology 9 (7): e1001115.
Shaner, N. et al., Improved Monomeric Red, Orange and Yellow Fluorescent Proteins Derived from *Discosoma* Sp. Red Fluorescent Protein, Nature Biotechnology, 22 (12), pp. 1567-1572, (2004).
Shetty, "Genetic sexing system for the preferential elimination of females in Culex quinquefasciatus", Journal of the American Mosquito Control Association, vol. 3, No. 1, pp. 84-86, 1987.
Shmakov, S. et al., Discovery and Functional Characterization of Diverse Class 2 CRISPR-Cas Systems. Mol. Cell 60, 385-397 (2015).
Shmakov, S. et al., Diversity and evolution of class 2 CRISPR-Cas systems. Nat. Rev. Microbiol. 15, pp. 169-182 (2017).
Simoni, A. et al., Development of synthetic selfish elements based on modular nucleases in *Drosophila melanogaster*. Nucleic Acids Res. vol. 42, pp. 7461-7472 (2014).
Singleton et al., Title Page of Dictionary of Microbiology and Molecular Biology, J. Wiley & Sons, New York, N. Y., 1994, Second Edition.
Steller et al., "A Transposable P Vector That Confers Selectable G418 Resistance to *Drosophila* Larvae", EMBO Journal, vol. 4, No. 1, pp. 167-171, 1985.
Sun, N., and H. Zhao. 2014. "A Single-Chain TALEN Architecture for Genome Engineering." Molecular bioSystems 10 (3): 446-53.
Thanbichler et al., "A comprehensive set of plasmids for vanillate- and xylose-inducible gene expression in Caulobacter crescentus," Nucleic Acids Res 35:e137 (2007).
Travanty, E., et al., Using RNA interference to develop dengue virus resistance in genetically modified Aedes aegypti. Insect Biochem. Mol. Biol. 34, pp. 607-613, (2004).
Wade, M. J., and R. W. Beeman. 1994. "The Population Dynamics of Maternal-Effect Selfish Genes." Genetics 138 (4): 1309-14.
Ward, Catherine M., Jessica T. Su, Yunxin Huang, Alun L. Lloyd, Fred Gould, and Bruce A. Hay. 2011. "Medea Selfish Genetic Elements as Tools for Altering Traits of Wild Populations: A Theoretical Analysis." Evolution; International Journal of Organic Evolution 65 (4): 1149-62.
WHO World Malaria Report dated 2014, accessed on the world wide web at <who.int/malaria/publications/world_malaria_report_2014/en/>.
Windbichler, Nikolai, Philippos Aris Papathanos, Flaminia Catteruccia, Hilary Ranson, Austin Burt, and Andrea Crisanti. 2007. "Homing Endonuclease Mediated Gene Targeting in Anopheles Gambiae Cells and Embryos." Nucleic Acids Research 35 (17): 5922-33.
Windbichler, N., P. A. Papathanos, and A. Crisanti. 2008. "Targeting the X Chromosome during Spermatogenesis Induces Y Chromosome Transmission Ratio Distortion and Early Dominant Embryo Lethality in Anopheles Gambiae." PLoS Genetics.
Xie, et al., "Antagonistic control of a dual-input mammalian gene switch by food additives." Nucleic acids research (2014): gku545.
Yamada et al., "Genetic sex separation of the malaria vector, Anopheles arabiensis, by exposing eggs to dieldrin", Malaria Journal, vol. 11, No. 1, pp. 208-219, 2012.
Yen, P. et al. Synthetic miRNAs induce dual arboviral-resistance phenotypes in the vector mosquito *Aedes aegypti*. Commun. Biol. 1, pp. 11 (2018).
Zeh et al., "From father to son: transgenerational effect of tetracycline on sperm viability," Sci Rep 2:375 (2012).
Gloor et al., Targeted Gene Replacement in Drosophiloa Via P. Element-induced Gap Repair, Science, vol. 253, No. 5024, pp. 1110-1117, 1991.
Hamza et al., Complementation of Yeast Genes With Human Genes as an Experimental Platform for Functional Testing or Human Genetic Variants, genetics, vol. 201, pp. 1263-1274, 2015.
Office Action dated Oct. 1, 2020 in U.S. Appl. No. 15/970,728.
Tham et al., Mismatch Repair and Homoeologous Recombination, DNA Repair, vol. 38, pp. 75-83, 2016.

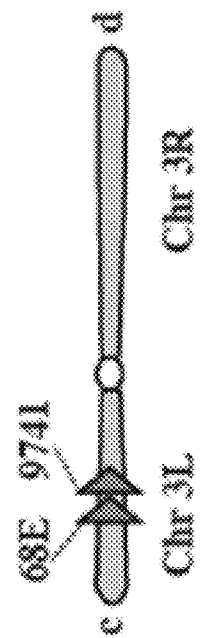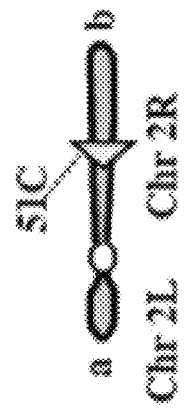
FIG. 6A

FIG. 16

| parental genotypes | | progeny genotype (%) | embryo survival % | | transgene bearing adults % | |
|---|---|---|---|---|---|---|
| male | female | | predicted | observed* | predicted | observed* |
| $T_1/T_1 ; T_2/T_2$ | $T_1/T_1 ; T_2/T_2$ | $T_1/T_1 ; T_2/T_2$ (100%) | 100 | 96.9 ± 1.8 / 96.9 ± 0.3 | 100 | 100 ± 0.0 / 100 ± 0.0 |
| $T_1/T_1 ; T_2/T_2$ | +/+ ; +/+ | $T_1/+ ; T_2/+$ (100%) | 100 | 94.6 ± 2.2 / 98.2 ± 2.6 | 100 | 100 ± 0.0 / 100 ± 0.0 |
| +/+ | $T_1/T_1 ; T_2/T_2$ | $T_1/+ ; T_2/+$ (100%) | 100 | 90.1 ± 1.6 / 92.5 ± 4.8 | 100 | 100 ± 0.0 / 100 ± 0.0 |
| $T_1/+ ; T_2/+$ | +/+ ; +/+ | $T_1/+ ; T_2/+$ (25%) $T_1/+ ; +/+$ (25%)** $+/+ ; T_2/+$ (25%)** $+/+ ; +/+$ (25%) | 50 | 51.2 ± 1.6 / 50.4 ± 1.3 | 50 | 49.3 ± 3.4 / 49.5 ± 2.4 |
| +/+ ; +/+ | $T_1/+ ; T_2/+$ | $T_1/+ ; T_2/+$ (25%) $T_1/+ ; +/+$ (25%)** $+/+ ; T_2/+$ (25%)** $+/+ ; +/+$ (25%) | 50 | 48.3 ± 2.8 / 49.3 ± 3.9 | 50 | 49.4 ± 2.2 / 48.5 ± 3.4 |
| $T_1/+ ; T_2/+$ | $T_1/+ ; T_2/+$ | $T_1/T_1 ; T_2/T_2$ (6.25%) $T_1/T_1 ; +/+$ (12.5%)** $T_1/+ ; T_2/T_2$ (12.5%)** $T_1/+ ; +/+$ (25%) $T_1/+ ; T_2/+$ (6.25%)** $+/+ ; T_2/T_2$ (12.5%)** $+/+ ; T_2/+$ (12.5%)** $+/+ ; +/+$ (6.25%) | 37.5 | 36.2 ± 1.8 / 32.4 ± 4.0 | ~83% | 80.4 ± 6.5 / 80.8 ± 5.8 |

* Translocations S1C768E (top) and S1C79741 (bottom)
** These genotypes are not viable.

FIG. 17

| Primer name | Primer sequence, 5' to 3' | Source |
|---|---|---|
| P1 | CCTAACAACTCACACCTTGCAGGCCACCTGGCCTAGAGATCCACCAACTTTTTG CACTGC (SEQ ID NO: 1) | pIZ/V5-His/CAT (Invitrogen) |
| P2 | ATTCCTAAGCATCAGTGGTTGAACCTACCTTGTGGGTGACCAGAGACAGGTTGC GGCG (SEQ ID NO: 2) | pFUSEss-CHIg-mG1 (Invivogen) |
| P3 | AGGTTCAACCACTGATGCTTAGGAATAGGCCATGTGAAGCTGAAGGAATC (SEQ ID NO: 3) | |
| P4 | TATTACCCGTTATCCCTACTAGTAGGGATAACAGGGTAATACTAGAATCCCTGGGC ACAATTT (SEQ ID NO: 4) | pFUSEss-CHIg-mG1 (Invivogen) |
| P5 | CTAGTATTACCCGTGTTATCCCTACTAGTAGGGATAACAGGGTAATAGTGGTTGTAAG CCTTGCA (SEQ ID NO: 5) | |
| P6 | AAAGGATAAGAATTAGGGTCGTTTCGGTGTGCCTAGTTTACCAGAGAGTGG GAGA (SEQ ID NO: 6) | |
| P7 | CGCCCACGCCATCCAACCGCCAACCTGTCTCTGGTCACGCCAACAAGGTAG GTTC (SEQ ID NO: 7) | P3/P4 XYZ PCR |
| P8 | ATGACGTTCTTGGAGGAGCGCACCATTTGTTGCTAAAGGAAAGGATAAGAATTAG GGTT (SEQ ID NO: 8) | P5/P6 UVW PCR |
| P9 | AAACGACTAACCCTAATTCTATCCTTTCCTTAGCAACAAAATGGTGCGCTCCTCC AAG (SEQ ID NO: 9) | pMos-3xP3-DsRed-attp (addgene plasmid #52904) |
| P10 | AATGGAACTCTTCGCGGCCAGGTGGCGCTGCAAGGCTCGAGGGTCGACTGATCATA ATCA (SEQ ID NO: 10) | |
| P11 | GGATCCGGGAATTGGGCAATATTTAAATGGCGGCCTTGCAGGCCACCT GGCC (SEQ ID NO: 11) | Drosophila genomic DNA |
| P12 | AGCGTGTTTTTGCAGTGCAAAAAGTTGGTGGATCTCTAGGGCCAGGTGGCGCT GCAA (SEQ ID NO: 12) | |
| P15 | CCAACGCATTTCCAAGCTGTGTTTAAACGTGGATCTCTAGGGCCAGGTGGCGCTGCA AGG (SEQ ID NO: 15) | |

FIG. 17 CONTINUED

| | | |
|---|---|---|
| P13 | TACAAATGTGGTATGGCTGATTATGATCAGTCGACCCTCGAGCCTTGCAG CGCCACCTGG (SEQ ID NO: 13) | Drosophila genomic DNA |
| P14 | GAGACCGTGACCTACATCGTCGACACTAGTGGATCTCTAGGGCCAGGTG GCGCTGCAAGG (SEQ ID NO: 14) | Drosophila genomic DNA |
| P16 | CCTTGCAGCGCCACCTGCGCCCTAGAGATCCACGTTAAACAAGCTTGAA AATGCGTTGG (SEQ ID NO: 16) | Drosophila genomic DNA |
| P17 | CGAAGCGCCTCTATTTATACTCCGGCGCTCGTTAAACAAAGTGGCAGGG CCCATGTGTT (SEQ ID NO: 17) | |
| P18 | GAGTGGAGCACAAACACATGGGCCCTGCCCACTTTGTTAAACGAGCGCC GGAGTATAAAT (SEQ ID NO: 18) | Drosophila genomic DNA |
| P19 | AAGCATCAGTGGTTGAACCTACCTTGTTGGCGTGTCTGATGCAGATTGTT TAGCTTGTTC (SEQ ID NO: 19) | |
| P20 | GCCACAAGGTAGGTTCAACCACTGATGCTTAGGAATAGGCGTGGTTGT AAGCCTTGCAT (SEQ ID NO: 20) | pFUSEss-CHIg-mG1 (Invivogen) |
| P21 | CCCTGTTATCCCTACTAGTAGGGATAACAGGGTAATACTAGTTTACCAGG AGAGTGGGAG (SEQ ID NO: 21) | |
| P22 | TATTACCCTGTTATCCCTACTAGTAGGGATAACAGGGTAATACATGTGAA GCTGAAGGAA (SEQ ID NO: 22) | pFUSEss-CHIg-mG1 (Invivogen) |
| P23 | AAAGGATAAGAATTAGGGTTAGTCGTTTCGGTGTGCCTAGAATCCCTGG CACAATTTTC (SEQ ID NO: 23) | |
| P24 | CAAGCGCAGCTGAACAAGCTAAACAATCTGCATCAGACACGCCAACAAG GTAGGTTCAAC (SEQ ID NO: 24) | P20/P21 UVW PCR |
| P25 | ACCTACACTGCGACACTAGTGGATCTCTAGCTCGAGTCTAAAGGAAAGG ATAAGAATTAGGG (SEQ ID NO: 25) | P22/P23 XYZ PCR |
| P26 | CCCTAATTCTTATCCTTTCCTTTAGGAATTCCAACAAAATGGTGAGCAAG GGCGAGGAGC (SEQ ID NO: 26) | pAAV-GFP (addgene plasmid #32395) |
| P27 | TTCACTGCATTCTAGTGTGGTTGTCCAAACTCATCAATGTTACTTGTA CAGCTCGTC (SEQ ID NO: 27) | |
| P28 | GCCGCCGGGATCACTCTCGGCATGGACGAGCTGTACAAGTAAACATTGA TGAGTTTGGAC (SEQ ID NO: 28) | pMos-3xP3-DsRed-attp (addgene plasmid #52904) |

FIG. 18

Full sequences of short fragments, and first and last 30 bps of longer fragments, used in the translocation constructs. Splice donors and acceptors are in bold and underlined.

| Name | Sequence |
|---|---|
| I-SceI Site | ATTACCCTGTTATCCCTA (SEQ ID NO: 29) |
| Rpl35a Intron 5' | CCATCCTCAAGGTATGTCTATACTTCAATGTGATGGGTCCGGACTTCACAGAGTTTTCA AATAATAATTAATA (SEQ ID NO: 30) |
| Rpl35a Intron 3' | CATTCCAGTTCTGTAAAACATTTTAGTAATGTAATTGATTAACCAACATATTACATTGC AGATTGAGGGC (SEQ ID NO: 31) |
| MHC16 Intron 5' | CACGCCAACAAGGTAGGTTCAACCACTGATGCTTAGGAATAGG (SEQ ID NO: 32) |
| MHC16 Intron 3' | CTAGGCACACGCGAAACGACTAACCCTAATTCTATCCTTTCCTTTAG (SEQ ID NO: 33) |

| Name | 30 bps of the 5' and 3' ends of each fragment, 5' to 3' |
|---|---|
| Opie2 5' end | CACCAACTTTTTGCACTGCAAAAAACAC (SEQ ID NO: 34) |
| Opie2 3' end | ATCCAACCGCCGCCAACCTGTCTCTGGT (SEQ ID NO: 35) |
| SVP 5' end | AAGCTTGGAAATGCGTTGGAGTAATAGCC (SEQ ID NO: 36) |
| SVP 3' end | GGAGCAACAAACACATGGGCCCTGCCACTTT (SEQ ID NO: 37) |
| Hsp70 basal 5' end | AGCGCGGAGTATAAATAGAGGCGCTTCGT (SEQ ID NO: 38) |
| Hsp70 basal 3' end | AAGCGCAGCTGAACAAGCTAAACAATCTGC (SEQ ID NO: 39) |
| Actin5 5' end | TAAAAAATCATGAATGGCATCAACTCTG (SEQ ID NO: 40) |
| Actin5 3' end | CATCAGCCAGCAGTCGTCTAATCCAGAGAC (SEQ ID NO: 41) |

FIG. 18 CONTINUED

| Name | 30 bps of the 5' and 3' ends of each fragment, 5' to 3' |
|---|---|
| XYZ 5' end | CATGTGAAGCTGAAGGAATCTGGCCCTGGG (SEQ ID NO: 42) |
| XYZ 3' end | AGGTGGACAAGAAATTGTGCCCAGGGATT (SEQ ID NO: 43) |
| UVW 5' end | GTGGTTGTAAGCCTTGCATATGTACAGTCC (SEQ ID NO: 44) |
| UVW 3' end | GAGAAGAGCCTCTCCCACTCTCCTGGTAAA (SEQ ID NO: 45) |
| GFP 5' end | ATGGTGAGCAAGGGCGAGGAGCTGTTCACC (SEQ ID NO: 46) |
| GFP 3' end | ACTCTCGGCATGACGAGCTGTACAAGTAA (SEQ ID NO: 47) |
| dsRed 5' end | ATGGTGCGCTCCTCCAAGAACGTCATCAAG (SEQ ID NO: 48) |
| dsRed 3' end | CTACAGGAACAGGTGGTGGCGGCCCTCGGT (SEQ ID NO: 49) |
| SV40 3'UTR 5' end | ACATTGATGAGTTTGGACAAACCACAACTA (SEQ ID NO: 50) |
| SV40 3'UTR 3' end | TGTGGTATGGCTGATTATGATCAGTCGACC (SEQ ID NO: 51) |
| CTCF 5' end | CCTTGCAGCGCCACCTGGCCCGAAGAGTT (SEQ ID NO: 52) |
| CTCF 3' end | GGCCAGGTGGCGCTGCAAGGTGTGAGTTGT (SEQ ID NO: 53) |

FIG. 19

Oligonucleotide primers used to determine the orientation of the attP insertion sites of various candidate attP lines.
[1]These attP primers were used in PCRs with all lines except 9741.
[2]These attP primers were used in PCRs with the 9741 line.

| Name | Sequence 5' to 3' |
|---|---|
| attP1-F[1] <br> attP1-R[1] | AGAGTCGTCGACGTCAAAATCACCAC (SEQ ID NO: 54) <br> GCATACATTATACGAAGTTATGAG (SEQ ID NO: 55) |
| attP2-F[2] <br> attP2-R[2] | AGGTTACCCCAGTTGGGGCACTACTC (SEQ ID NO: 56) <br> TAACCTTTGAGTTCTCTCAGTTGGGGGC (SEQ ID NO: 57) |
| 22A-F <br> 22A-R | AATGGATTCGTGCTCATCTTCTGG (SEQ ID NO: 58) <br> AGTGAAGTCAAACTTCTGTGAGTC (SEQ ID NO: 59) |
| 51C-F <br> 51C-R | CTCGCAAATGCCAGCAGGGTAATG (SEQ ID NO: 60) <br> TAGCGAATGAAAACTGCGAAGAAG (SEQ ID NO: 61) |
| 68E-F <br> 68E-R | CAATTACATTTCGATTGATTTTCA (SEQ ID NO: 62) <br> GCAAACATGACGTATGGAAAATATC (SEQ ID NO: 63) |
| 96E-F <br> 96E-R | GGTGCCGTGTGTCAAATGTGTCGC (SEQ ID NO: 64) <br> GATTAACGTGCTGCACGGCTCACG (SEQ ID NO: 65) |
| 9741-F <br> 9741-R | TACTTTTCGTAAACCATATTGAGATAC (SEQ ID NO: 66) <br> TAAAATGGACCTGTAGGAATTTACTTAC (SEQ ID NO: 67) |

FIG. 19 CONTINUED

Oligonucleotide primers used to confirm the novel association of promoter and reporter, and the presence of alleles in both attP sites, in translocation individuals.
[1] These primers were used to PCR opie2-GFP.
[2] These primers were used to PCRs syp-dsRed.
[3] These primers were used to confirm presence of constructs in both attP sites; assignment of forward and reverse status is random.

| Name | Sequence 5' to 3' |
|---|---|
| Opie2-F[1]<br>GFP-R[1] | CACCAACTTTTTGCACTGCAAAAAACAC (SEQ ID NO: 68)<br>ACTCTCGGCATGGACGAGCTGTACAAGTAA (SEQ ID NO: 69) |
| Hsp70-F[2]<br>dsRed-R[2] | TCAAACAAGCAAAGTGAACACATCG (SEQ ID NO: 70)<br>CTACAGGAACAGGTGGTGGCGGCCCTCGGT (SEQ ID NO: 71) |
| SV40-F[3]<br>51C-R[3]<br>68E-F[3]<br>9741-F[3] | ACATTGATGAGTTTGGACAAACCACAACTA (SEQ ID NO: 72)<br>TAGCGAATGAAAACTGCGAAGAAG (SEQ ID NO: 61)<br>CAATTACATTTCGATTGATTTTCA (SEQ ID NO: 62)<br>TACTTTTCGTAAACCATATTGAGATAC (SEQ ID NO: 66) |

FIG. 19 CONTINUED

| Name | Sequence |
|---|---|
| Kozak sequence | CAACAAA (SEQ ID NO: 73) |
| Two 18bp I-SceI recognition sequences w/ linker | ATTACCCTGTTATCCCTA-CTAG-TAGGGATAACAGGGTAAT (SEQ ID NO: 74) |
| Linker sequence | CTAG (SEQ ID NO: 75) |

POPULATION CONTROL USING ENGINEERED TRANSLOCATIONS

CROSS-REFERENCE TO RELATED APPLICATIONS

This application claims the benefit of U.S. Provisional Application 62/166,281 filed on May 26, 2015, which is hereby incorporated by reference in its entirety.

STATEMENT REGARDING FEDERALLY SPONSORED R&D

This invention was made with government support under Grant No. OD003878 awarded by the National Institutes of Health, and under Grant No. W911NF-11-2-0055 awarded by the U.S. Army, and under Grant No. 2012-51181-20086 awarded by the U.S.D.A. The government has certain rights in the invention.

REFERENCE TO SEQUENCE LISTING

The present application is being filed along with a sequence listing in electronic format. The sequence listing is provided as a file entitled CALTE116ASEQLIST.txt which is 14,384 bytes in size, created on May 25, 2016. The information in the electronic format of the Sequence Listing is incorporated herein by reference in its entirety.

FIELD

The present disclosure generally relates to methods and systems for control of insects by population replacement.

BACKGROUND

Insect vector-borne diseases, such as malaria and dengue fever, continue to significantly impact health worldwide, despite the efforts put forth to eradicate them. Suppression strategies utilizing genetically modified disease refractory insects have surfaced as a means of disease control, and progress has been made on engineering disease-resistant vector insects.

SUMMARY

In some embodiments, a method of distributing one or more genes of interest into a population of insects is provided. The method comprises providing an insect population. One or more individuals in the insect population comprises a translocation mediated gene drive system. The method further comprises inducing a chromosomal translocation in the one or more individuals in the insect population. The chromosomal translocation generates a translocation-bearing altered insect population, the translocation-bearing altered insect population comprises translocation-bearing individuals that are translocation heterozygotes and translocation-bearing individuals that are translocation homozygotes for the chromosomal translocation, and the translocation-bearing individuals display a fitness that is greater than that of the wildtype (non-translocation-bearing) individuals when challenged in a condition in which a translocation-based drive occurs.

In some embodiments, one or more genes of interest in the translocation-bearing altered insect population encodes for a disease prevention protein/disease refractory protein, or a gene conferring conditional lethality, inability to undergo diapause, sterility, inability to fly. In some embodiments, the fitness is defined as a population genetic behavior, over multiple generations, of translocation chromosomes in populations comprising both translocation-bearing individuals and non-translocation-bearing individuals. A chromosomal translocation is defined as having a higher fitness than wildtype under conditions that result in translocation-bearing chromosomes increasing in frequency over multiple generations, a translocation is defined as having a lower fitness than wildtype under conditions that result in translocation-bearing chromosomes decreasing in frequency over multiple generations, and fitness is frequency dependent such that a higher frequency of a first genotype results in an increase in relative fitness of the first genotype with respect to alternative genotypes. In some embodiments, the high frequency is defined as when translocation-bearing versions of chromosomes make up greater than about 90% of the total chromosomes in a population as compared to wild type versions of the chromosomes involved in generating the translocation.

In some embodiments, the rapid rate is defined as replacement of at least 90% of the wild type population chromosomes by the translocation-bearing altered insect population (translocation) after at most 5 generations. In some embodiments, the translocation-bearing altered insect population replaces 90% of the target wild type population after 30 generations. In some embodiments, the insect is a mosquito. In some embodiments, the condition in which translocation-based drive occurs comprises one or more of a population cage, a field cage, or an open environment. In some embodiments, the chromosomal translocation spreads to a high frequency within the wild population. In some embodiments, the translocation-bearing altered insect population is capable of replacing the wild type population at a rapid rate. In some embodiments, the insect is a psyllid. In some embodiments, a translocation mediated gene drive system is provided. The gene drive system comprises a first construct, configured to be positionable at a first insertion site in a first chromosome. The first construct comprises: a) a first location to insert a first gene of interest; b) a first promoter; c) a first fragment of foreign stuffer DNA; d) a second fragment of foreign stuffer DNA; e) a first target site and, in some cases, a second target site for an endonuclease positioned between the first and second fragments of foreign stuffer DNA; f) a first splice acceptor site, positioned downstream from a-e; and g) a first splice donor site, positioned between b and c. The system includes a second construct, configured to be positionable at a second insertion site in a second chromosome. The second construct comprises: h) a second location to insert a second gene of interest; i) a second promoter; j) a third fragment of foreign stuffer DNA, wherein the third fragment is homologous to the second fragment; k) a fourth fragment of foreign stuffer DNA, wherein the fourth fragment is homologous to the first fragment; l) a second target site, in the case where two target sites are used, and a fourth target site, in the case where four cleavage sites are used, for an endonuclease positioned between the third and fourth fragments of foreign stuffer DNA; m) a second splice acceptor site, positioned downstream from h-l, and n) a second splice donor site, positioned between i and j. The first and second chromosomes are non-homologous chromosomes, the first fragment of foreign stuffer DNA is homologous to the fourth fragment of foreign stuffer DNA and the second fragment of foreign stuffer DNA is homologous to the third fragment of foreign stuffer DNA, a double stranded break created at the first, second, third and fourth target sites allows for homologous recombination between the first and fourth fragments, and between the second and third fragments upon a repair of the double stranded break, and wherein the repair of the DSB induces a chromosomal translocation and generates a first translocation chromosome and a second translocation chromosome.

In some embodiments, the size of the first fragment of foreign stuffer DNA is about 50 bp to about 10 kb. In some embodiments, the size of the second fragment of foreign stuffer DNA is about 50 bp to about 10 kb. In some embodiments, the size of the third fragment of foreign stuffer DNA is about 50 bp to about 10 kb. In some embodiments, the size of the fourth fragment of foreign stuffer DNA is about 50 bp to about 10 kb. In some embodiments, the first insertion site and second insertion site comprise an insertion site combination. In some embodiments, the first and second insertion sites are located in a gene desert, wherein the gene desert has no genes in a region encompassing at least 10 kb. In some embodiments, the transgene insertion is located at least 5 kb from a gene. In some embodiments, the first and second constructs inserted in the first and second insertion sites, respectively are oriented in the same direction with respect to the centromere of the first and second chromosomes. In some embodiments, the construct is transferable to a mosquito. In some embodiments, the system is self-perpetuating/self-propagating when present at a high frequency. In some embodiments, the system can be eliminated from the population by introducing a high frequency of wildtype individuals. In some embodiments, creation of a translocation can occur through the repair of the DSB by a simple non-homologous end joining of broken DNA ends instead of by homologous recombination.

In some embodiments, a population of translocation bearing insects is provided that comprising the system provided herein. In some embodiments, the insects are mosquitos. In some embodiments, the insects are psyllids.

BRIEF DESCRIPTION OF THE DRAWINGS

FIG. 6A-FIG. 6E show schematic illustrations of the synthetic biology approach used to generate reciprocal chromosomal translocations.

FIG. 16. shows results of reciprocal translocation experiments in flies.

FIG. 17 provides a set of sequences used herein.

FIG. 18 provides a set of sequences used herein.

FIG. 19 provides a set of sequences used herein.

DETAILED DESCRIPTION

Figure 1A:
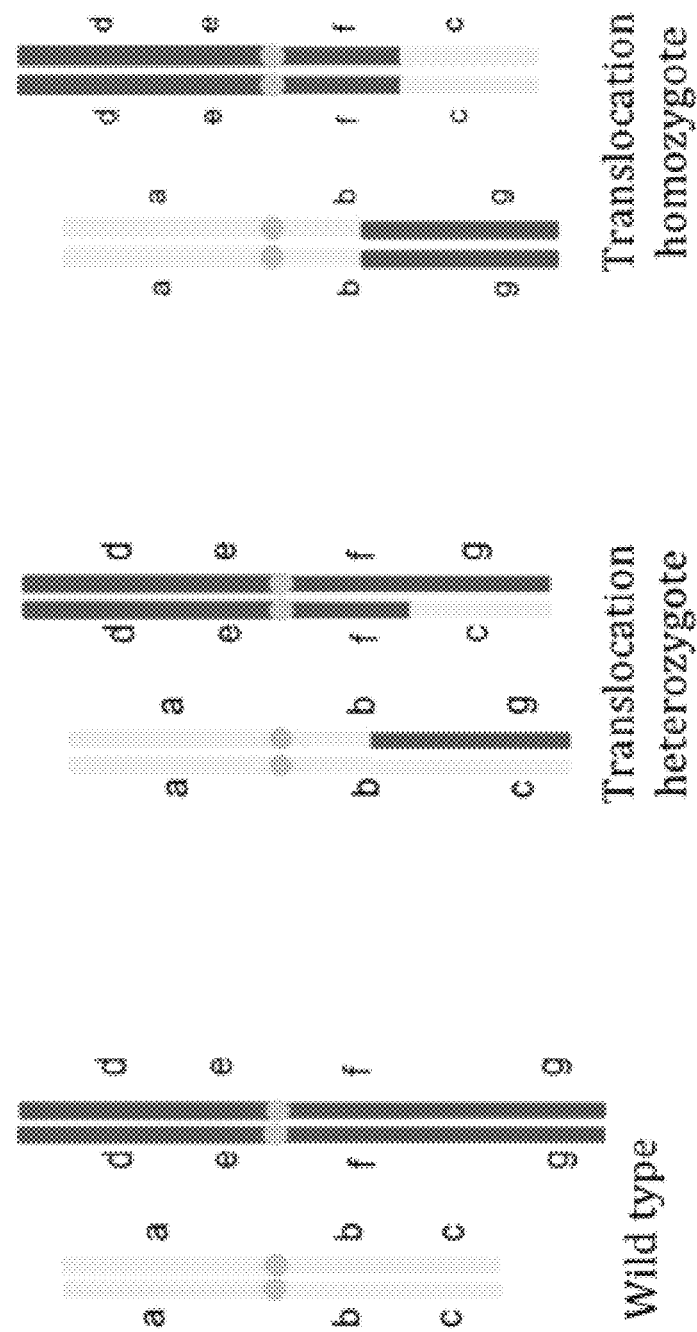
FIG. 1A-FIG. 1B show illustrations of the conceptual framework of reciprocal chromosomal translocation.

Provided herein is a portable synthetic biology technique to generate reciprocal chromosomal translocations at specific sites in the genome in a manner that allows for easy detection of translocation-bearing individuals, and for facile inexorable linkage of genes of interest to the translocation breakpoints. Importantly, it is demonstrated herein, in a model organism, that the translocation strains have high fitness and are capable of rapidly replacing wild type populations of *Drosophila melanogaster* in a threshold-dependent manner.

Introduction

Insects act as vectors for a number of important diseases of humans, animals, and plants. Examples include dengue, yellow fever, lymphatic filariasis, chikungunya, and Chagas disease (humans), malaria and West Nile (humans and birds), Rift valley fever and trypanosomyasis (humans and livestock), and plant diseases such as Huanglongbing (citrus), almond leaf scorch, Pierces disease (grapes), and zebra chip disease (potato) (reviewed in (Nicholson, 2007)). And, increased global movement of commodities, people, and animals is leading to the spread of disease vectors and pathogens into new environments (de La Rocque et al., 2011; Randolph and Rogers, 2010; Tatem et al., 2006). Vector control is always an important component of disease prevention. However, it is often expensive, with the degree of protection provided being proportional, on an on-going basis, to the effort and money put into control. Additionally, specific methods of vector control, such as environment modification or use of insecticides, may be impractical or have undesirable side effects in certain contexts. A complementary strategy for disease prevention, first articulated many decades ago (Curtis, 1968), involves replacement of wild, disease-transmitting insect populations with individuals that are engineered to be refractory to disease transmission, but that are still subject to vector control (reviewed in (Hay et al., 2010)). A central appeal of this strategy is that in contrast to vector suppression alone, population replacement is species-specific and potentially self-perpetuating.

Several of the above-mentioned gene drive systems, including Medea, HEGs, transposable elements, male meiotic drive, intracellular symbiotic *Wolbachia*, and CRISPR/Cas, are predicted to be invasive drive mechanisms with a low release threshold, capable of spreading to high frequency even when introduced into an area in only a few individuals (Deredec et al., 2008; Esvelt et al., 2014; Jansen et al., 2008; Marshall, 2009; Marshall et al., 2011). Invasive gene drive mechanisms are ideal when the goal is to spread genes over a large area, particularly when migration rates between the release site and surrounding areas of interest are low. However, because such systems have a low release threshold, once introduced, the pretransgenic state cannot easily be restored by diluting the replaced population with wild-type individuals such that the frequency of the gene drive chromosome falls below the threshold frequency required for spread. Therefore, given their potency and difficulty of removal, developing regulations for invasive gene drive systems should be a high priority issue (Oye et al., 2014). In contrast to invasive gene drive mechanisms, several other proposed drive mechanisms have significant (27%-67%) introduction thresholds that must be surpassed in order for gene drive to occur. Examples include a large number of novel single locus gene drive mechanisms (Marshall and Hay, 2012b), as well as chromosome translocations, inversions, compound chromosomes, and various forms of engineered underdominance (Akbari et al., 2013; Curtis, 1968; Davis et al., 2001; Magori and Gould, 2006). In all of these latter systems, gene drive relies on the phenomenon of underdominance, in which heterozygotes (or their progeny) have a lower fitness than either parental homozygote (or trans-heterozygote, in some three allele cases).

Underdominance-based systems have the features of a bi-stable switch: if the frequency of one allele or chromosome type is above a critical threshold frequency, it will spread to genotype or allele fixation, while if the frequency is below the threshold, it will be lost in favor of the other allele or chromosome type. Consequently, transgenes introduced into populations using underdominance-based gene drive mechanisms can easily be removed from the wild population through dilution of the replaced population with wild type individuals. A relatively high introduction threshold also has the effect of preventing transgene spread to high frequency in neighboring populations linked to the release site by low levels of migration, because the frequency of the drive chromosome never crosses the required threshold (Altrock et al., 2011; Altrock et al., 2010). Gene drive mechanisms with a high introduction threshold are ideal when the goal is to bring about reversible, and local, population replacement. Scenarios in which this is likely to be important include during field tests of the efficacy of genes that mediate disease refractoriness, and in social and regulatory environments in which approval of transgenic organisms is limited to specific regions (Knols et al., 2007; Marshall, 2010).

Figure 2:
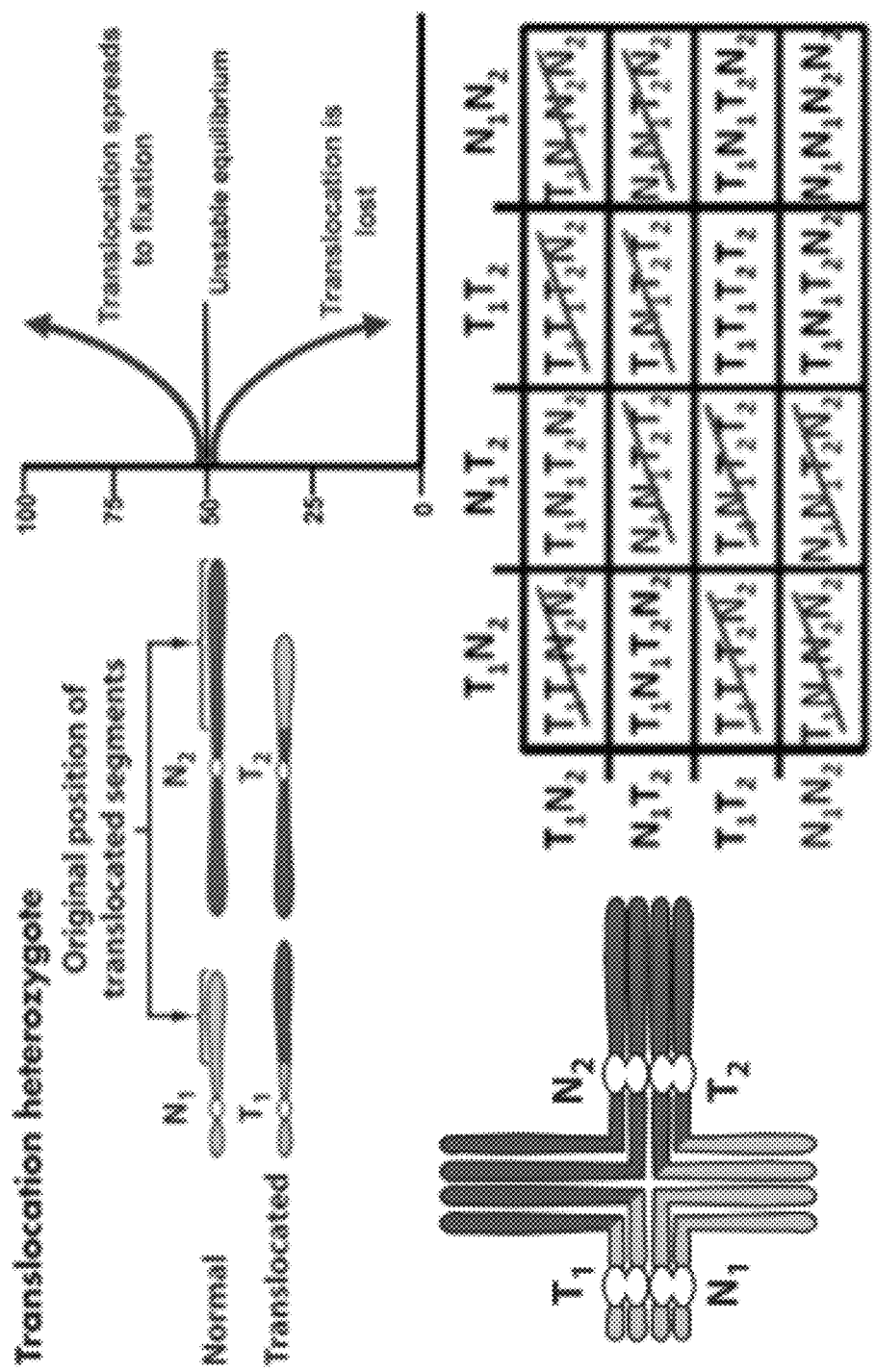
FIG. 2 shows a schematic illustration of chromosomal translocations including pairing during meiosis and fate of progeny.

While synthetic underdominance based systems have been engineered, these systems typically require multiple toxins and antidotes, making them difficult to develop in disease vectors (Akbari et al., 2013). Reciprocal chromosomal translocations, defined as the mutual exchange between terminal segments of two non-homologous chromosomes, are predicted to display underdominant dynamics (Curtis 1968; Marshall and Hay 2012) (FIG. 2). However, this area of research was ultimately abandoned. The reasons for this were at least twofold: first, translocation individuals had lower fitness than their wild type counterparts (Gould and Schliekelman, 2004), in part because they were generated using X-rays or gamma-ray mutagens (Kaiser et al., 1982; Willis et al., 1981) which can reduce robustness, survival, and mating competitiveness, thus reducing the overall fitness of the organism. Second, due to the random nature of the above methods for creating chromosomal rearrangements, it was not possible to link a gene of interest to the translocation breakpoint (reviewed in Gould and Schliekelman, 2004). Finally, more recently it has become clear that the arrangement of chromosomes in the nucleus can have large effects on gene expression, which may alter organismal fitness {Harewood, 2010 #5754} {Harewood, 2014 #5755}. Thus, while evidence from evolution tells us that translocations and other genome rearrangements can, on occasion, over geological time, replace other versions of chromosomes in a population, these events may have nothing to do with fitness. They may result from stochastic effects associated with small populations and local extinctions. It is in fact remarkable that no human synthesized translocation-bearing chromosomes have been shown to be able to bring about population replacement. These observations call into question the idea that translocation-bearing chromosomes with fitness comparable to wildtype can be generated easily, or at all. Therefore, while underdominance systems have several attractive features, none have been implemented in ways that are straightforwardly portable across species, and that allow for the coupling of the drive vehicle with cargo genes of interest. The results described herein provide the first implementation, in any organism, of a translocation-based gene drive system.

While reciprocal chromosomal translocations have traditionally been developed randomly by using random chromosome-breaking reagents such as X-rays, new techniques capable of engineering translocations with sequence-specific breakpoints have been developed. For example, techniques based on FLP/FRT recombination (Beumer et al., 1998), Cre/loxP recombination (Egli et al., 2004; Yu and Bradley, 2001), or homologous recombination following double-stranded breaks (Egli et al., 2004; Forster et al., 2005; Uemura et al., 2010) can all be used to generate breakpoint-specific translocations. No translocations generated using these methods have been characterized in terms of organismal fitness of carriers.

Genetic Approaches to Controlling Insect Vectors

The inability of current strategies to successfully control insect vector-borne diseases has led to increased interest in disease control methods that involve release of genetically modified mosquitoes refractory to pathogen transmission (Gould et al. 2006; Sinkins and Gould 2006; Marshall and Taylor 2009; Hay et al. 2010). The idea of replacing wild insect populations with those engineered to be incapable of disease transmission was first discussed decades ago (Curtis 1968; Whitten 1971; Foster et al. 1972); however, at that time, such research was limited by lack of genetic manipulation techniques (Gould and Schliekelman 2006). Since then, advances in molecular biology have generated a wealth of new tools for precise genetic manipulation (Groth et al., 2004; Gould and Schliekelman 2006; Ran et at 2013), and a number of genes that confer refractoriness to malaria and dengue have been identified or engineered (de Lara Capurro et al. 2000; Ito et al. 2002; Moreira et al. 2002; Kim et al. 2004; Franz at el. 2006; Riehle et at 2008; Corby-Harris et al. 2010). However, disease refractory genes are not expected to confer a fitness benefit to carrier mosquitoes (Schmid-Hempel 2005; Gould et al. 2006), and a large proportion of a mosquito population must be disease-refractive to achieve meaningful levels of disease control (Boete and Koella 2002). Thus, effective disease control via population replacement is generally thought to require the linkage of disease refractory genes to a mechanism capable of driving them into a wild population (Braig and Yan 2001; James 2005; Gould et al. 2006; Sinkins and Gould 2006).

Several naturally occurring selfish genetic elements, including transposons, meiotic drive, B-chromosomes, homing endonuclease genes (HEGs), Medea elements, and the intracellular bacterium *Wolbachia*, have been proposed as potential gene drive mechanisms (reviewed in Sinkins and Gould 2006), along with approaches relying on linking genes of interest to engineered chromosomes, such as translocations or compound chromosomes (Curtis 1968; Gould and Schliekelman 2004). Another approach, known as engineered underdominance, has also been discussed (Davis et al. 2001; Magori and Gould 2006). Some of these strategies, including Medea (Chen et al. 2007), *Wolbachia* (Walker et al. 2011), $UD^{MEL}$, a high threshold gene drive system with features of Medea and underdominance {Akbari, 2013 #4379}, and HEGs (Windbichler et al. 2011), have been shown to have some capacity to drive gene introgression in laboratory populations, and translocations have been used to effect insect population suppression (Asman et al. 1981; Baker 1984). However, a robust mechanism of gene drive capable of spreading chosen disease refractory genes into wild populations has not yet been developed in any disease vector species.

High-Threshold Drive Systems

Some drive systems, like Medea and HEGs, are predicted to have low release thresholds, and therefore be invasive, spreading to high frequency even if initially introduced at very low frequency (Marshall 2009; Marshall and Hay 2011; Deredec et al. 2008). On one hand, this is desirable, since disease-refractory genes must spread to high levels to achieve disease control (Boete and Koella 2002). However, it also comes with regulatory and social concerns, concerns since insects don't respect international borders, and forceful drive systems can spread genetically modified organisms (GMOs) into communities or countries before they've agreed to welcome their introduction (Knols et al. 2007). The Cartagena Protocol (the United Nations' set of regulations governing movement of GMOs) allows countries to decide for themselves whether to allow import of GMOs, and prohibits release of GMOs capable of invasively spreading across borders without prior international agreements (Marshall 2010). Furthermore, people have been shown to prefer that transgene spread be tested in isolated locations before releases occur in their own community (Marshall et al. 2010a; Marshall et al. 2010b), and public distrust of GMOs may be considerable (Alphey et al, 2002; Bohannon 2002; Gould et al, 2006). In light of these regulatory guidelines and societal views, it is generally thought that initial releases of transgenic insects must be confinable to the isolated areas where they are being tested (Marshall and Hay 2012).

Gene drive systems based on the phenomenon of underdominance may offer a way to spread transgenes to high frequencies locally without risk of spread into neighboring populations (Altrock et al. 2010; Marshall and Hay 2012). The simplest form of underdominance, or heterozygote disadvantage, occurs when the average fitness of a heterozygote is lower than that of either parental homozygote (Hartl and Clark 1997). Although a single-allele underdominant scheme may be difficult to engineer (Marshall and Hay 2012), several genetic systems based on the underdominant principle—including chromosome translocations (Curtis 1968), inversions (Foster et al, 1972; Robinson 1975) compound chromosomes (Foster et al. 1972; Gould and Schliekelman 2004), and engineered underdominance (Davis et al. 2001; Magori and Gould 2006; Akbari et al. 2013)—have been proposed (and, in the case of Akbari et al., engineered). These systems all have high introduction thresholds (27%-67%), and act as a bi-stable switch: if the frequency of one allele or chromosome is above a crucial threshold, that allele will spread to fixation at the expense of the other allele, while if it is below the threshold, it will be lost from the population and the other allele type will be fixed (Davis et al, 2001; Sinkins and Gould 2006; Altrock et al, 2010; Altrock et al, 2011).

This type of system is inherently removable, since the frequency of underdominant individuals can be diluted below the critical threshold by the addition of wild types, which in some cases may be preceded by a round of insecticide application to decrease total population numbers. A high threshold gene drive mechanism is also unlikely to spread to high levels in neighboring populations linked to the source population by low levels of migration, as the frequency of underdominant alleles is not likely to reach the needed threshold, and so confined releases are possible (Altrock et al. 2010; Altrock et al, 2011; Marshall 2009; Marshall and Hay 2012). Indeed, some analyses suggest that engineered underdominance is the safest gene drive mechanism in contexts in which transgenic containment in initial field cage experiments is likely to be critical (Marshall 2009), Finally, since underdominant schemes are based on two alleles, and since each allele can be engineered to carry a different disease refractory gene, such systems offer additional insurance against breakdown of the system due to mutation or loss of the disease resistance gene (Sinkins and Gould 2006).

The high threshold required for spread of underdominant mechanisms (as compared with other systems) will necessitate significant releases of transgenic individuals to achieve allele or genotype fixation, and considerable releases of wild types if transgene removal is required. However, necessary release ratios are still appreciably lower than those utilized with many SIT or RIDL programs (Krafsur 1998; Gould and Schiekelman 2004; Alphey et al, 2010), which in the case of the Mediterranean fruit fly involves the release of billions of insects into the wild each week (Mumford 2012). In addition, unlike SIT, underdominant systems are self-perpetuating (Baker 1984; Robinson 1976a), while sterile males must be released on a regular basis. Thus, creation of underdominant systems capable of gene drive would be a valuable addition to the emerging field of using genetically modified insects to control vector-borne diseases.

A potential caveat of underdominance systems is that they can break down after release. Even with utilization of evolutionarily robust shRNA toxins, failure of the system can occur in several ways: the protein or shRNA toxin may mutate and cease to function, which will result in selection against the intact underdominance allele, because the mutant version of the chromosome will always survive; the rescue may also become unlinked from the toxin, which would also cause the drive mechanism to break down for similar reasons; finally, the genes of interest (e.g., disease refractory genes) could become unlinked from the drive mechanism, and any achieved strain replacement would be of no practical use. Since any large-scale insect release is a time and resource-intensive undertaking, it would be desirable to engineer a drive system with very little chance of breakdown, so that future releases to replace or eradicate non-functioning alleles can be minimized.

Translocation-mediated gene drive systems have been proposed as potential mechanisms for spreading disease refractory genes. Such systems are threshold-dependent and thus have certain advantages over other potential gene drive mechanisms, such as localization of gene drive and removability. Proof-of-principle establishment of such drive mechanisms in a well-understood and studied insect, such as *Drosophila melanogaster*, is essential before more applied systems can be developed for less characterized vector species of interest, such as mosquitoes. In some embodiments, the present disclosure details the development of a synthetic biology-inspired translocation-mediated gene drive system in *Drosophila melanogaster* as a proof of concept study that can inform efforts to develop such systems in insect disease vectors. In some embodiments, the present disclosure details our development of an underdominance-like drive mechanism that is inherently robust on evolutionary time scales.

Drive Characteristics

Unlike the underdominant schemes described above, the basis of translocation-mediated gene drive is not lethality of the heterozygotes themselves, but rather death of some of their progeny (FIG. 2). The system is similar to classical underdominance, however, because it functions like a bi-stable switch: translocations either spread to fixation or disappear from the population depending on their initial frequency and associated fitness costs (as compared to wild type).

When the frequency of translocation-bearing individuals (T1/+; T2/+ and T1/T1; T2/T2) is low, they are more likely to mate with wild types (+/+; +/+) than with each other, and many of the translocation chromosomes end up being lost in inviable progeny or grandchildren (ones with an unbalanced chromosome set, such as T1/+; +/+). Wild type chromosomes are lost in these progeny, too, but since wild type individuals are more abundant, they mostly mate with each other, producing more viable wild types (+/+; +/+), and eventually T chromosomes are lost from the population. Conversely, if TT animals are more abundant, they largely mate with each other, producing a high frequency of T1/T1;/T2/T2 offspring, while wild type chromosomes are regularly lost in inviable individuals with unbalanced chromosome sets (such as +/T1; +/+), In this scenario, T alleles become fixed in the population, while + alleles are lost.

For a translocation with no fitness cost, a 50% population frequency represents an unstable equilibrium (Curtis 1968) (FIG. 2); if the translocation's frequency is greater than 50%, it will spread to fixation, and if it's less than 50%, it will disappear from the population (Curtis 1968). Thus, releases of high fitness translocation homozygotes (with fitness ~1) at frequencies above 50% should lead to gene drive, while releases below that threshold should lead to loss of translocation alleles. If there is a fitness cost associated with the translocation, the release frequency will be higher (Curtis 1968).

Conceptual Framework of Reciprocal Chromosomal Translocation

A reciprocal chromosomal translocation is an exchange of chromosome pieces between two non-homologous chromosomes (Foster et al. 1972; Robinson 1976). A balanced translocation simply means that the exchange is even and mutual, with no excess or missing genes. Reciprocal translocations can occur naturally (for example, their incidence is ~1/625 in the general human population; Van Dyke et al, 1983) or can be induced by mutagens (e.g., Lyon et al. 1972).

Figure 1B:
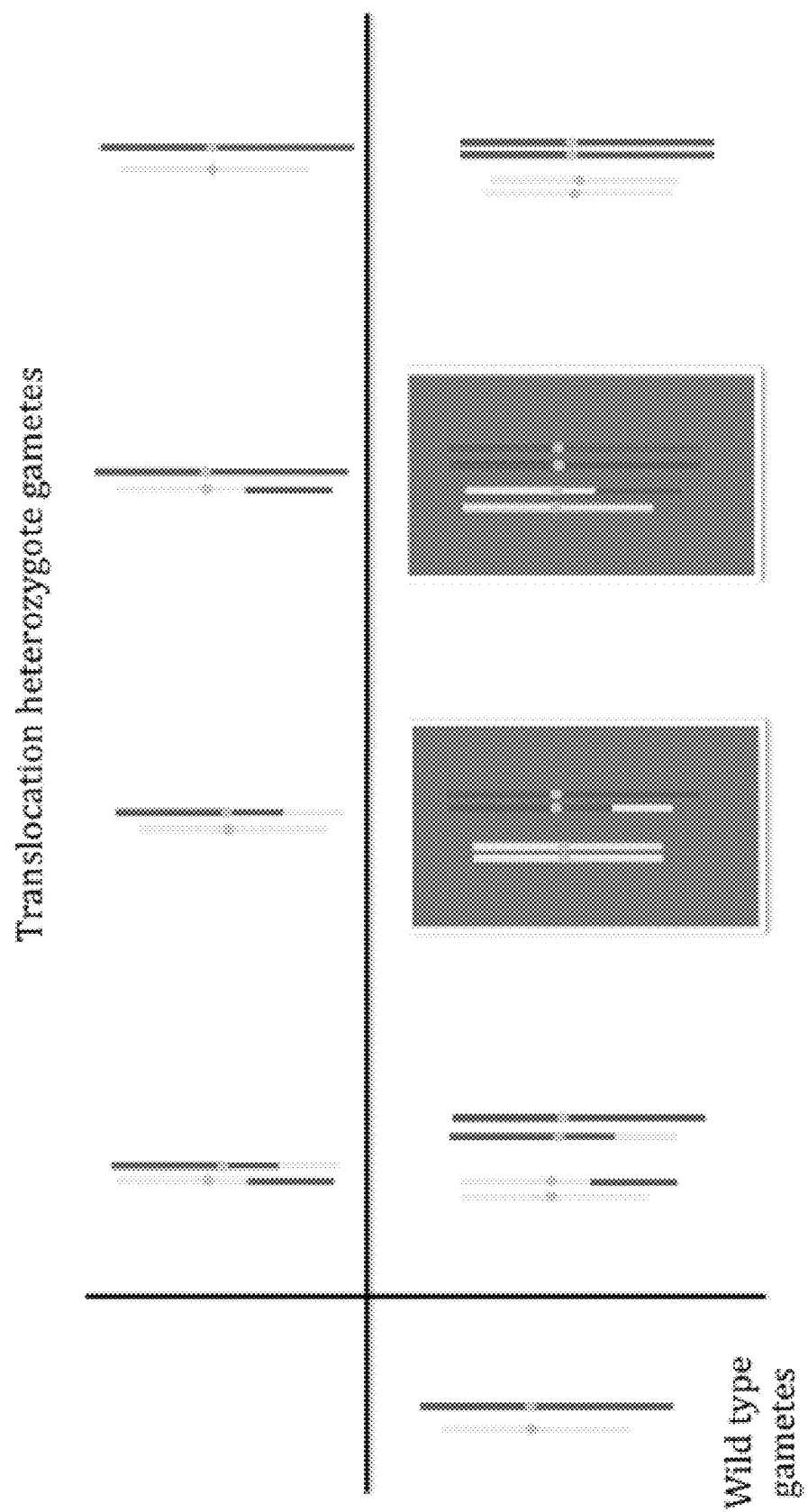

FIG. 1A shows a set of wild type (left), translocation heterozygous (center), and translocation homozygous (right) chromosomes. Although translocation-bearing individuals will have rearranged chromosomes, they will have equal gene copy number and thus be viable. A heterozygote for a reciprocal translocation could theoretically be normal, since it has a balanced chromosome set (FIG. 1A), Of course, translocations that disrupt gene function can impose fitness costs on their carriers). However, when out crossed to wild type, only 50% of the translocation heterozygote's progeny will be viable (FIG. 1B). Thus, when a translocation heterozygote mates with a wild type, 50% of the resulting offspring will be aneuploid and inviable, 25% will be wild type, and 25% will be translocation heterozygotes (FIG. 1B). Thus, 50% of the progeny are inviable, 25% of the progeny are translocation heterozygotes and 25% of the progeny are wild type (FIG. 1B), These calculations assume that the act of translocation, even when it occurs between genes, does not result in more global changes in gene expression that compromise fitness. As discussed above, it is unclear if or when this will be the case.

In some embodiments, this can be visualized as shown in FIG. 1B and FIG. 2. Thus, in some embodiments, if the genotype of a given translocation heterozygote is T1/+; T2/+(where "+" denotes wild type), it will produce four kinds of gametes in equal proportion—(T1,+), (T1, T2), (+,+), and (+,T2). When combined with wild type gametes—(+,+)—only the (T1, T2) and (+,+) will give rise to viable progeny (translocation heterozygotes and wild types, respectively). The other gamete types will perish in progeny that have unbalanced chromosome sets. If the starting translocation individual is homozygous (T1/T1; T2/T2), all first-generation progeny in a wild type outcross will survive, but further mating of these progeny to wild type would result in F2 generation lethality.

The present disclosure provides methods of distributing one or more genes of interest into a population of insects through association with a reciprocal chromosomal translocation. In some embodiments, distributing the one or more genes of interest into a population of insects generates an altered insect population. In some embodiments, translocation-bearing individuals demonstrate a frequency-dependent fitness that provides the altered insect population (those bearing translocations) an ability to increase in frequency as compared with pre-existing wild type insect population (those individuals carrying wildtype or other chromosome forms), over multiple generations when maintained over multiple generations with the wild type population. Thus, in some embodiments, translocation-bearing chromosomes can replace their wildtype counterparts in a wild population, resulting in a population that is said to have undergone population replacement.

In some embodiments, a method of distributing one or more genes of interest into a population of insects is provided. The method comprises providing an insect population. One or more individuals in the insect population comprises a translocation mediated gene drive system. The method further comprises inducing a chromosomal translocation in the one or more individuals in the insect population. The chromosomal translocation generates a translocation-bearing altered insect population, the translocation-bearing altered insect population comprises translocation-bearing individuals that are translocation heterozygotes and translocation-bearing individuals that are translocation homozygotes for the chromosomal translocation, and the translocation-bearing individuals display a fitness that is greater than that of the wildtype (non-translocation-bearing) individuals when challenged in a condition in which a translocation-based drive occurs.

In some embodiments, a translocation mediated gene drive system is provided. The gene drive system comprises a first construct, configured to be positionable at a first insertion site in a first chromosome. The first construct comprises: a) a first location to insert a first gene of interest; b) a first promoter; c) a first fragment of foreign stuffer DNA; d) a second fragment of foreign stuffer DNA; e) a first target site and, in some cases, a second target site for an endonuclease positioned between the first and second fragments of foreign stuffer DNA; f) a first splice acceptor site, positioned downstream from a-e; and g) a first splice donor site, positioned between b and c. The system includes a second construct, configured to be positionable at a second insertion site in a second chromosome. The second construct comprises: h) a second location to insert a second gene of interest; i) a second promoter; j) a third fragment of foreign stuffer DNA, wherein the third fragment is homologous to the second fragment; k) a fourth fragment of foreign stuffer DNA, wherein the fourth fragment is homologous to the first fragment; l) a second target site, in the case where two target sites are used, and a fourth target site, in the case where four cleavage sites are used, for an endonuclease positioned between the third and fourth fragments of foreign stuffer DNA; m) a second splice acceptor site, positioned downstream from h-l, and n) a second splice donor site, positioned between I and j. The first and second chromosomes are non-homologous chromosomes, the first fragment of foreign stuffer DNA is homologous to the fourth fragment of foreign stuffer DNA and the second fragment of foreign stuffer DNA is homologous to the third fragment of foreign stuffer DNA, a double stranded break created at the first, second, third and fourth target sites allows for homologous recombination between the first and fourth fragments, and between the second and third fragments upon a repair of the double stranded break, and wherein the repair of the DSB induces a chromosomal translocation and generates a first translocation chromosome and a second translocation chromosome.

In some embodiments, a population of translocation bearing insects is provided that comprising the system provided herein. In some embodiments, the insects are mosquitos. In some embodiments, the insects are psyllids.

Definitions

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein.

In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive. Unless defined otherwise, technical and scientific terms used herein have the same meaning as commonly understood by one of ordinary skill in the art to which this invention belongs. See, for example Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present invention, the following terms are defined below. It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting.

As used in this specification and claims, the singular forms "a," "an" and "the" include plural references unless the content clearly dictates otherwise.

As used herein, "about" means a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, "regulatory element" refers to nucleic acid elements that can influence the expression of a coding sequence (for example, a gene) in a particular host organism. These terms are used broadly and encompass all elements that promote or regulate transcription, including promoters, core elements required for basic interaction of RNA polymerase and transcription factors, upstream elements, enhancers, and response elements (see, for example, Lewin, "Genes V" (Oxford University Press, Oxford) pages 847-873).

As used herein, the term "insertion site" refers a nucleic acid sequence that allows for insertion of the constructs as provided herein into a genome of a multicellular organism (for example, an insect genome). In some embodiments, a construct as provided herein can comprise a "insertion sequence" that allows for insertion of the construct into a genome of the host organism. Some embodiments that can be employed include the piggybac transposable element, mariner type transposable elements, and the P-element. Also, plasmids can be site specifically integrated into the genome using attb/attp or even by using CRISPR/Cas9, TALEN, MegaTAL and homologous recombination.

In some embodiments, the construct as provided herein comprise a regulatory element. Exemplary regulatory elements in prokaryotes include promoters, operators and ribosome binding sites. Regulatory elements that are used in eukaryotic cells can include, without limitation, transcriptional and translational control sequences, such as promoters, terminators, enhancers, insulators, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell. For example, a promoter is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions (for example, a change in temperature).

In some embodiments, the vector comprises a transformation marker, for example, a fluorescent protein marker such as dsRed (SEQ ID NO: 48 and SEQ ID NO: 49) or GFP (SEQ ID NO: 46 and SEQ ID NO: 47) that can be expressed under the control of suitable regulatory elements. Fluorescent protein can be visualized by illuminating with a suitable excitatory wavelength (for example blue) and observing the fluorescence. Such a marker would allow easy identification of transformants. Other suitable markers for transformation are known in the art of such as EGFP, CFP, ECFP, BFP, EBFP, mHoneydew, mBanana, mOrange, tdTomato, mTangering, mStrawberry, mCherry, mGrape1, mGrape2, mRaspberry, mPlum, YFP or EYFP, and can be chosen by one of skilled in the art according to need.

As used herein, "reciprocal chromosomal translocation" refers to exchange of segments between a first chromosome and a second chromosome. Thus, a first segment of the first chromosome replaces a first segment of the second chromosome, and reciprocally, the first segment of the second chromosome replaces the first segment of the first chromosome. Reciprocal chromosomal translocation between the first and second chromosomes occurs by recombination between homologous regions in the first and second chromosomes. Alternatively, reciprocal chromosomal translocations may occur through direct ligation of the relevant ends of two broken chromosomes, through a process of non-homologous end joining or microhomology-mediated end joining.

As used herein, "homologous recombination" refers to exchange of nucleotide sequences between two identical nucleic acid sequences. Homologous recombination also refers to exchange of nucleotide sequences between two similar nucleic acid sequences. In some embodiments, when the two nucleic acid sequences are similar, a similarity between the two nucleic acid sequences can be about 90% to about 99.9%. In some embodiments, the similarity between the two nucleic acid sequences can be about 90, 91, 92, 93, 94, 95, 96, 97, 98, 99, 99.1, 99.2, 99.3, 99.4, 99.5, 99.6, 99.7, 99.8 or 99.9%.

As used herein, "nucleic acid" refers to deoxyribonucleic acid (DNA). In some embodiments, nucleic acid may refer to ribonucleic acid (RNA).

As used herein, "self-perpetuating" or "self-propagating" refers to perpetuation or propagation without the need for additional external intervention or influence. In some embodiment, self-perpetuating or self-propagating may refer to perpetuation or propagation with a small number of instances of additional external intervention or influence. In some embodiments, a small number can be at most 1, 2, 3, 4 or up to 10.

As provided herein, a "rare-cutting restriction endonuclease" is a restriction enzyme that recognizes and cuts a nucleic acid sequence which occurs rarely or not at all in a genome. For example, I-SceI is rare-cutting endonuclease. It recognizes an 18 base pair sequence, which will occur in a genome with a frequency of 1 in $4^{18}$ base pairs.

It is to be understood that a rare-cutting restriction endonuclease can be, without being limiting, one or more the following: F-EcoT5I, F-EcoT5II, F-EcoT5IV, F-SceI, F-TevI, F-TevII, I-AchMI, I-AniI, I-BasI, I-BmoI, I-Bth0305I, I-BthII, I-BthORFAP, I-CeuI, I-ChuI, I-CpaI, I-CpaII, I-CreI, I-CsmI, I-CvuI, I-DdiI, I-DmoI, I-GpiI, I-GzeI, I-HjeMI, I-HmuI, I-HmuII, I-LlaI, I-LtrI, I-LtrWI, I-MpeMI, I-MsoI, I-NanI, I-NitI, I-NjaI, I-OnuI, I-PakI, I-PanMI, I-PnoMI, I-PogTE7I, I-PorI, I-PpoI, I-ScaI, I-SceI, I-SceII, I-SceIII, I-SceVI, I-SpomI, I-SscMI, I-Ssp6803I, I-TevI, I-TevII, I-TevIII, I-TslI, I-TslWI.AY76, I-Vdi141I, PI-AvaI, PI-BciPI, PI-HvoWI, PI-MleSI, PI-MtuI, PI-PkoI, PI-PkoII, PI-PspI, PI-SceI, PI-TfuI, PI-TfuII, PI-TliI, PI-TliII, PI-TmaI, PI-TmaKI, Cas9, MegaTAL, TALEN.

Methods

In some embodiments, a method of distributing one or more genes of interest into a population of insects is provided. In some embodiments, the method comprises providing an insect population. In some embodiments, one or more individuals in the insect population comprise a reciprocal translocation mediated gene drive system. In some embodiments, the one or more individuals in the insect population comprise an embodiment of a translocation mediated gene drive system as provided herein. In some embodiments, reciprocal translocation is induced in one or more individuals in the insect population.

In some embodiments, a homologous recombination technique is employed for generating translocations as described in Egli et al. 2004. Such an approach can be more efficient than other approaches involving the use of site-specific recombinases such as Cre or FLP. In some embodiments, Cre or FLP can be used. In some embodiments non-homologous end joining, following cleavage at sites on two different chromosomes, can be used, as in {Pacher, 2007 #5756}

In some embodiments, the method involves generating double-strand breaks (DSB) in transgenes on two different chromosomes. The created broken ends i.e. the ends of the chromosomes at the DSB are designed so that they that have homology with each other, facilitating the formation of a translocation chromosome through homology-directed repair. In some embodiments, one or more individuals in the insect population carrying recombinant chromosomes with reciprocal translocations are then identified based on recombination-dependent creation of a visible marker or loss of a visible marker.

In some embodiments the method involves generating double-strand breaks (DSB) in transgenes on two different chromosomes. The created broken ends i.e. the ends of the chromosomes at the DSB are designed so that when direct ligation occurs a dominant marker gene is expressed. In some embodiments, one or more individuals in the insect population carrying recombinant chromosomes with reciprocal translocations are then identified based on ligation-dependent creation of a visible marker or loss of a visible marker.

In some embodiments, the reciprocal chromosomal translocation generates a reciprocal translocation-bearing altered insect population. In some embodiments, the reciprocal translocation-bearing altered population comprises reciprocal translocation heterozygotes and reciprocal translocation homozygotes (FIG. 2).

In some embodiments, the translocation-bearing individuals display a fitness of at least 60% as compared to a wild type when challenged in population cages or other environments. Because translocations, like other forms of under dominance, show frequency-dependent fitness, even translocations that make their carriers significantly less fit than wildtype can spread into a population, if released in high numbers (See, FIG. 7A). As a result, in some embodiments, the reciprocal chromosomal translocation spreads to a high frequency within the wild population. Thus, in some embodiments, the reciprocal translocation-bearing insect population is capable of replacing the wild type population at a rapid rate.

In some embodiments, providing an insect population denotes making available an insect population based on certain needs and/or making available an insect population having certain attributes.

In some embodiments, an insect can be a direct pest or indirect pest. A "direct pest" refers to insects that can cause damage at one or more stage of their life cycle by, for example, eating crops or damaging animals. The New World screw-worm fly Cochliomyia hominivorax, for example, is a direct pest of cattle, and the spotted wing Drosophila, Drosophila suzukii is pest of many fruit crops. An "indirect pest" refers to insects that transmit human diseases, for example, mosquitoes which carry malaria. Indirect pests of organisms other than humans, such as livestock or plants are also known.

In some embodiments, insect refers to, without limitations, one or more of *Drosophila*, mosquitoes, bumblebees, hoverflies, grasshoppers, dragonfly, dancefly, weevil, cricket, wasp, moth, beetles, honey bee, robberfly or butterfly. Additional examples of insects include, but are not limited to, Asian citrus psyllid (diaphorini citriii, Australian sheep blowfly (*Lucilia cuprina*, Asian tiger mosquito (*Aedes albopictus*); Japanese beetle (*Popilla japonica*), White-fringed beetle (*Graphognatus* spp.), Citrus blackfly (*Aleurocanthus woglumi*), Oriental fruit fly (*Dacus dorsalis*), Olive fruit fly (*Dacus oleae*), tropical fruit fly (*Dacus cucurbitae, Dacus zonatus*), Mediterranean fruit fly (*Ceratitis capitata*), Natal fruit fly (*Ceratitis rosa*), Chemy fruit fly (*Rhagoletis cerasi*), Queensland fruit fly (*Bactrocera tryoni*), Caribbean fruit fly (*Anastrepha suspensa*), imported fire ants (*Solenopis richteri, Solenopis invictai*, Gypsy moth (*Lyman tria dispar*), Codling moth (*Cydia pomonella*), Brown tail moth (*Euproctis chrysorrhoea*), yellow fever mosquito (*Aedes aegypti*), malaria mosquitoes (*Anopheles gambiae, Anopheles stephansi*), New world screwworm (*Cochliomyia hominivorax*), Old World Screwworm (*Chrysomya bezziana*), Tsetse fly (*Glossina* spp), Boll weevil (*Anthonomous grandis*), Damsel fly (*Enallagma hageni*), Dragonfly (*Libellula luctuosa*), and rice stem borer (*Tryporyza incertulas*). In some embodiments, the insect either transmits human disease or are agricultural pests. In some embodiments, the insects are wild insect populations.

In some embodiments, the insects are mosquitoes or flies (for example fruit flies). The mosquitoes can be, for example, *Aedes* sp. or *Anopheles* sp. In some embodiments, the mosquito is yellow fever mosquito (*Aedes aegypti*), malaria mosquito (*Anopheles gambiae, Anopheles stephensi*), Asian tiger mosquito (*Aedes albopictus*) or *Culex* mosquitoes. In some embodiments, the insect is one that transmits a disease of a mammal. The disease can be any disease, for example, malaria and/or yellow fever. In some embodiments, the insect is a Spotted wing *Drosophila* (*Drosophila Suzukii*).

In some embodiments, insect refers to an insect that spreads a disease of humans. In some embodiments, insect refers to an insect that spreads a disease of commercially important animals. In some embodiments, insect refers to an insect that spreads a disease of companion animals.

In some embodiments, mosquitoes can be, without limitations, of *Aedes, Anopheles, Culex, Coquillettidia, Haemagogus, Mansonia, Ochlerotatus, Psorophora* or other genera that transmit diseases. In some embodiments, the diseases transmitted by mosquitoes can be one or more of Malaria, Chikungunya, Dog Heartworm, Dengue, Yellow Fever, Eastern Equine Encephalitis, St. Louis Encephalitis, LaCrosse Encephalitis, Western Equine Encephalitis, West Nile Virus, or Zika Virus.

In some embodiments, the insect population has about 10,000 to about 100,000,000,000 insects. In some embodiments, the insect population has about 500, 1000, 1500, 2000, 2500, 3000, 3500, 4000, 4500, 5000, 5500, 6000, 6500, 7000, 7500, 8000, 8500, 9000, 9500, 10,000, 100,000, 500,000, 1,000,000, 100,000,000, 1,000,000,000, 100,000,000,000 or 1,000,000,000,000 insects or within a range defined by any two of the aforementioned values.

Reciprocal Chromosomal Translocation

In some embodiments, inducing a reciprocal chromosomal translocation involves generating double-strand breaks (DSB) on two different chromosomes. In some embodiments, the ends of the chromosomes at the DSB are designed so that they that have homology with each other, facilitating the formation of translocation chromosomes through homology-directed repair. In some embodiments, one or more individuals in the insect population carrying recombinant chromosomes are then identified based on recombination-dependent creation of a visible selection marker. In some embodiments, the visible selection marker can be, without limitations, one or more of GFP (SEQ ID NO: 46 and SEQ ID NO: 47), EGFP, CFP, ECFP, BFP, EBFP, mHoneydew, mBanana, mOrange, tdTomato, mTangering, mStrawberry, mCherry, mGrape1, mGrape2, mRaspberry, mPlum, YFP, EYFP or dsRed (SEQ ID NO: 48 and SEQ ID NO: 49). An embodiment of the adaptation of the reciprocal translocation method is provided below and shown in FIG. 4.

In some embodiments, non-homologous end joining of broken chromosome ends can also, by linking two components of a dominant marker on a single piece of DNA, result in creation of a dominant marker.

Translocation-Bearing Altered Insect Population

In some embodiments, reciprocal translocations result from the mutual exchange between terminal segments of two nonhomologous chromosomes (FIG. 2). In some embodiments, the reciprocal chromosomal translocation generates a translocation-bearing altered insect population. In some embodiments, the translocation-bearing altered population comprises translocation heterozygotes and translocation homozygotes.

In some embodiments, reciprocal translocation is present in about 25% to about 95% of the insects in the population. In some embodiments, reciprocal translocation is present in about 15, 20, 25, 30, 35, 40, 45, 50, 55, 60, 65, 70, 75, 80 or 95% of the insects in the population or within a range defined by any two of the aforementioned values.

The results of mating of wild type (non-translocation-bearing), reciprocal translocation heterozygotes and reciprocal translocation homozygotes with each other are provided in FIG. 2. When translocation heterozygotes mate with each other, there are several patterns of disjunction resulting from independent meiotic assortment. For example, if the two normal chromosomes ($N_1.N_2$) or the reciprocally translocated chromosomes ($T_1.T_2$) segregate together (e.g. $T_1.N_1$; $T_2.N_2$), the meiotic products will be balanced and these progeny will be viable. Conversely, if the disjunction event leads to only one type of translocation chromosome (e.g., $T_1.N_1$; $N_2.N_2$) or too many translocated chromosomes (e.g., $T_1.N_1$; $T_2.T_2$), then the resulting meiotic products will be either aneuploid or orthoploid (duplicated and/or deficient for different chromosomal segments), and consequently the progeny resulting from these meiotic products will be nonviable (FIG. 2).

Therefore, in some embodiments, given that half of the gametes are unbalanced and many combinations of gametes produce unviable offspring, reciprocal chromosomal translocations display underdominant dynamics (FIG. 2).

"Fitness" is defined as the ability of translocation bearing chromosomes to increase or decrease in frequency when introduced at some frequency, in heterozygoous and/or homozygous individuals, into a population of wild types (or an insect population in which no reciprocal translocation has occurred). This ability to spread or to be lost is frequency-dependent, as detailed in (Marshall and Hay 2012). It is understood, therefore, that fitness will vary with frequency of the chromosome type in the population. We define fitness as the fate of a chromosome or chromosome type, when introduced into a population of other types (wildtype), over generations. Low fitness of a translocation (lower than wildtype) is defined as the state of being at a frequency that results in loss of the translocation over subsequent generations, in a challenge experiment, which may occur in the lab, in field cages, or in the wild. Conversely, a translocation is said to have high fitness (higher than wildtype) when translocation-bearing individuals are present at frequencies that result in their spread to higher frequency through the mixed population, over multiple subsequent generations, as compared with the non-translocation-bearing counterpart chromosomes. In some embodiments, fitness is a frequency-dependent ability of different chromosomal types to spread into or be eliminated from a population.

Thus, in some embodiments, when the translocation-bearing individuals display a fitness that is greater than that of the wildtype (non-translocation-bearing) individuals when challenged in a condition, translocation-based drive occurs.

In some embodiments, if the different chromosomal types spread into a population, they display a high fitness. In some embodiments, if the different chromosomal types are eliminated from a population, they display a low fitness.

In some embodiments, a condition or environment in which translocation-based drive occurs can be within, without limitation, population cages, field cages, or open environments.

In some embodiments, a wild type insect population is defined as a population of insects whose chromosomes carry neither heterozygous reciprocal chromosomal translocations nor homozygous reciprocal chromosomal translocations of the type that has been created through the techniques described herein. Thus, in some embodiments, a wild type insect population possesses a normal (wild type) set of chromosomes without the specific chromosomal rearrangements produced by reciprocal chromosomal translocation as provided herein. Wildtype populations may contain at some frequency other chromosome rearrangements, as compared with the canonical wildtype chromosome, By wildtype it is primarily meant that the organism is not carrying the specific translocations being used.

In some embodiments, translocation-bearing individuals display, on average, a fitness greater than that of the average non-translocation-bearing chromosome. This occurs in a frequency-dependent manner, since the fraction of wildtype and translocation-bearing chromosomes that are eliminated each generation is a function of their relative levels in the population, in addition to other traits of carriers such as fertility, longevity, and ability to find food. When it is denoted that translocation-bearing individuals show greater fitness than wildtype it is a functional definition, in which the given frequency of translocation-bearing individuals (translocation-bearing chromosomes) is such that the frequency of the translocation increases in the population, with respect to other chromosome types, over subsequent generations.

Conversely, when it is stated that translocation-bearing individuals show lower fitness than wildtype it means that they are at a frequency such that, over subsequent generations, the frequency of the translocation falls, typically (but not necessarily) to zero. FIG. 7A-FIG. 7D provide examples of these points. It illustrates modeling data in which translocations spread (have high fitness with respect to wildtype) when present at high frequency, but are lost (have ow fitness with respect to wildtype) when present at low frequency. FIG. 8A and FIG. 8B provide examples of actual translocation behavior, for two different translocations, in *Drosophila melanogaster*. Translocations spread when present initially at high frequency (60% or higher), and are lost from the population when present initially in the population at low frequency (40% or lower).

In some embodiments, the increase in frequency of translocations in a population occurs over multiple generations. In some embodiments, the increase in frequency occurs over multiple generations when the reciprocal translocation-bearing individuals are maintained over multiple generations with the wild type population. Thus, in some embodiments, the translocation-bearing chromosomes in the altered insect population are able to increase in frequency as compared to the frequency of wild type chromosomes in the wild type population.

In some embodiments, fitness of translocation-bearing individuals is determined in the context of a population challenge, in which translocation-bearing individuals and wildtypes (or other genotypes) are raised for multiple generations in a common environment, with the frequency of the chromosomes types being determined each generation, or at other time points throughout the experiment. This environment may be a laboratory cage, a field cage, or an open field release In some embodiments, fitness is defined as the population genetic behavior, over multiple generations, of translocation chromosomes in populations consisting of both translocation-bearing individuals and non-translocation-bearing (wild type) individuals.

In some embodiments, a translocation is defined as having a higher fitness than wildtype under conditions that result in translocation-bearing chromosomes increasing in frequency over multiple generations.

In some embodiments, a translocation is defined as having a lower fitness than wildtype under conditions that result in translocation-bearing chromosomes decreasing in frequency over multiple generations.

In some embodiments, it is understood that fitness is frequency dependent, with higher frequencies of a genotype (the translocation or wildtype) generally resulting in an increase in relative fitness with respect to alternative genotypes (wildtype or the translocation).

In some embodiments, if the population of translocation-bearing individuals and the population of wild type individuals are equal in size, then the translocation is less fit and most likely will always fall out of population. The population of translocation-bearing individuals only spreads when translocation makes up a higher fraction of the total population; how high a fraction of the total population the translocation needs to make up depends on how unfit the translocation(s) are. There are two kinds of fitness—intrinsic fitness and population level fitness, and therefore, fitness, as the ability to spread, involves a certain population frequency as well as a certain level of intrinsic fitness, and translocation only spreads when intrinsic fitness is of certain level and the population frequency is high enough for the translocation to spread at that fitness level.

In some embodiments, fitness of translocation-bearing individuals is determined in the context of a population challenge, in which translocation-bearing individuals and wildtypes (or other genotypes) are raised for multiple generations in a common environment, with the frequency of the chromosomes types being determined each generation, or at other time points throughout the experiment.

Environments, such open environments, can include, without limitations, one or more of tropical, wet, monsoon, wet and dry, dry, arid, semi-arid, mild, Mediterranean, humid, humid subtropical, marine, continental, warm summer or cool summer.

In some embodiments, the reciprocal chromosomal translocation can spread to a high frequency within the wild population. In some embodiments, a high frequency may be defined as when translocation-bearing versions of chromosomes make up greater than about 80% of the total chromosomes in a population as compared to wild type or other non-translocation-bearing genotypes. In some embodiments, a low frequency may be defined as when translocation-bearing versions of chromosomes make up about 50% or less of the total chromosomes in a population as compared to wild type versions of the chromosomes involved in generating the translocation. In some embodiments, a medium frequency may be defined as when translocation-bearing versions of chromosomes make up about 70% of the total chromosomes in a population as compared to wild type versions of the chromosomes involved in generating the translocation. In some embodiments, a very high frequency may be defined as when translocation-bearing versions of chromosomes make up greater than about 90% of the total chromosomes in a population as compared to wild type versions of the chromosomes involved in generating the translocation.

In some embodiments, the frequency of translocation-bearing versions of chromosomes can range from a low % to a very high % of the total chromosomes in a population as compared to wild type versions of the chromosomes. In some embodiments, the frequency of translocation-bearing versions of chromosomes can be about 0, 5%, 10%, 20%, 30%, or 40% when the translocation frequency is, or falls below, a critical frequency needed for spread. In populations in which replacement is occurring the frequency can be about 60, 65, 70, 75, 80, 85, 90, 95, 98, 99, or 100% of the total chromosomes in a population as compared to wild type versions of the chromosomes within a range defined by any two of the aforementioned values.

In some embodiments, the translocation-bearing altered insect population is capable of replacing the wild type population. In some embodiments, replacing means replacement of non-translocation-bearing versions of chromosomes involved in the reciprocal translocation, found in the wild population, with individuals carrying translocation-bearing chromosomes. In some embodiments, replacing means replacement of about 80 to about 100% of the wild type population by the translocation-bearing altered insect population. In some embodiments, replacing means replacement of about 80, 81, 82, 83, 84, 85, 86, 87, 88, 89, 90, 91, 92, 93, 94, 95, 96, 97, 98, 99 or 100% or within a range defined by any two of the aforementioned values of the wild type population by the translocation-bearing altered insect population.

In some embodiments, the translocation-bearing altered insect population is capable of replacing the wild type population permanently. In some embodiments, permanently means for all subsequent generations. In some permanently means that in subsequent generations only translocation-bearing individuals are present, and no wild type insect are present. In some embodiments various levels of wildtypes are present, ranging from 0.1% to 40%. This may be due to migration of wildtypes into the target area, or they may arise as progeny of crosses involving heterozygote translocation carriers. In some embodiments, the translocation-bearing altered insect population is capable of replacing the wild type population temporarily. In some embodiments, temporarily means for the 10 generations. In some embodiments, temporarily means for 5 to 20 generations. In some embodiments, temporarily means for 5, 6, 7, 8, 9, 10, 11, 12, 13, 14, 15, 16 17, 18, 19 or 20 generations.

In some embodiments, the translocation-bearing altered insect population is capable of replacing the wild type population at a rapid rate. In some embodiments, rapid rate is defined as replacement of at least 95% of the wild type population by the altered insect population after at most 4 generations.

Figure 7A:
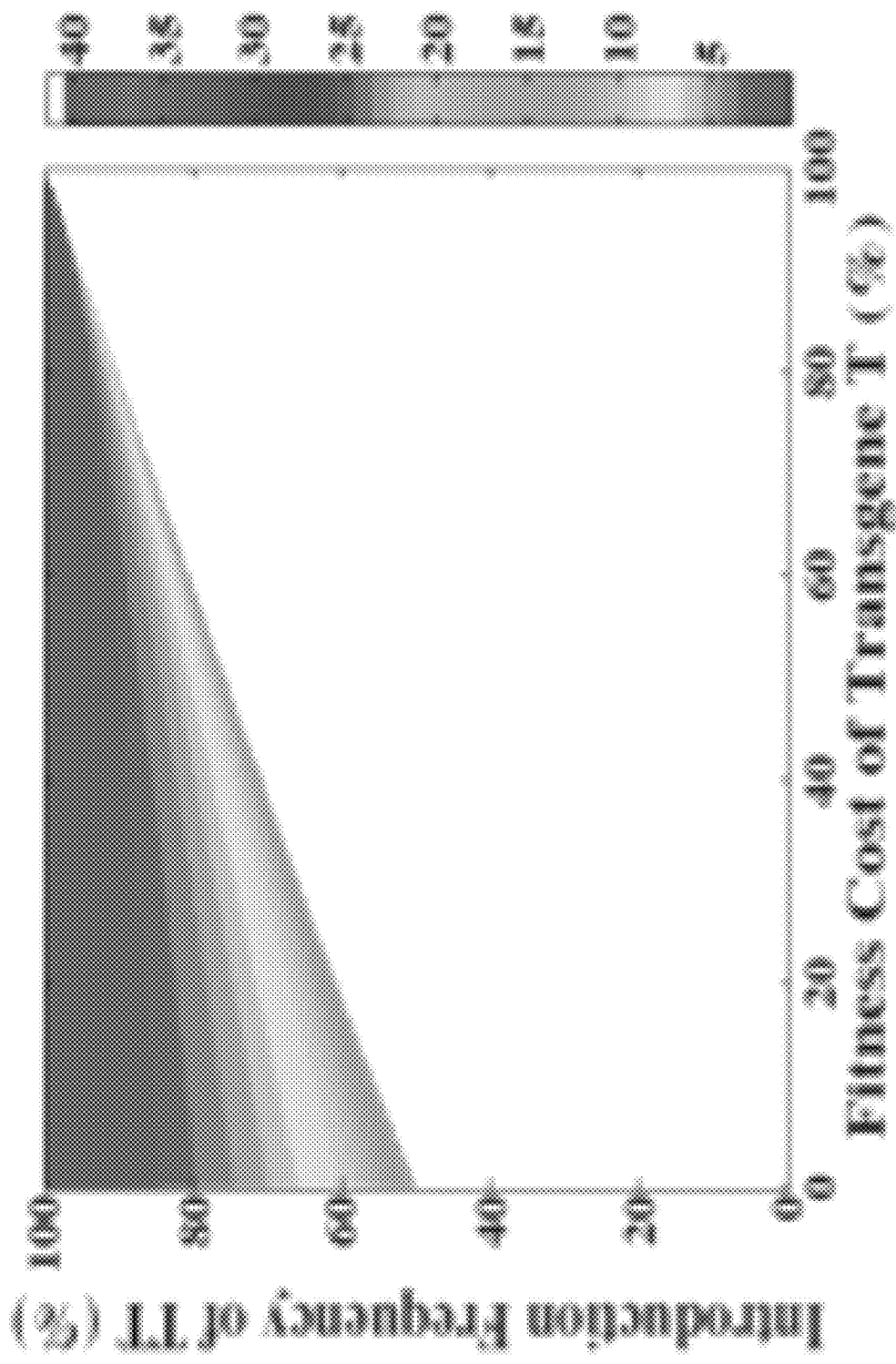
FIG. 7A-FIG. 7D shows a plot illustrating the relationship between fitness cost associated with a reciprocal chromosomal translocation and introduction frequency.
Figure 7B:
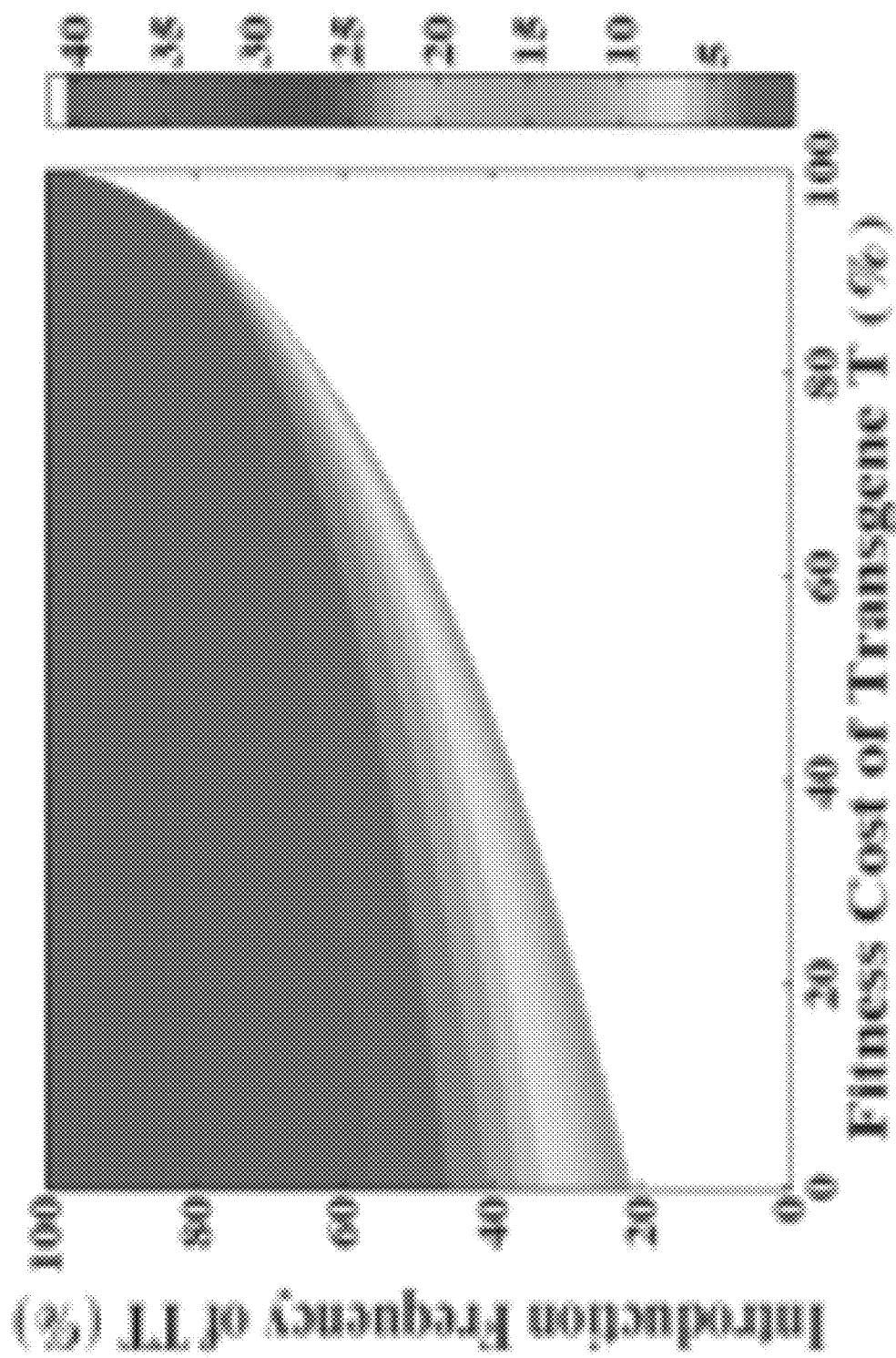

The unstable equilibrium frequency for a translocation with no fitness cost is 50% (FIG. 7A). In some embodiments, translocations with higher fitness costs require higher introduction frequencies (FIG. 7A-D). The introduction frequency will also be dependent on the number of introductions made into the population of interest. In general, as the number of introductions increases, the fraction of individuals that must be transloction-bearing in order for spread to occur, will decrease, as illustrated in FIG. 7B.

Threshold introduction frequency or threshold frequency is the frequency above which a translocation based drive system spreads into a population and below which it is eliminated from the population. For example, the threshold frequency for a translocation-bearing altered insect population with zero fitness cost or zero fitness benefit is 50%.

In some embodiments, translocation chromosomes rapidly spread and replace existing replace populations. In some embodiments, translocations can spread to fixation in a threshold dependent manner as shown in FIG. 8A and FIG. 8B (Example 3). Importantly, in some embodiments, translocations can spread even if they carry a fitness cost. In some embodiments, the fitness cost may be due to the presence of a gene of interest (see below).

In some embodiments, the altered insect population can replace 80% of the target wild type population after 30 generations. In some embodiments, the altered insect population replaces about 60% to about 100% of the target wild type population after about 20 to about 40 generations. In some embodiments, the altered insect population replaces about 60, 65, 70, 75, 80, 85, 90, 91, 92, 93, 94, 95, 96, 97, 98, 99 or 100% of the target wild type population or within a range defined by any two of the aforementioned values after about 20, 22, 24, 26, 28, 30, 32, 34, 36, 38 or 40 generations or within a range defined by any two of the aforementioned values. In some embodiments, the altered insect population replaces about 80-100% of the target wild type population after about 5 to about 40 generations. In some embodiments, the altered insect population replaces about 90-100% of the target wild type population after about 5 to about 40 generations. In some embodiments, the altered insect population replaces about 95-100% of the target wild type population after about 5 to about 40 generations. In some embodiments, the altered insect population replaces about 90% of the target wild type population after about 5 to about 40 generations. In some embodiments, any of these replacement rates can occur when the alter population is at least 50% of the size of the wild type population to be replaced, for example, the altered population can be 60%, 70%, 80%, 90%, 100%, 150%, 200%, 300%, 400%, 500%, or more the size of the wild type population to be replaced.

In some embodiments translocation-based population replacement is reversible. This can be achieved by diluting the replaced population with numbers of wildtypes (non-translocation-bearing individuals) such that the frequency of translocation-bearing individuals falls below the threshold for gene drive. This represents a point, defined functionally, at which the average fitness of translocation-bearing chromosomes has fallen below that of wildtype. These translocations will be lost from the population over subsequent generations.

Genes of Interest

In some embodiments, the one or more gene of interest in the altered insect population encodes for one or more of a disease prevention protein, a disease refractory protein, a protein conferring conditional lethality, an inability to undergo diapause, a protein conferring sterility, a protein conferring conditional inability to fly.

In some embodiments, a disease prevention effector can be one or more of the following: an antibody, a small RNA, other proteins whose expression results in the insect being unable to pick up, replicate, or transmit a pathogen. In other embodiments the disease prevention protein can be a protein or small RNA that is expressed conditionally, resulting in condition-dependent lethality, inability to diapause, or produce progeny. Condition-dependent lethality etc can result in periodic population suppression, which indirectly results in a decrease in disease frequency.

In some embodiments, a disease refractory effector can be one or more of the following: a small RNA, an antibody, a protein that inhibits pathogen binding, entry, replication, or dissemination.

In some embodiments, a protein conferring conditional lethality can be one or more of the following: a toxin protein, a toxin small RNA, a toxin long RNA, wherein by the word toxin is meant any molecule whose expression has the effect of bringing about organismal lethality.

In some embodiments, a protein conferring sterility can be one or more of the following: a toxin protein, a toxin small non-coding RNA, a toxin long non-coding RNA, wherein by the word toxin is meant any molecule whose expression has the effect of bringing about organismal infertility.

In some embodiments, a molecule conferring inability to fly can be one or more of the following: a protein or a small noncoding RNA, a long non-coding RNA.

In some embodiments, diseases can include, without limitations, one or more of Malaria, Chikungunya, Dog Heartworm, Dengue, Yellow Fever, Eastern Equine Encephalitis, St. Louis Encephalitis, LaCrosse Encephalitis, Western Equine Encephalitis, West Nile Virus or Zika Virus. In other embodiments diseases can include those of plants, including citrus greening, which is transmitted to citrus trees by the citrus psyllid diaphorina citrii.

In some embodiments, genes of interest, for example, genes that mediate disease refractoriness are unlikely to confer an overall fitness benefit on insects that carry them (Lambrechts et al., 2008; Schmid-Hempel, 2005; Tripet et al., 2008). Genes that confer condition-dependent lethality, sterility, or inability to fly are similarly unlikely to confer a fitness benefit to carriers. Therefore, an essential component of any population replacement strategy is the presence of a gene drive mechanism that will ensure the spread of linked disease refractory transgenes to genotype or allele fixation in a modest number of generations following release.

Several naturally occurring selfish genetic elements, including transposons, meiotic drive, B-chromosomes, homing endonuclease genes (HEGs), the bacterial CRISPR/Cas system (Esvelt et al., 2014), Medea elements, and the intracellular bacterium *Wolbachia*, have been proposed as potential gene drive mechanisms (reviewed in Sinkins and Gould, 2006), along with approaches relying on linking genes of interest to engineered chromosomes, such as translocations or compound chromosomes (Curtis, 1968; Gould and Schlielcelman, 2004) or engineered underdominance (Davis et al., 2001; Magori and Gould, 2006). Some of these strategies, including Medea (Akbari et al., 2014; Chen et al., 2007) *Wolbachia* (Walker et al. 2011), engineered underdominance (Akbari et al., 2013), HEGs (Windbichler et al., 2011) and recently CRISPR/Cas (Bier, 2015), have been shown to have some capacity to mediate gene introgression in laboratory populations, and translocations have been used to suppress insect populations (Asman et al., 1981).

Figure 3:
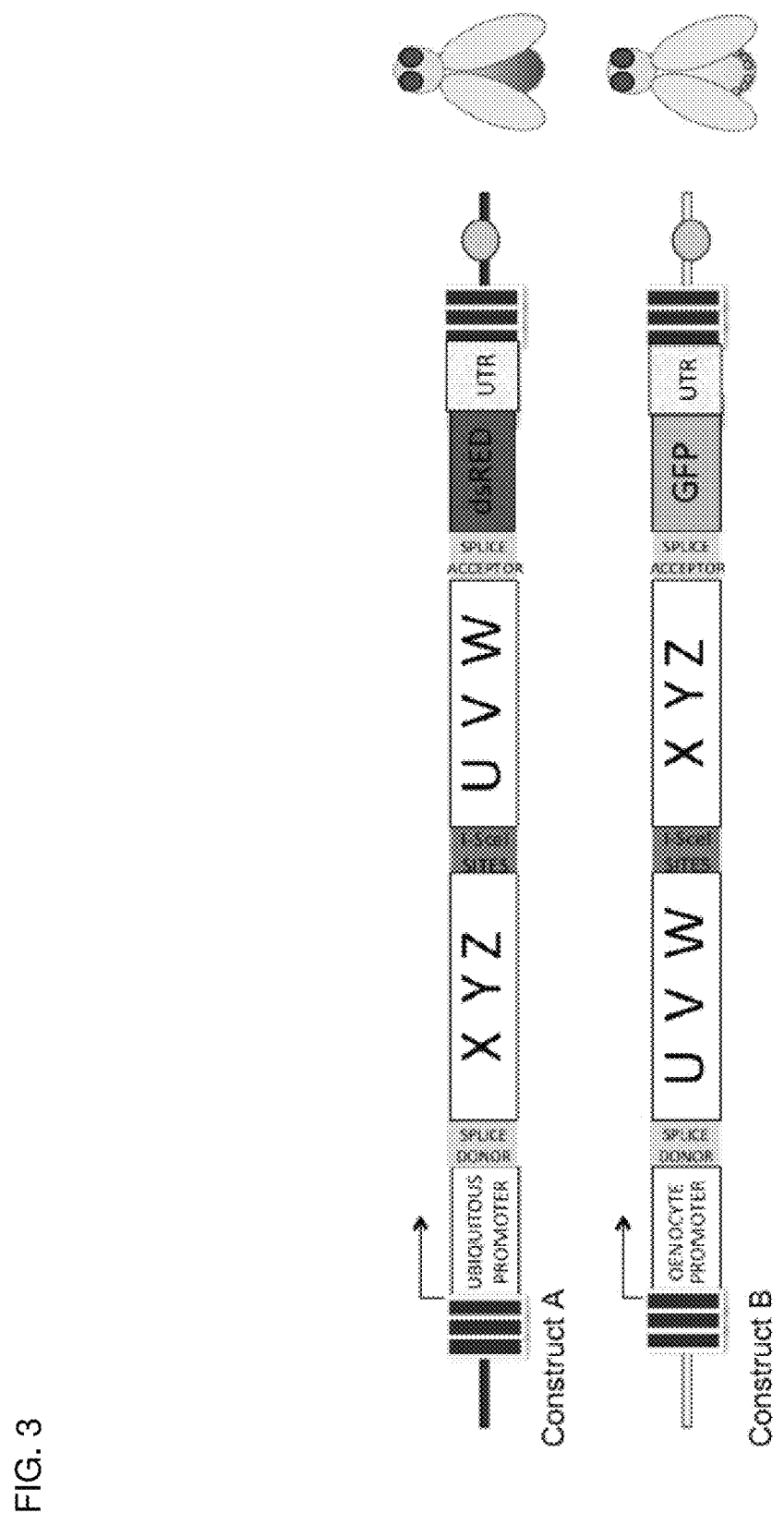
FIG. 3 shows an illustration of general characteristics of two translocation constructs.
Figure 4:
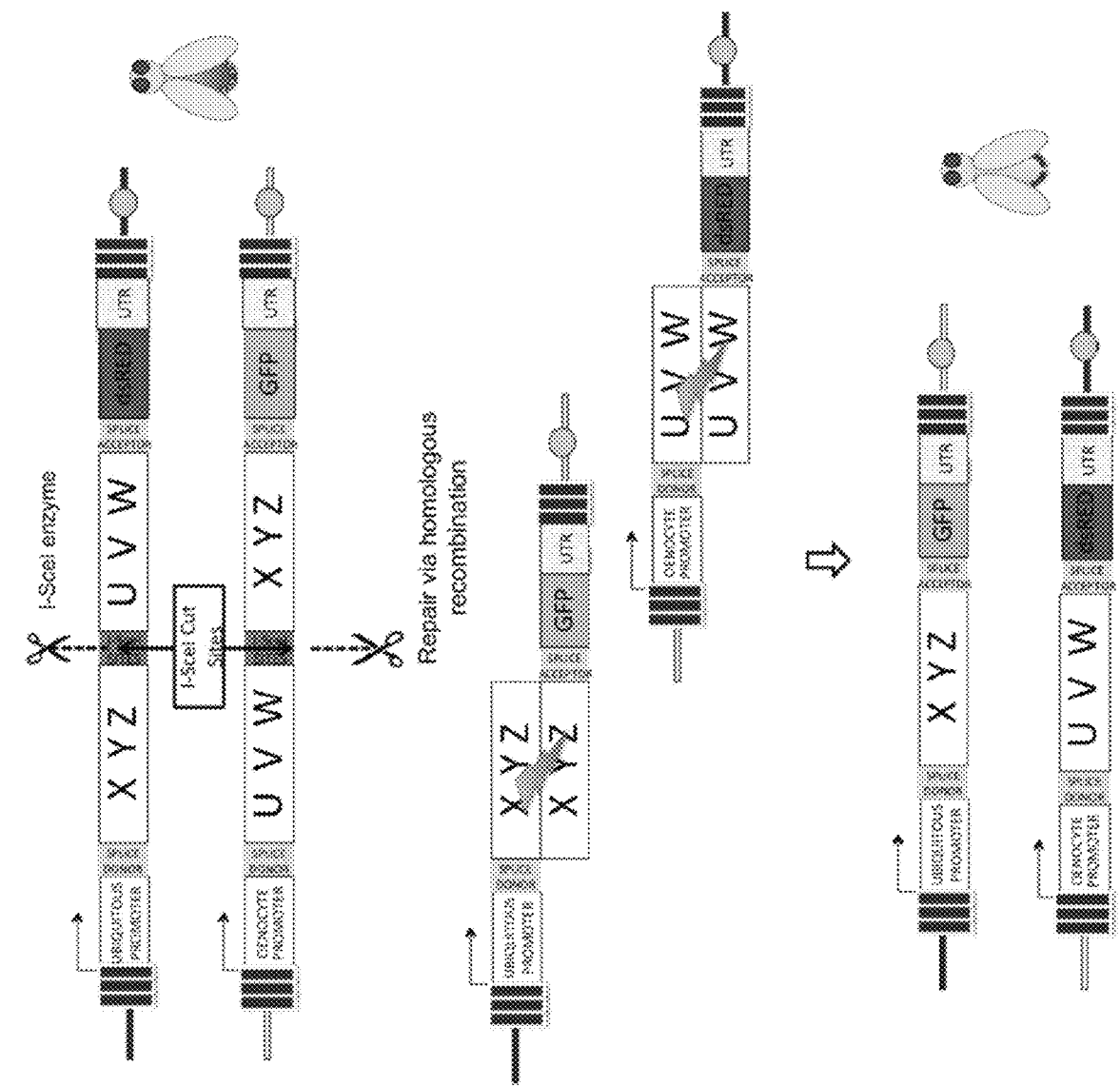
FIG. 4 shows an illustration of an engineered reciprocal translocation.

However, a robust gene drive mechanism capable of spreading chosen disease refractory genes into wild populations has not yet been developed in any vector species. Thus, in some embodiments a gene drive system capable of spreading one or more genes of interest into one or more wild populations is provided Reciprocal Chromosomal Translocation Mediated Gene Drive System In some embodiments, a translocation mediated gene drive system to generate a translocation-bearing altered insect population is provided. FIG. 3 shows an embodiment of the general architecture of the two reciprocal translocation constructs used in some embodiments of a translocation mediated gene drive system provided herein. In some embodiments, the use of the two translocation constructs of FIG. 3 in a translocation mediated gene drive system to generate a translocation-bearing altered insect population is shown in FIG. 4.

Construct Architecture

The basic structure of the two alleles used to generate translocations is shown in FIG. 3. In some embodiments, each allele has a promoter driving a reporter, with an intronic stuffer region of homology (XYZ (for example, and not to be limited to: SEQ ID NO: 42 and for example, and not to be limited to: SEQ ID NO: 43) -UVW (for example, and not to be limited to: SEQ ID NO: 44 and for example, and not to be limited to: SEQ ID NO: 45)) with a restriction site for an endonuclease in the middle. Each allele or construct has a promoter driving a fluorescent and/or selection marker. In some embodiments, Construct A has the ubiquitous baculovirus Opie2 (SEQ ID NO: 34 and SEQ ID NO: 35) promoter driving dsRed (SEQ ID NO: 48 and SEQ ID NO: 49) expression, while Construct B has the oenocyte-specific svp enhancer (SEQ ID NO: 36 and SEQ ID NO: 37) (Gutierrez et al. 2007) driving GFP (SEQ ID NO: 46 and SEQ ID NO: 47). In between each promoter and fluorescent marker is a large intronic stuffer containing a piece of DNA—fragments of the IgG variable sequence and the mouse IgG heavy chain constant region that are foreign to the insect of interest-surrounded by splice donor and acceptor sites. In some embodiments, the stuffer regions are identical between the two constructs, except that their arms are switched sides. The stuffer region is broken up into two fragments of equal length (randomly labeled UVW (for example, and not to be limited to: SEQ ID NO: 44 and for example, and not to be limited to: SEQ ID NO: 45) and XYZ (for example, and not to be limited to: SEQ ID NO: 42 and for example, and not to be limited to: SEQ ID NO: 43), for clarity), and has two sites recognized by the rare-cutting restriction endonuclease positioned in the middle. In some embodiments, the rare-cutting endonuclease is I-SceI. The intronic stuffer is the same in both constructs, except that in Construct A, fragment XYZ (SEQ ID NO: 42 and SEQ ID NO: 43) is on the left and UVW (SEQ ID NO: 44 and SEQ ID NO: 45) is on the right, and in Construct B this order is reversed.

Thus, in some embodiments, a translocation mediated gene drive system is provided, which comprises a first construct (Construct A; FIG. 3), configured to be positionable at a first insertion site in a first chromosome. In some embodiments, the first construct comprises a first location to insert a first gene of interest, a first promoter, a first fragment of foreign stuffer DNA (XYZ (for example, and not to be limited to: SEQ ID NO: 42 and for example, and not to be limited to: SEQ ID NO: 43) in Construct A; FIG. 3), a second fragment of foreign stuffer DNA; (UVW (for example, and not to be limited to: SEQ ID NO: 4 and for example, and not to be limited to: 4 SEQ ID NO: 45) in Construct A; FIG. 3), a first target site for an endonuclease positioned between the first and second fragments of foreign stuffer DNA, and a first splice donor site positioned upstream from the first fragment of foreign stuffer DNA and a first splice acceptor site positioned downstream from the second fragment of foreign stuffer DNA. In some embodiments, a third target site for an endonuclease is positioned between the first and second fragments of foreign stuffer DNA.

In some embodiments, the translocation mediated gene drive system comprises a second construct (Construct B; FIG. 3), configured to be positionable at a second insertion site in a second chromosome. In some embodiments, the second construct comprises a second location to insert a second gene of interest, a second promoter, a third fragment of foreign stuffer DNA (UVW (SEQ ID NO: 44 and SEQ ID NO: 45) in Construct B; FIG. 3), a fourth fragment of foreign stuffer DNA (XYZ (SEQ ID NO: 42 and SEQ ID NO: 43) in Construct B; FIG. 3), a second target site for an endonuclease positioned between the third and fourth fragments of foreign stuffer DNA, and a second splice donor site positioned upstream from the third fragment of foreign stuffer DNA and a second splice acceptor site positioned downstream from the fourth fragment of foreign stuffer DNA. In some embodiments, a fourth target site for an endonuclease is positioned between the first and second fragments of foreign stuffer DNA.

In some embodiments, the second foreign stuffer fragment is homologous to the third foreign stuffer fragment. In some embodiments, the first foreign stuffer fragment is homologous to the fourth foreign stuffer fragment. In some embodiments, the first and second chromosomes are non-homologous chromosomes.

Stuffer DNA

Foreign stuffer DNA is a fragment of DNA that is foreign to the target insect species. In some embodiments, the first construct comprises a first fragment of foreign stuffer DNA. In some embodiments, the size of the first fragment of foreign stuffer DNA is about 50 bp to about 10 kb. In some embodiments, the size of the first fragment of foreign stuffer DNA is about 50, 100, 150, 200, 250, 300, 350, 400, 450, 500, 550, 600, 650, 700, 750, 800, 850, 900, 950 bp, 1, 2, 3, 4, 5, 6, 7, 8, 9 or 10 kb.

In some embodiments, the first construct comprises a second fragment of foreign stuffer DNA. In some embodiments, the size of the second fragment of foreign stuffer DNA is about 50 bp to about 10 kb. In some embodiments, the size of the second fragment of foreign stuffer DNA is about 50, 100, 150, 200, 250, 300, 350, 400, 450, 500, 550, 600, 650, 700, 750, 800, 850, 900, 950 bp, 1, 2, 3, 4, 5, 6, 7, 8, 9 or 10 kb.

In some embodiments, the second construct comprises a third fragment of foreign stuffer DNA. In some embodiments, the size of the third fragment of foreign stuffer DNA is about 50 bp to about 10 kb. In some embodiments, the size of the third fragment of foreign stuffer DNA is about 50, 100, 150, 200, 250, 300, 350, 400, 450, 500, 550, 600, 650, 700, 750, 800, 850, 900, 950 bp, 1, 2, 3, 4, 5, 6, 7, 8, 9 or 10 kb.

In some embodiments, the second construct comprises a fourth fragment of foreign stuffer DNA. In some embodiments, the size of the fourth fragment of foreign stuffer DNA is about 50 bp to about 10 kb. In some embodiments, the size of the fourth fragment of foreign stuffer DNA is about 50, 100, 150, 200, 250, 300, 350, 400, 450, 500, 550, 600, 650, 700, 750, 800, 850, 900, 950 bp, 1, 2, 3, 4, 5, 6, 7, 8, 9 or 10 kb.

Splice Sites

In some embodiments, the first splice donor site and first splice acceptor site in the first construct (Construct A; FIG. 3) can be from any intron as long as the first splice donor and first splice acceptor sites can splice out a fragment of nucleic acid flanked by the first splice donor and first splice acceptor sites. In some embodiments, the second splice donor site and second splice acceptor site in the second construct (Construct B; FIG. 3) can be from any intron as long as the second splice donor and second splice acceptor sites can splice out a fragment of nucleic acid flanked by the second splice donor and second splice acceptor sites.

In some embodiments, the splice sites can be from *Drosophila* Rpl35a gene intron (SEQ ID NO: 30 and SEQ ID NO: 31). In some embodiments, the splice sites can be from *Drosophila* MHC16 gene intron (SEQ ID NO: 32 and SEQ ID NO: 33). In some embodiments splice sites can be derived from any gene in the species of interest, wherein the sequences chosen are able to direct expression of a reporter protein whose function is dependent on splicing. See the examples below for illustrations.

Endonuclease Sites

In some embodiments, at least one target site for an endonuclease is positioned between the first and second foreign stuffer fragments in the first construct. In some embodiments, the number of target sites for an endonuclease positioned between the first and second foreign stuffer fragments in the first construct can be 1 to 4. In some embodiments, the number of target site for an endonuclease in positioned between the first and second foreign stuffer fragments in the first construct can be 1, 2, 3 or 4.

In some embodiments, at least one target site for an endonuclease in positioned between the third and fourth foreign stuffer fragments in the second construct. In some embodiments, the number of target sites for an endonuclease positioned between the third and fourth foreign stuffer fragments in the second construct can be 1 to 4. In some embodiments, the number of target site for an endonuclease in positioned between the third and fourth foreign stuffer fragments in the second construct can be 1, 2, 3 or 4.

In some embodiments, the target site for an endonuclease positioned between the first and second foreign stuffer fragments in the first construct and the third and fourth foreign stuffer fragments in the second construct is a rare and/or a specific endonuclease cleavage site. For example, in some embodiments, the target site can be a cleavage site, without limitations, for one or more of I-SceI, IcreI, Cas9, TALEN or MegaTAL. In some embodiments, the sites should be configured and selected such that they allow the desired fitness in the organism.

Promoters

In some embodiments, the first promoter is a ubiquitous promoter and the second promoter is a non-ubiquitous promoter. In some embodiments, the first promoter is a non-ubiquitous promoter and the second promoter is a ubiquitous promoter. In some embodiments, both first and second promoters are ubiquitous promoters. In some embodiments, both first and second promoters are non-ubiquitous promoters.

As shown in FIG. 3, the red body of the fly with Construct A represents ubiquitous Opie2 (SEQ ID NO: 34 and SEQ ID NO: 35)-driven expression of dsRed (SEQ ID NO: 48 and SEQ ID NO: 49), while the green dots on the torso of the fly bearing Construct B represent svp (SEQ ID NO: 36 and SEQ ID NO: 37)-driven expression of GFP (SEQ ID NO: 46 and SEQ ID NO: 47) in the oenocytes.

Examples, without limitations, of ubiquitous promoters include Opie2 promoter (SEQ ID NO: 34 and SEQ ID NO: 35), Actin5 promoter (SEQ ID NO: 40 and SEQ ID NO: 41). Other ubiquitous promoters can be identified by those with knowledge of the art through examination of transcriptional profiling data from the species of interest, in conjunction with generation of transgenics carrying promoter enhancer fragments linked to a reporter gene such as GFP. Examples, without limitations, of non-ubiquitous promoters include oenocyte-specific SVP enhancer (SEQ ID NO: 36 and SEQ ID NO: 37), *Aedes* Exu promoter. Other promoters with the desired expression pattern can be identified by those with knowledge of the art through examination of transcriptional profiling data from the species of interest, in conjunction with generation of transgenics carrying promoter enhancer fragments linked to a reporter gene such as GFP.

In some embodiments, a third promoter is operably linked to the endonuclease. In some embodiments, the third promoter, without limitations, can be heat shock promoter, (e.g., dmeHS promoter). It can also be any germline-specific or germline predominant promoter. Examples include, but are not limited to, vasa, exu, nanos, zpg. Other promoters with the desired expression pattern can be identified by those with knowledge of the art through examination of transcriptional profiling data from the species of interest, in conjunction with generation of transgenics carrying promoter enhancer fragments linked to a reporter gene such as GFP.

DSB Repair by Homologous Recombination and by Non-Homologous End Joining

In some embodiments, the first and second chromosomes are non-homologous chromosomes. In some embodiments, if both the first construct (Construct A; FIG. 3) and second construct (Construct B; FIG. 3) are introduced into the same fly on non-homologous chromosomes, the animal should have ubiquitous expression of dsRed (SEQ ID NO: 48 and SEQ ID NO: 49) and oenocyte-specific expression of GFP (SEQ ID NO: 46 and SEQ ID NO: 47) (FIG. 4).

In insects without translocation chromosomes, splicing between the splice acceptor site and splice donor site in the first construct brings the ubiquitous promoter in the proximity of a first selection marker (e.g., dsRed (SEQ ID NO: 48 and SEQ ID NO: 49); FIG. 3) thus operably linking the ubiquitous promoter to the first selection marker, and splicing between the splice acceptor site and splice donor site in the second construct brings the non-ubiquitous in the proximity of a second selection marker (e.g., GFP (SEQ ID NO: 46 and SEQ ID NO: 47); FIG. 3) thus operably linking the non-ubiquitous promoter to the second selection marker. Thus, in insects without translocation chromosomes, splicing within the first construct results in ubiquitous expression of dsRed (SEQ ID NO: 48 and SEQ ID NO: 49) and splicing within the second construct results in non-ubiquitous expression of GFP (SEQ ID NO: 46 and SEQ ID NO: 47).

Adding a source of I-SceI should produce double-stranded breaks in both transgenes on both chromosomes. Thus, when a source of I-SceI is introduced, it will cleave in the center on the region of homology, creating a double-stranded break (DSB). Cells seek to quickly repair DSBs, as they pose a threat to the integrity of genetic information, and often do so by finding regions of homology to use as a template, so that the original sequence is preserved (Egli et al. 2004). Thus, in a small percentage of cases, the DSB will be repaired by homologous recombination between stuffer fragments on different chromosomes.

In some embodiments, the first fragment of foreign stuffer DNA is homologous to the fourth fragment of foreign stuffer DNA and the second fragment of foreign stuffer DNA is homologous to the third fragment of foreign stuffer DNA. In some embodiments, a double stranded break (DSB) created in first construct at one or more of the target sites for the endonuclease and a DSB created in second construct at one or more of the target sites for the endonuclease allows for homologous recombination between the first and fourth fragments, and between the second and third fragments upon a repair of the double stranded break.

In some embodiments, the repair of the DSB by homologous recombination induces a reciprocal chromosomal translocation and generates a first translocation chromosome and a second translocation chromosome (FIG. 4). Thus, in some embodiments, I-SceI-induced cleavage will, in a small percentage of cases, lead to recombination between the UVW (e.g., as a non-limiting example: SEQ ID NO: 44 and e.g., as a non-limiting example: SEQ ID NO: 45)-bearing fragments to generate one translocation chromosome, and between the XYZ (e.g., as a non-limiting example: SEQ ID NO: 42 and e.g., as a non-limiting example: SEQ ID NO: 43)-bearing fragments to generate another translocation chromosome (FIG. 4). In some embodiments, the small percentage is about 15% to about 65%. In some embodiments, the small percentage is about 10, 15, 20, 25, 30, 35, 40, 45, 50, 55, 60, 65 or 70% or within a range defined by any two of the aforementioned values.

In some embodiments repair of the DSB occurs through non-homologous end joining, resulting in linkage between fragments of the two chromosome types, resulting in the creation of a translocation, as above. The only difference from the outcomes discussed above is that the DNA fragments present at the joins between the two different chromosomes represent all or part of the DNA sequences lying at the border of the cleavage sites.

Thus, in some embodiments, creation of a translocation can also occur through the repair of the DSB by simple non-homologous end joining of broken DNA ends instead of by homologous recombination.

In *Drosophila*, the sister chromatid and the homologous chromosome are the favored templates for repair (Rong and Golic 2003); however, ectopic sources are also sometimes used, as DSBs are capable of finding repair templates anywhere in the genome (Gong and Golic 2003; Egli et al. 2004). Translocation-bearing individuals can be recognized by virtue of a color switch, since each promoter will now drive a novel reporter: they will have ubiquitous expression of GFP (SEQ ID NO: 46 and SEQ ID NO: 47) and oenocyte-specific expression of dsRed (SEQ ID NO: 48 and SEQ ID NO: 49) (FIG. 4). Thus, following repair of DSB by homologous recombination and generation of translocation chromosomes, flies bearing the translocation chromosomes will now have ubiquitous GFP (SEQ ID NO: 46 and SEQ ID NO: 47) expression and oenocyte-specific dsRed (SEQ ID NO: 48 and SEQ ID NO: 49) expression. Isolated individual translocation heterozygotes can then be crossed out to wild type to generate more translocation heterozygotes, and these can be further crossed to produce homozygous translocation stocks. It will be understood by those with skill in the art that any number of different markers could be used to identify translocation-bearing individuals. A variety of different ways of linking either gain or loss of expression could be used to identify translocation-bearing individuals. These may include gain or loss of a promoter, gain or loss of a coding region, gain or loss of other regulatory region. Intron splicing may or may not be required for these elements to report the occurrence of a translocation.

In insects with translocation chromosomes, in some embodiments. splicing between the splice acceptor site and splice donor site in the first construct now brings the ubiquitous promoter in the proximity of the second selection marker (e.g., GFP (e.g., as a non-limiting example: SEQ ID NO: 46 and e.g., as a non-limiting example: SEQ ID NO: 47); FIG. 4) thus operably linking the ubiquitous promoter to the second selection marker, and splicing between the splice acceptor site and splice donor site in the second construct brings the non-ubiquitous in the proximity of the first selection marker (e.g., dsRed (e.g., as a non-limiting example: SEQ ID NO: 48 and e.g., as a non-limiting example: SEQ ID NO: 49); FIG. 4) thus operably linking the non-ubiquitous promoter to the first selection marker. Thus, in contrast to insects without translocation chromosomes, in insects with translocation chromosomes, splicing within the first construct results in ubiquitous expression of GFP (e.g., as a non-limiting example: SEQ ID NO: 46 and e.g., as a non-limiting example: SEQ ID NO: 47) and splicing within the second construct results in non-ubiquitous expression of dsRed (e.g., as a non-limiting example: SEQ ID NO: 48 and e.g., as a non-limiting example: SEQ ID NO: 49).

In some embodiments, both constructs are flanked by artificial insulators to minimize opportunities for the local genomic environment to influence gene expression within the translocation constructs. In some embodiments, the artificial insulators are CTCF (e.g., as a non-limiting example: SEQ ID NO: 52 and e.g., as a non-limiting example: SEQ ID NO: 53) insulators (FIG. 3; black bars). Thus, in some embodiments, both alleles are flanked by artificial CTCF (e.g., as a non-limiting example: SEQ ID NO: 52 and e.g., as a non-limiting example: SEQ ID NO: 53) insulators (Kyrchanova et al. 2008) to minimize opportunities for the local genomic environment to influence gene expression.

Selection of Insertion Sites

Selecting appropriate genomic insertion sites for the described translocation alleles is crucial, as not all site combinations will permit generation of translocation individuals. Besides producing reliable transformation efficiencies and robust expression levels, selected sites have to meet two criteria: they should be located in gene deserts, and oriented in a specific direction with respect to each other. Ideally, insertion sites will be located as far away from genes as possible so that the translocation event will not disrupt any gene expression or function (if essential gene function is perturbed, translocation-bearing individuals may be unfit or even inviable).

Thus, in some embodiments, the first and second insertion sites are located in a gene desert. In some embodiments, the gene desert has no genes in a region encompassing at least 10 kb in either direction. In some embodiments, the gene desert has no genes in a region encompassing at least 10, 11, 12, 13, 14 or 15 kb in either direction.

In some embodiments, the transgene insertion is located at least 5 kb from a gene. In some embodiments, the transgene insertion is located at least 5, 6, 7, 8, 9 or 10 kb from a gene.

In some embodiments, the first insertion site and second insertion site comprise an insertion site combination. In some embodiments, an insertion site combination can comprise a previously available insertion within the genome such as attP sites, insertion sites for transposons (e.g., piggyBac), cutting sites for endonucleases (e.g., CRISPR, TALEN, MegaTAL). In some embodiments, the insertion site combination can comprise two attP sites 51C and 68E or 51C and 9741 as shown in FIG. 6A. In some embodiments the insertion site will be created by using random integration of DNA into the genome of the organism of interest, using mobile elements such as transposons. In other embodiments insertion sites can be created using homologous recombination to insert a transgene into a specific sequence of the chromosome of interest. This approach is understood by those with skill in the art, as in (Gratz et al, 2015; Chen, H. M. et al 2015).

An embodiment of the system according to the present disclosure comprising the use of two attP sites for generating reciprocal translocation-bearing altered insects is provided in FIG. 6A-FIG. 6E. Example 1, Example 2, Example 5 and Example 6 provide embodiments of systems and methods according to the present disclosure comprising the use of two attP sites for generating reciprocal translocation-bearing altered insects and drive experiments using attP lines with reciprocal translocations. The results of some embodiments of drive experiments involving release of male and female translocation flies at various frequencies are shown in FIG. 8A and FIG. 8B (Example 6). The results of translocation drive experiments using translocation-bearing altered insects generated using the attp site combination 52C-70A2 (9741) are shown in FIG. 8A. The results of translocation drive experiments using translocation-bearing altered insects generated using the attp site combination 52C-68E are shown in FIG. 8B.

Directionality of Insertion

The directionality of insertion of the first and second constructs in the first and second chromosomes is critical for the generation of reciprocal translocation. As far as their directionality, the two translocation alleles or constructs have to be oriented in the same direction (with respect to their centromeres) if they are on the same arms of the (non-homologous) insertion chromosomes. The two translocation alleles or constructs have to be oriented in opposite directions (with respect to their centromeres) if they are on different arms of the (non-homologous) insertion chromosomes.

Figure 5:
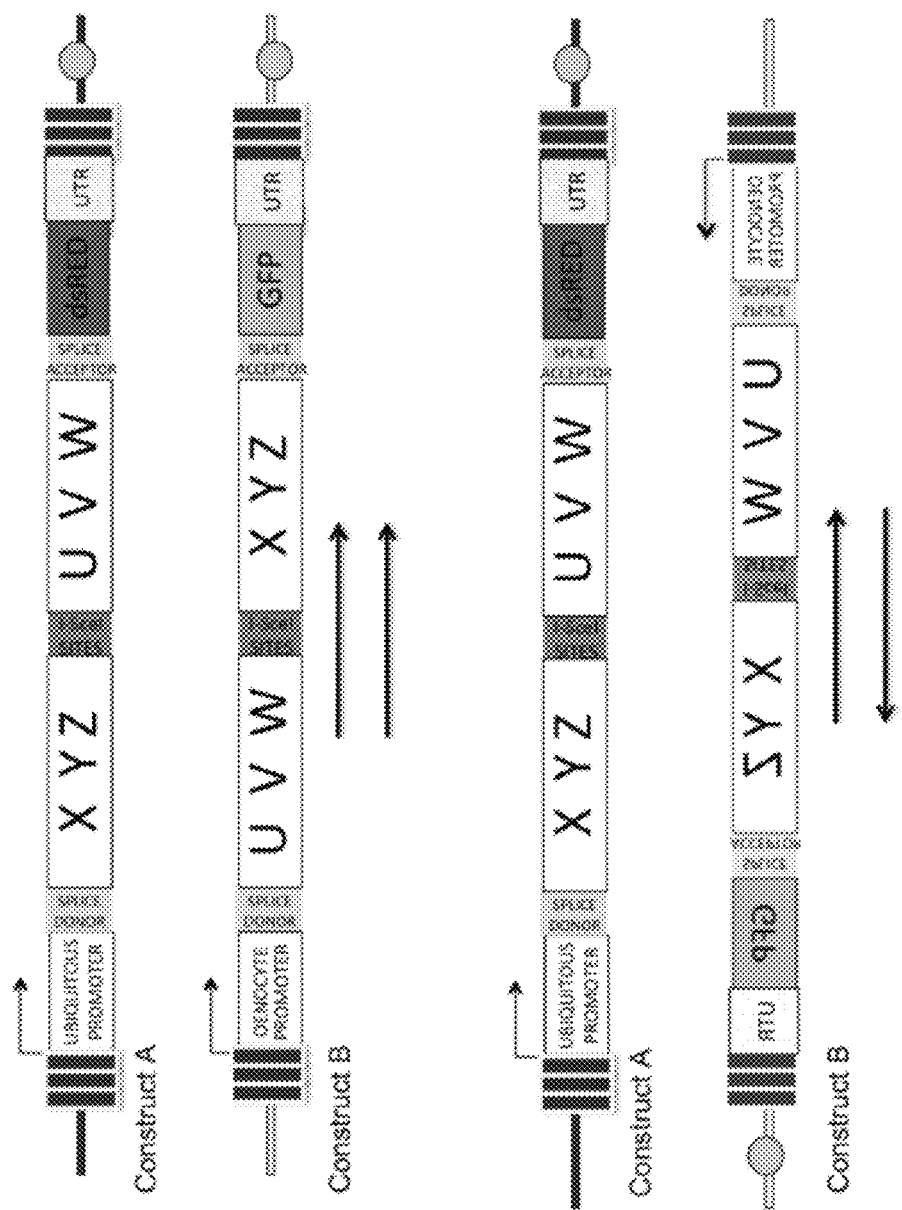
FIG. 5 shows an illustration of the directionality of insertion of translocation constructs.

These construct orientations will allow for the creation of balanced translocations (FIG. 5). In the other two possible orientations, homologous recombination would produce one acentric chromosome and one with two centromeres, both of which would result in the creation of inviable individuals.

Thus, in some embodiments, the first and second constructs inserted in the first and second insertion sites, respectively are oriented in the same direction with respect to the centromere of the first and second chromosomes. In some embodiments, when the first and second constructs are inserted on the same side of centromere, the first and second constructs are in the same orientation. In some embodiments, when the first and second constructs are inserted on opposite sides of centromere, the first and second constructs are in opposite orientations.

In some embodiments, the insertion site combination can comprise two attP sites 51C and 68E or 51C and 70A2 as shown in FIG. 6A. In some embodiments, when the two attp sites are located on different arms of the (non-homologous) insertion chromosomes, the attP sites are oriented in opposite site directions (FIG. 6A). Thus, the insertion of the first and second constructs the two attP sites will result in the two constructs being oriented in opposite directions (with respect to their centromeres).

Self-Perpetuating System

In some embodiments, the system is self-perpetuating/self-propagating. In some embodiments, the system is self-perpetuating/self-propagating when present at a high frequency. In some embodiments, frequency of the system can range from a low % to a very high % relative to wild type versions of the chromosomes. In some embodiments, the frequency of the system can be about 60, 65, 70, 75, 80, 85, 90, 95, 98, 99, 100% or within a range defined by any two of the aforementioned values. In some embodiments, high frequency is defined as at least 85%.

In some embodiments, the system is self-perpetuating/self-propagating after a single release of the altered insect population. In some embodiments, the system is self-perpetuating/self-propagating after multiple releases of the altered insect population. In some embodiments, multiple releases are at most 50. In some embodiments, multiple releases are 2, 3, 4 or 5, 10, 20, 30, 40, 50.

Transferable System

Figure 9:
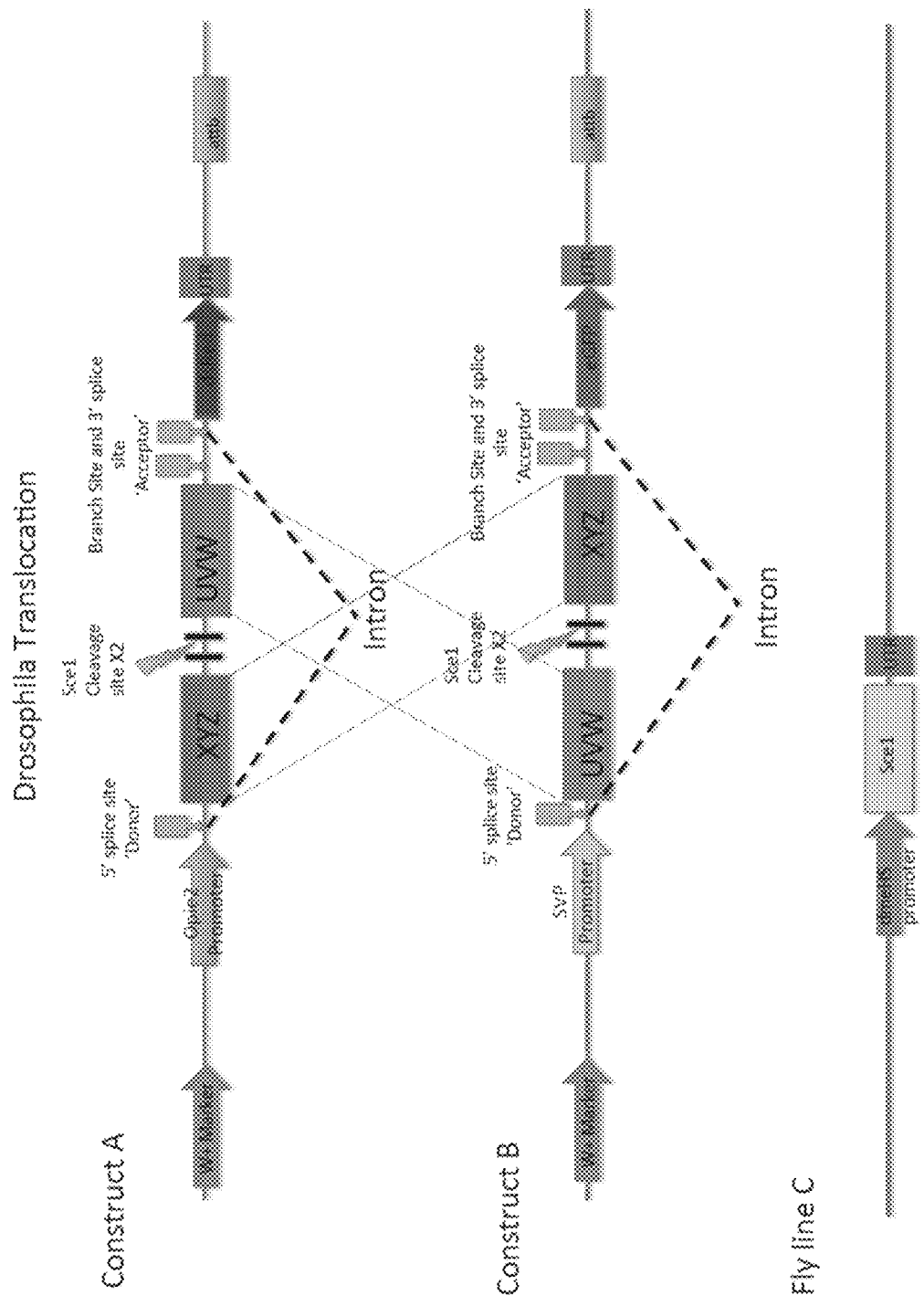
FIG. 9 shows an illustration of an embodiment of reciprocal chromosomal translocation in *Drosophila*.

In some embodiments, the gene drive systems and/or methods for generating reciprocal chromosomal translocations provided herein are adapted for *Drosophila* (Example 8; FIG. 9). However, the embodiments of the gene drive systems and/or methods for generating reciprocal chromosomal translocations provided herein can be transferred by one of ordinary skill in the art to other insects. For examples, the embodiments of the gene drive systems and/or methods for generating reciprocal chromosomal translocations provided herein are transferable by one of ordinary skill in the art without undue experimentation to *Aedes* mosquitoes as provided in Example 9-Example 14.

In some embodiments, Crisper/Cas9 technology, or other site-specific nucleases can be used to generate translocations in *Aedes* based on the system design provided in Example 14. In some embodiments, piggyBac transposons can be used to generate translocations in *Aedes* based on the system design provided in Example 14.

In some embodiments, without limitations, the constructs, insertion sites, promoters, other regulatory regions, splice acceptor and donor sites, stuffer fragments, restriction endonuclease sites, selection markers and artificial insulators provided herein are transferable to other insects. In some embodiments, other insects include, without limitations, one or more of *Drosophila*, mosquitoes, bumblebees, hoverflies, grasshoppers, dragonfly, dancefly, weevil, cricket, wasp, moth, beetles, psyllids, honey bee, robberfly or butterfly.

Elimination of System

In some embodiments, translocations can be confined to one or more local populations (Marshall and Hay, 2012a) (FIG. 7B). Because reciprocal translocations require a high introduction threshold to spread, in some embodiments, they can be removed from a population simply through dilution of the population with non-transgenic individuals carrying a normal chromosome configuration. Thus, in some embodiments, translocation-bearing individuals can be eliminated from a population by introducing a high frequency of wild type individuals. In some embodiments, high frequency of wild type individuals is 70% of the total individuals in the populations. In some embodiments, the frequency can range from about 60% to about 90%. In some embodiments, the frequency can be about 60, 65, 70, 75, 80, 85, 90, 95, 98, 99, or 100%.

In addition, it should be understood that, just as translocations can be introduced into a population through multiple introductions, as discussed above, they can also be eliminated from populations through multiple introductions of wildtypes. In general, as discussed above in the context of population replacement with translocations, the number of individuals in each of the multiple introductions may represent a smaller fraction of the population than if the releases were done as a single release.

Figure 7C:
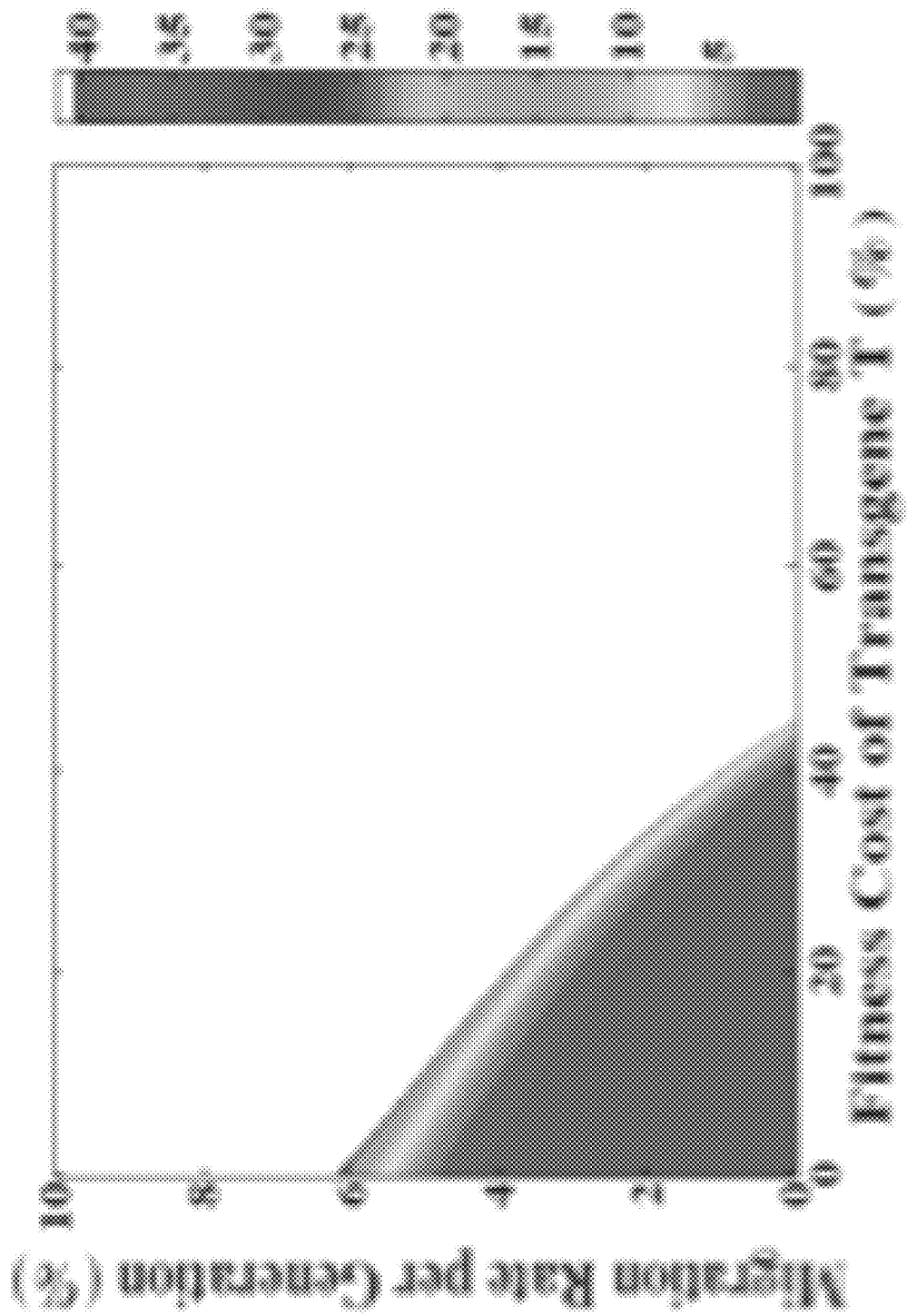
Figure 7D:
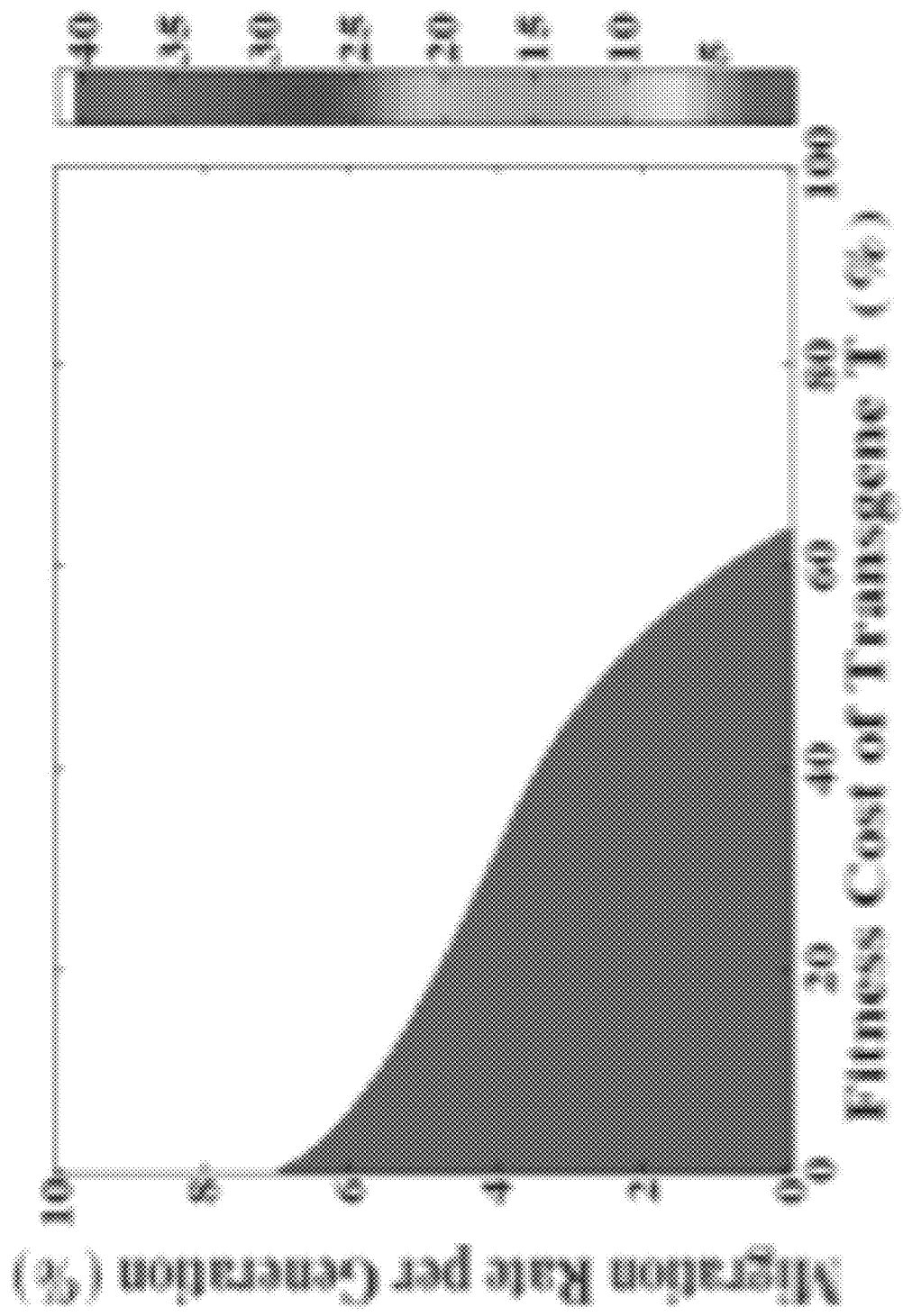
Figure 8A:
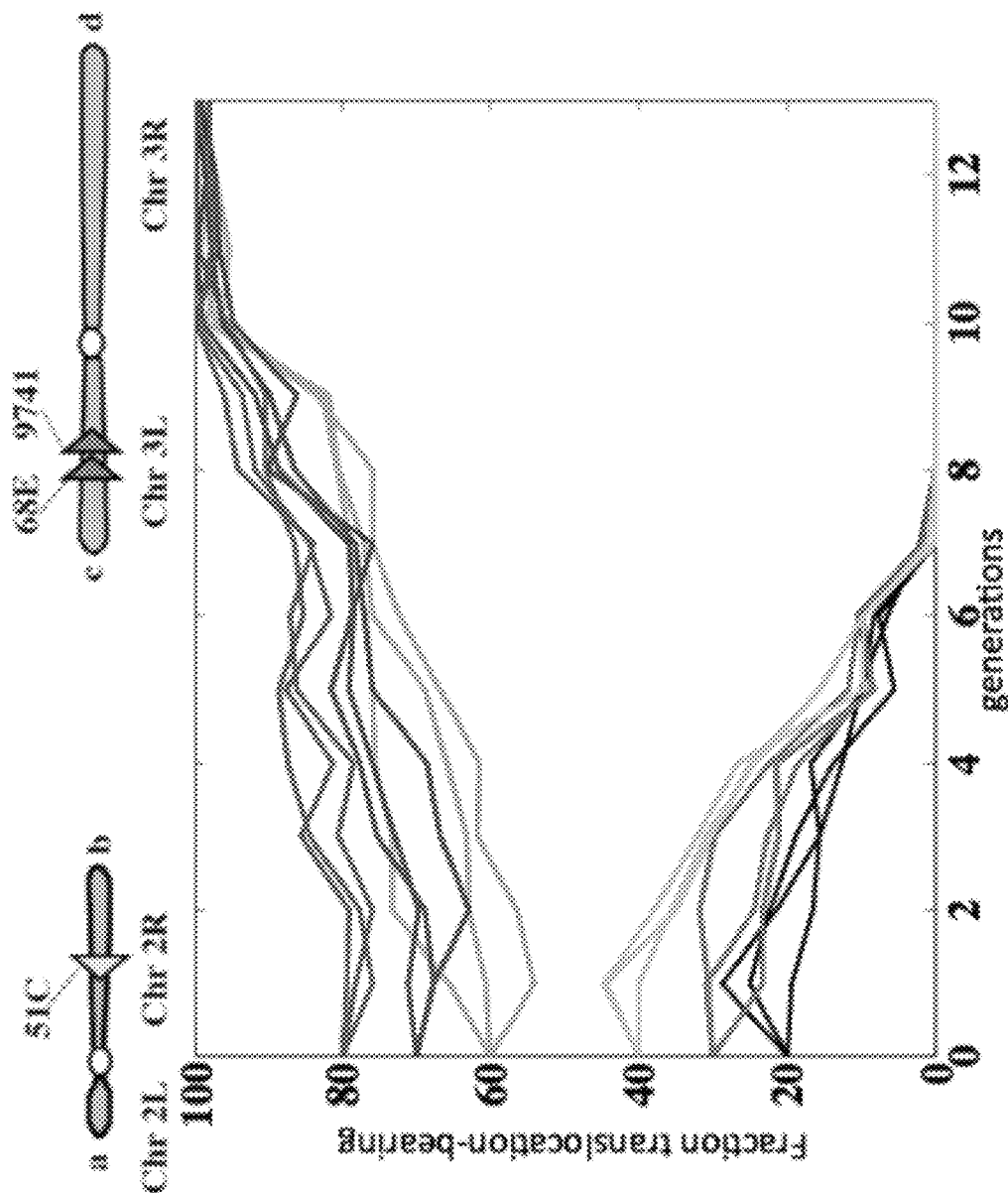
FIG. 8A shows an embodiment of a translocation drive experiment.
Figure 8B:
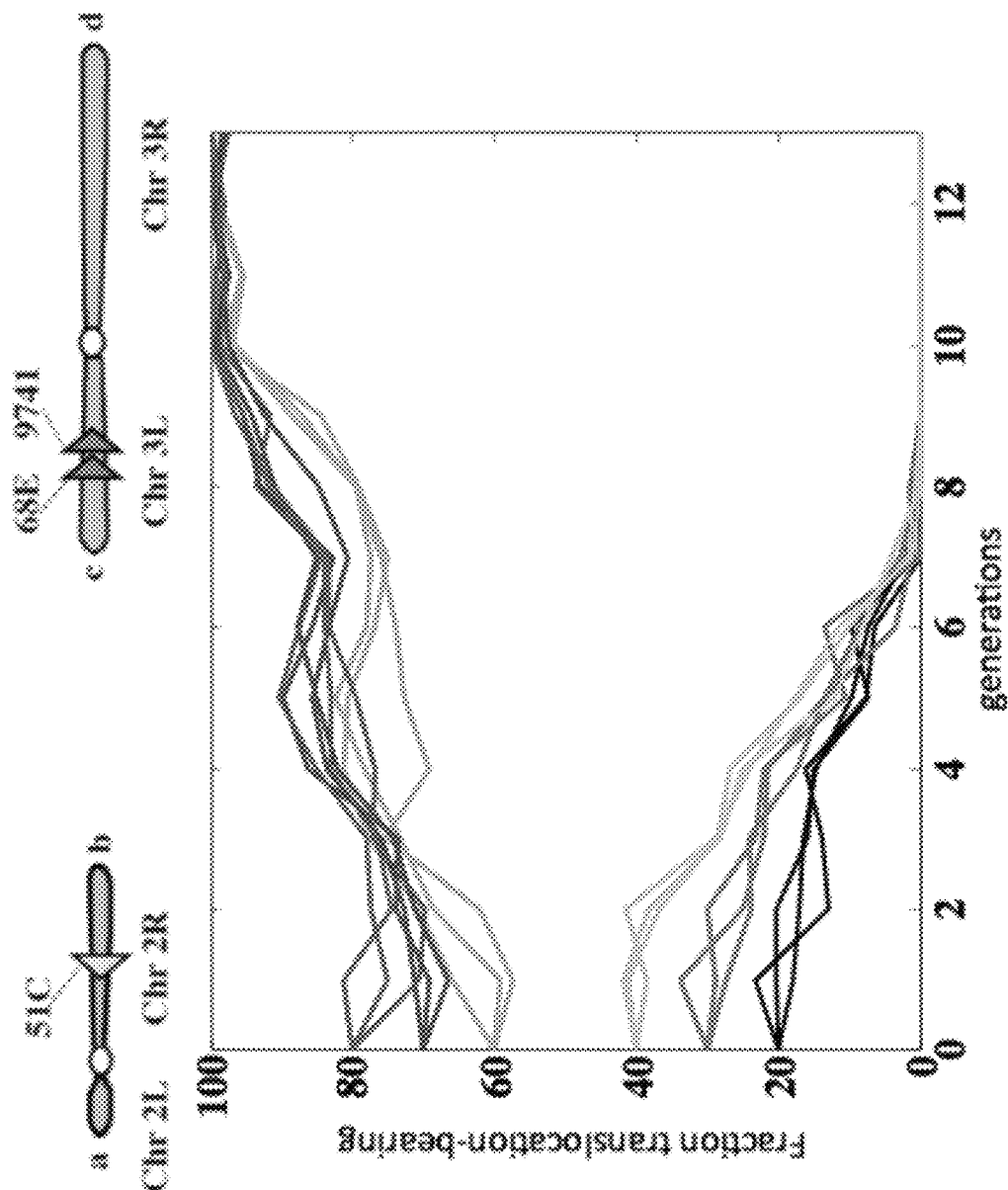
FIG. 8B shows an embodiment of a translocation drive experiment.

For this same reason, in some embodiments, translocation-dependent drive system can also be contained to one or more local environments (FIG. 7B; Example 4). This occurs because the low levels of translocation-bearing individuals into surrounding areas are insufficient to bring the frequency of translocation-bearing individuals above the frequency needed for spread (Marshall and Hay 2012) (FIG. 7C,D). Thus, in some embodiments, the gene drive system of the present disclosure can be maintained at high level in a local population, but not in the surrounding region, wherein by local population we mean a population connected to that into which translocation-bearing individuals are introduced by a frequency of migration of less than 8% per generation.

Advantages

Any of the embodiments of the methods and/or systems provided herein can offer one or more of the advantages provided below. Translocation-mediated gene drive offers several advantages over some other types of gene drive mechanisms.

Firstly, in some embodiments, it is threshold-dependent, which can be of considerable advantage in initial tests of insect population replacement or when public approval of transgenic releases is limited (Marshall, 2010; Marshall and Hay, 2012a), A system with a substantial introduction threshold is easier to confine to targeted release areas—for example, theoretical analyses of translocation containment (Marshall and Hay, 2012a) suggests that even as a translocation with a modest fitness cost spreads to fixation in one population, it would not rise to greater than 4% frequency in a neighboring population given a 1% migration rate. It is also removable, since diluting translocation allele frequency below the release threshold through continued release of wild type individuals will cause the allele to be lost from the population (Marshall and Hay, 2012a). The release threshold for translocations, while high, is still much lower than some of the release frequencies required by sterile insect technique (SIT) (Gould and Schliekelman, 2004; Krafsur, 1998). And, unlike SIT, translocations are self-propagating from generation to generation, while SIT is an inundative approach that must be repeated on a regular basis (Baker, 1984). In short, while the initial costs associated with release of a high threshold gene drive mechanism are greater than those associated with low-threshold gene drive mechanisms (such as, for example, Medea), the increased level of control over population fate and spread are likely to make it attractive in many real world settings.

In some embodiments, another benefit of translocation-dependent drive is its tremendous robustness in the face of mutation. Unlike the "toxin"-"antidote" schemes underlying some proposed gene drive mechanisms, such as Medea, UDMeI, and engineered underdominance, a translocation is itself both the toxin and the antidote, since the presence of one copy results in lethality for some progeny, while the presence of two copies in transhomozygotes guarantees survival of all progeny (FIG. 16; Example 7). Therefore, toxin and rescue functions cannot be unlinked, and so breakdown of the system through mutation of the toxins function to inactivity is not possible, as can happen with other drive mechanisms; and in any case, reversion of the translocation chromosome to its original arrangement is exceedingly improbable. Even if reversion did occur (which would necessarily be in one individual), this chromosome would find itself in a sea of translocation homozygotes and would rapidly be eliminated from the population.

Additionally, in some embodiments, since the cargo gene of interest (GOI) can be inserted at the translocation breakpoints, where meiotic recombination is inhibited (Sherizen et al., 2005), it is not likely to become unlinked from the translocation (the drive mechanism). If extra protections are desired, the translocation (and the cargo gene of interest) can be created so that one of the breakpoints is in an inversion, essentially eliminating the possibility of recombination with a wild type chromosome (Curtis, 1968; Egli et al., 2004). Furthermore, each translocation chromosome can contain a different cargo GOI, and carrying multiple copies of two different transgenes will enhance robustness to mutation and facilitate "combination therapy": individuals would need to inherit four mutant copies of the GOIs in order to have lost all disease refractoriness activity, while the use of two different transgenes targeting different aspects of pathogen biology should decrease the possibility of pathogens becoming resistant to the transgenes being expressed.

Furthermore, in some embodiments, translocation-dependent drive is likely to be more portable across various species, including disease vectors of interest, than some other proposed gene drive systems, such as Medea, UDMel, and engineered underdominance. This is because a translocation-based gene drive system is simple and does not rely on complex components that may not be characterized in many species, such as well-studied tissue-specific promoters or small silencing RNAs. It simply relies on a general feature of the behavior of chromosomes at meiosis in many organisms: the fact that meiotic segregation in a translocation heterozygote creates a high frequency (roughly 50%) of gametes with an unbalanced chromosome complement, consisting of both widltype and translocation-bearing chromosomes (FIG. 1B, FIG. 2). This is noteworthy, as species to species transfer of gene regulatory sequences and other elements of significance to gene drive mechanisms has been fraught with difficulties (Hammond and Nolan, 2014).

Finally, in some embodiments, it may be easier to achieve public acceptance of gene drive based on translocations than with previously discussed mechanisms. The considerable public discomfort with genetically engineered organisms is likely to extend to any planned releases of genetically modified insects, and even those most likely to benefit from disease eradication will likely have concerns and hesitations (Marshall, 2010), A translocation-based approach may be more likely to win general approval as a drive system for several reasons: translocations are a naturally occurring genetic aberration present at significant frequencies in populations of many different organisms; the words "toxin" and "antidote" need not be used; they are species specific with minimal horizontal transfer across species; and finally, they can be removed from the population, restoring the pre-transgenic state, through dilution of the replaced population with wild type males.

EXAMPLES

Figure 6B:
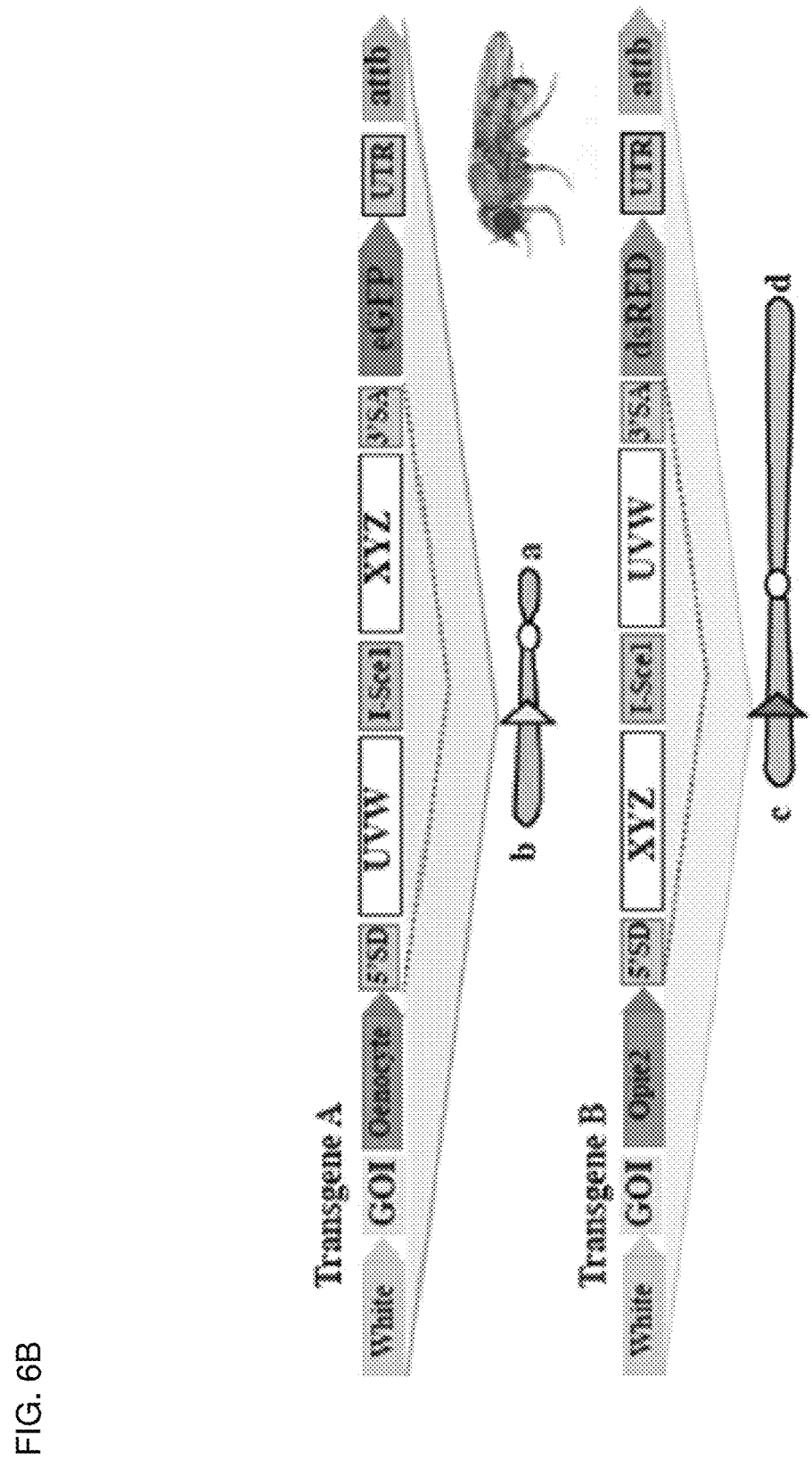
Figure 6C:
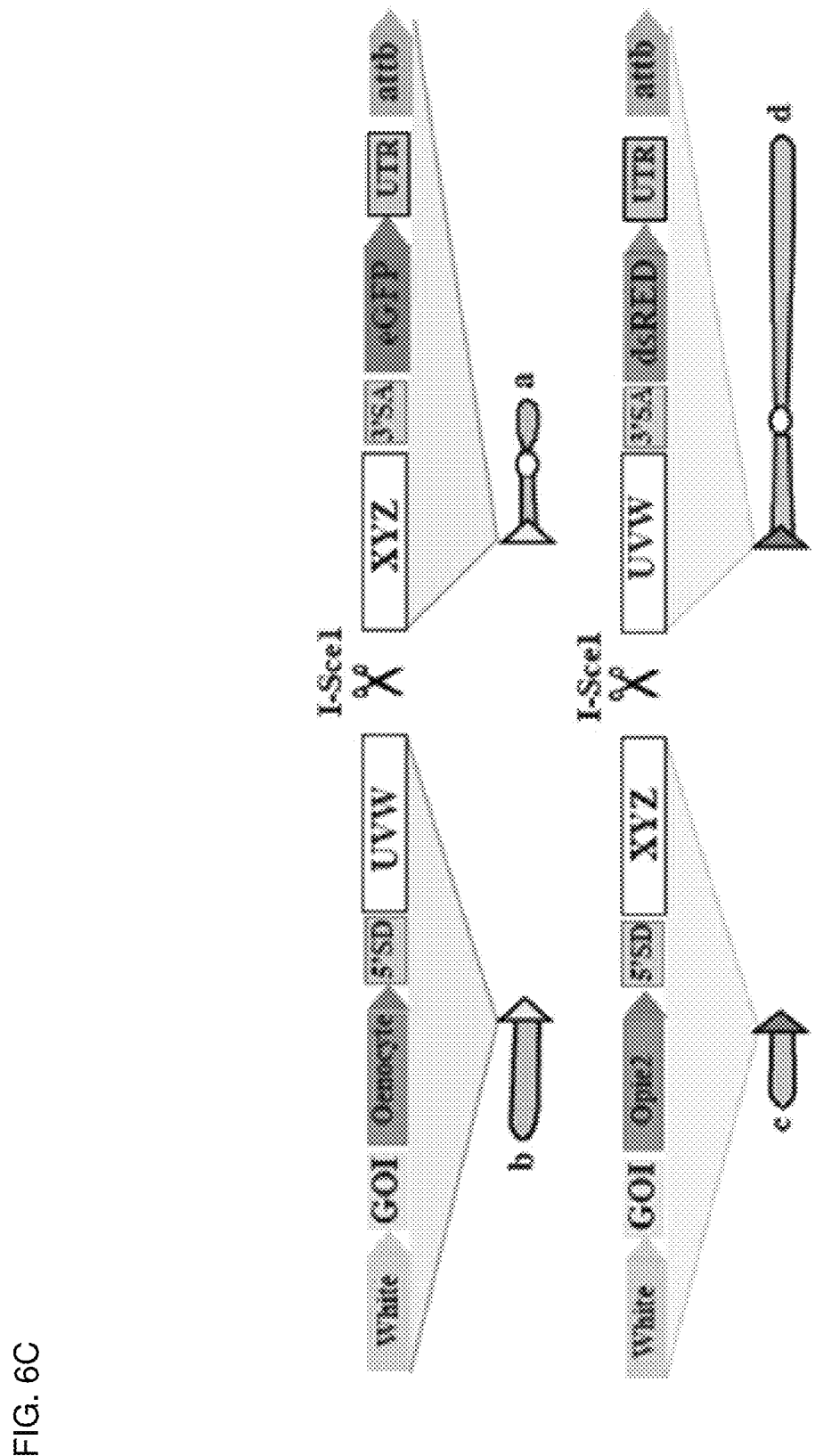
Figure 6D:
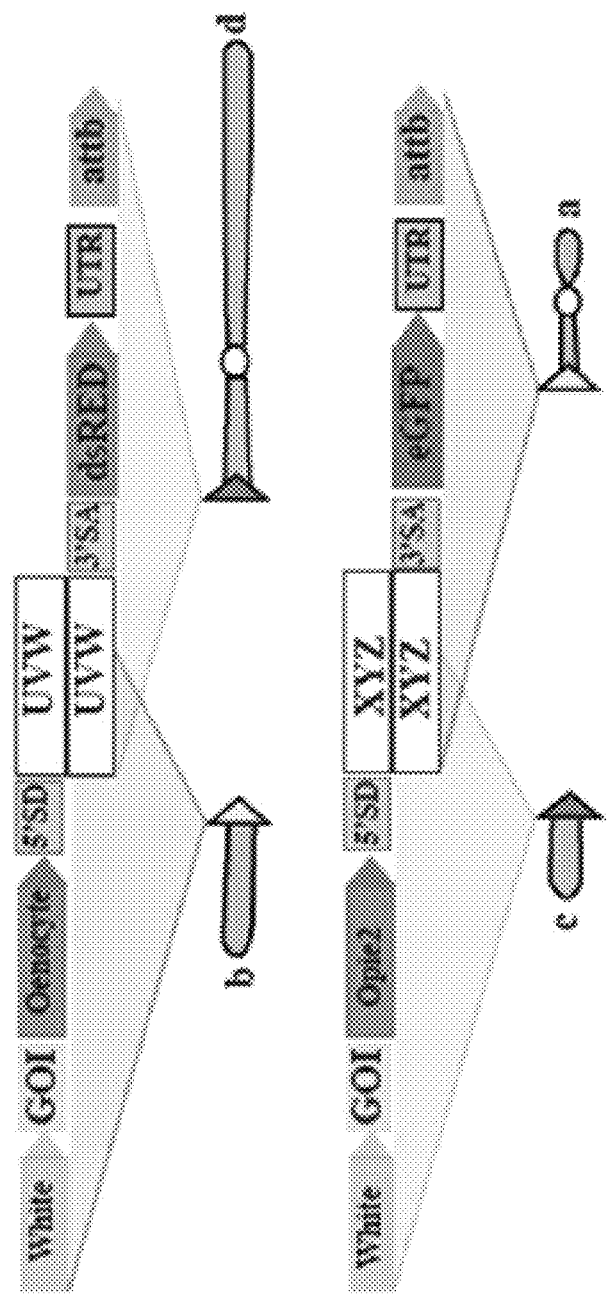
Figure 6E:
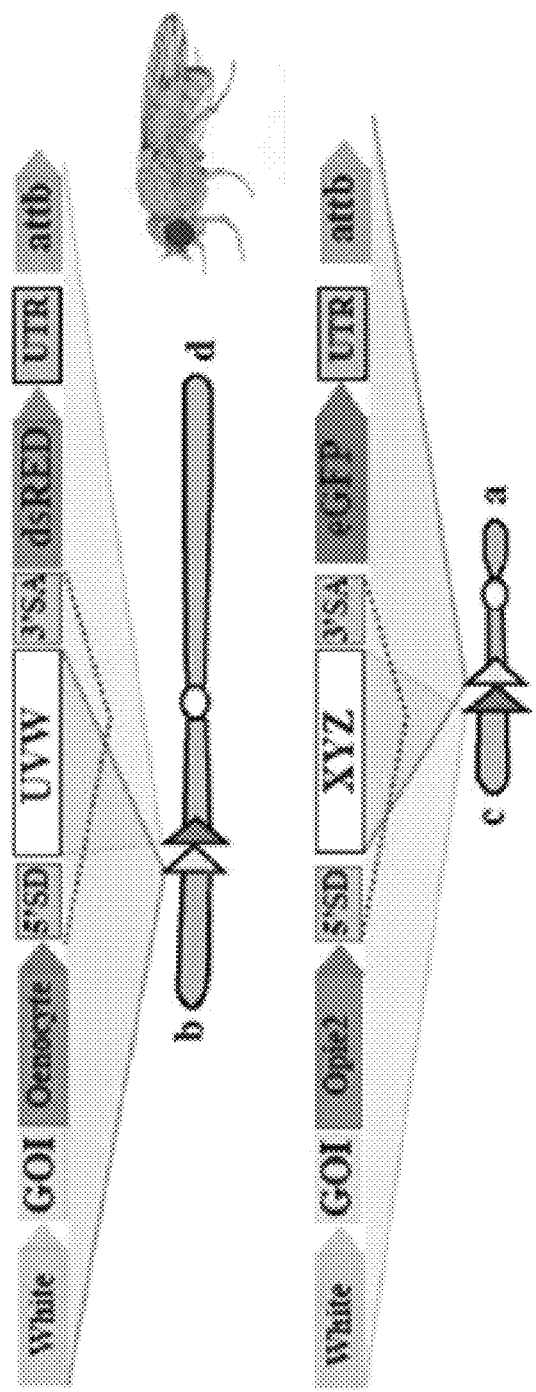

Example 1—Synthetic Biology Approach Used to Generate Reciprocal Chromosomal Translocations The genomic position and orientation of the attP docking sites used to generate translocation-bearing flies are shown in FIG. 6A. Docking sites were used as pairs (51C.68E and 51C.9741 (70A2)), and were selected based on both their non-homologous chromosomal positions and orientations with respect to their chromosomal centromeres. The approach we utilized to generate translocations involves two transgenes, and each transgenic construct contains: a white plus transformation marker; an attB site; a promoter driving a reporter (an oenocyte-specific reporter driving eGFP expression for the top construct, inserted on the second chromosome, and the ubiquitous baculovirus promoter Opie2 (SEQ ID NO: 34 and SEQ ID NO: 35) driving dsRed (SEQ ID NO: 48 and SEQ ID NO: 49) for the bottom construct, inserted on the third chromosome); and an intronic region of homology (either UVW (SEQ ID NO: 44 and SEQ ID NO: 45) -XYZ (SEQ ID NO: 42 and SEQ ID NO: 43) or XYZ (SEQ ID NO: 42 and SEQ ID NO: 43) -UVW (SEQ ID NO: 44 and SEQ ID NO: 45), identical except that their arms are reversed) flanked by a 5' splice donor and 3' splice acceptor, with I-SceI restriction endonuclease sites in the middle (FIG. 6B). When both translocation transgenes are present in the same fly, it will express ubiquitous dsRed (SEQ ID NO: 48 and SEQ ID NO: 49) and oenocyte-specific GFP (SEQ ID NO: 46 and SEQ ID NO: 47). When a germline source of I-SceI is introduced, I-SceI will cleave in the center of the region of homology, creating a doublestranded break (DSB) (FIG. 6C). In a small percentage of cases, the DSB will be repaired during meiosis by homologous recombination between the homology fragments on the non-homologous chromosomes, creating a reciprocal translocation (FIG. 6D). Flies bearing the reciprocal translocation chromosomes are readily detected, as they now have ubiquitous GFP (SEQ ID NO: 46 and SEQ ID NO: 47) and oenocyte-specific dsRed (SEQ ID NO: 48 and SEQ ID NO: 49) expression (FIG. 6E).

Example 2—Site Specific Engineering of Reciprocal Translocations

To site-specifically engineer reciprocal chromosomal translocations, two independent transgenes (FIG. 6A and FIG. 6B) were generated and positioned on non-homologous chromosomes (FIG. 6A and FIG. 6B). Each transgene contained several components, including—reading from left to right—a transformation marker (white gene); a location to insert a gene of interest (GOI) responsible for disease prevention; a promoter Opie2 (SEQ ID NO: 34 and SEQ ID NO: 35) (Theilmann and Stewart, 1992) or oenocyte (Gutierrez et al., 2007); a splice donor site; and two stretches of DNA (annotated as UVW (SEQ ID NO: 44 and SEQ ID NO: 45) and XYZ (SEQ ID NO: 42 and SEQ ID NO: 43)), each roughly 670 bp in length, derived from a species other than the one being targeted, each with a target site for the very rare cutting I-SceI homing endonuclease positioned in the middle. Downstream of these elements, we positioned a splice acceptor, a reporter gene (GFP (SEQ ID NO: 46 and SEQ ID NO: 47) or dsRed (SEQ ID NO: 48 and SEQ ID NO: 49)), and a phiC31 recombination attB site.

These transgenes were introduced into flies independently at three separate attP locations (chromosome 2-51C, chromosome 3-68E and 9741) (FIG. 6A). Importantly, the attP insertion sites were specifically chosen to allow the transgenes to be oriented in the same direction with respect to their centromeres. Furthermore, the transgenes were designed so that flies bearing the transgenes should express the Opie2 (SEQ ID NO: 34 and SEQ ID NO: 35) -driven dsRed (SEQ ID NO: 48 and SEQ ID NO: 49) marker and the oenocyte-driven GFP (SEQ ID NO: 46 and SEQ ID NO: 47) marker via intron splicing (FIG. 6B). The Opie2 (SEQ ID NO: 34 and SEQ ID NO: 35) -driven dsRed (SEQ ID NO: 48 and SEQ ID NO: 49) was readily detectable; however, the oenocyte driven GFP (SEQ ID NO: 46 and SEQ ID NO: 47)

reporter produced no detectable GFP (SEQ ID NO: 46 and SEQ ID NO: 47) signal in the fly oenocytes, presumably due to improper splicing (data not shown).

To induce chromosomal translocations, flies were generated that were trans-heterozygous for each transgene (FIG. 6A and FIG. 6B), and then balancer lines were used to establish stable lines that were double homozygous for both transgenes at chromosomal positions (51C/9741) and (51C/68E), These stable lines were then mated with a fly stock containing a transgene that expressed a rare-cutting homing endonuclease I-SceI upon heat shock (Rong and Golic, 2003), Adult flies containing all three transgenes were repeatedly heat shocked as they were mating and producing eggs, and progeny also received numerous heat shocks during early larval development. Given the construct configuration, I-SceI-induced cleavage resulted in double-stranded breaks in each transgene on both chromosomes (Chr 2 and Chr 3) (FIG. 6C). In a small percentage of cases (roughly ~1/1000), this led to recombination via the endogenous homology-directed repair machinery (FIG. 6D). This repair resulted in the UVW (SEQ ID NO: 44 and SEQ ID NO: 45) -bearing fragments generating one translocation chromosome (b.d), and the XYZ (SEQ ID NO: 42 and SEQ ID NO: 43) -bearing fragments generating another translocation chromosome (c.a) (FIG. 6E).

The translocation-bearing individuals were easily recognized by virtue of a fluorescent color switch, since each promoter was now positioned to drive expression of a different reporter (FIG. 6E). In fact, a number of offspring were found that exhibited Opie2 (SEQ ID NO: 34 and SEQ ID NO: 35) -driven GFP (SEQ ID NO: 46 and SEQ ID NO: 47) expression; however, due to the presumed improper splicing described above, oenocyte-driven dsRed (SEQ ID NO: 48 and SEQ ID NO: 49) expression was not observed. Isolated individual translocation heterozygotes were then mated to wild type flies (WT: +/+; +/+) to generate more translocation heterozygotes, and eventually homozygous translocation stocks were obtained by repeated crossing of heterozygotes. To conclusively confirm the presence of reciprocal translocations, genomic PCRs and subsequent DNA sequencing was performed to verify that each promoter was now associated with a different reporter, and that flies had insertions at both non-homologous attP sites.

Outcrosses of translocation trans-homozygotes showed high levels of embryo survival (ranging from 90.1+/−1.6% to 98.2+/−2.6%). Furthermore, outcrosses of trans-heterozygotes to WT (+/+) showed that roughly half of the resulting embryos perished (ranging from 48.3+/−2.8% to 51.2+/−1.6%), and roughly 50% of the progeny were transgene-bearing (ranging from 48.5+/−3.4% to 49.5+/−2.4%), which would be expected from a translocation heterozygote (FIG. 16; Example 7). Most importantly, no segregation between the white marker and the Opie2 (SEQ ID NO: 34 and SEQ ID NO: 35) -GFP (SEQ ID NO: 46 and SEQ ID NO: 47) marker was observed, indicating the extremely tight linkage between these translocation chromosomes.

Example 3—Engineered Reciprocal Translocations

Engineered reciprocal translocations are predicted to show threshold-dependent gene drive and bring about local population replacement.

A discrete generation, deterministic population frequency model of translocation spread through a single population for varying introduction frequencies and fitness costs for one (FIG. 7A) or three (FIG. 7B) introductions at the specified frequency is illustrated. The heatmap indicates the number of generations required for the translocation to reach fixation (i.e., >99% of the total population) for all combinations of fitness cost and introduction frequency. A variation of this model uses the same framework but incorporates two populations, where translocation-bearing individuals are released into only one population and migration is allowed between the two populations. The heatmap indicates the number of generations required for the translocation to reach fixation in the released population for combinations of all fitness costs and up to a 10% migration rate (per generation) given two (FIG. 7C) or three (FIG. 7D) releases at 50% of the total population.

A plot illustrating the number of generations required for an engineered translocation to be present in >99% of individuals for a reciprocal translocation with different levels of a multiplicative fitness cost is shown in FIG. 7A. Homozygous translocation individual:wildtype individual (both 50 male:50 female) introduction ratios are indicated on the Y axis, and fitness cost on the X axis. Area between lines indicates regions of parameter space within which a specific number of generations (indicated by numbers on the heat map) are required for the frequency of translocation individuals to reach a frequency of 99% or greater. Line color, shown in the heat map at right, provides a rough measure of how many generations are required for the frequency of translocation individuals to reach a frequency of 99% or greater. The red line (40+) indicates that forty or more generations are required. The border between the red-lined region and the lower unlined region defines the critical translocation:wildtype ratio, below which translocation-bearing individuals will be eliminated from the population.

The threshold frequency, above which a translocation based drive system spreads into a population and below which it is eliminated from the population, was calculated using a deterministic model and graphed in FIG. 7A. Introduction ratios of half male-half female homozygous translocation individuals:wildtype individuals are indicated on the Y axis, and the number of generations until fixation or loss of the translocation allele occurs on the X axis. Release thresholds are calculated for elements with a variety of fitness costs. The model assumes an infinite population size, discrete, non-overlapping generations, and random mating. It also assumes a single release.

Example 4—Containment of Translocation-Dependent Drive to Local Environments

Translocation-dependent drive can be contained to local environments. This is illustrated in Marhsall and Hay 2012, for a translocation carrying a 5% fitness cost (s=0.05) introduced into population A. The translocation rapidly spreads to fixation in this population, but, assuming a default migration rate of 1% ($\mu$=0.01), never rises to greater than 4% in population B. More detailed modeling indicates that there is only a very restrictive set of conditions under which translocations fixed in population A can spread to fixation in population B (Marshall and Hay, 2012). Thus, translocations are highly confinable to local environments.

Example 5—Using attP Lines to Generate Translocation Bearing Altered Population

To find suitable insertion sites (insertion site combination), the available attP lines reported to give acceptable transformation rates were surveyed to find ones located in gene deserts. After five potential candidate lines were identified, fly stocks were obtained for each line and extracted genomic DNA so that the orientation of the attP sites (and thus the orientation our constructs would be inserted) could be ascertained. Ultimately, three attP lines were chosen for transformant generation—one with the insertion site on the second chromosome and two with the site on the third chromosome—so that two distinct types of translocation individuals could be produced.

The results of experiments with *Drosophila* are as follows. In the initial set of translocation constructs, 5' and 3' splice sites were utilized from an intron of Rp135a (SEQ ID NO: 30 and SEQ ID NO: 31), as this gene was readily available, it was highly expressed, and the chosen splice sites were empirically predicted to be quite strong. However, transformants for these constructs at all three chosen attP sites showed no visible GFP (SEQ ID NO: 46 and SEQ ID NO: 47) or dsRed (SEQ ID NO: 48 and SEQ ID NO: 49) expression. As previous results for at least one of these had indicated that expression of fluorescent reporters was typically visible, inefficient splicing was suspected as being responsible for lack of marker expression. To verify this, the translocation constructs were tested (with the Actin5 promoter (SEQ ID NO: 40 and SEQ ID NO: 41) replacing the tissue-specific ones) in *Drosophila* S2 cell culture, and found that there was, indeed, no expression of the fluorescent markers. The Rp135a intron (SEQ ID NO: 30 and SEQ ID NO: 31) was replaced with an MHC16 intron (SEQ ID NO: 32 and SEQ ID NO: 33), which was reported to function well in *Drosophila* (Pfeiffer et al. 2010) and which was tested successfully in S2 cell culture, to produce a second generation of translocation constructs.

Transformants bearing the second-generation Opie2 (SEQ ID NO: 34 and SEQ ID NO: 35) -driven dsRed (SEQ ID NO: 48 and SEQ ID NO: 49) translocation allele did show ubiquitous expression of red fluorescence, as expected. However, the svp (SEQ ID NO: 36 and SEQ ID NO: 37) -GFP (SEQ ID NO: 46 and SEQ ID NO: 47) allele still produced no detectable GFP (SEQ ID NO: 46 and SEQ ID NO: 47) signal in the fly oenocytes. It was conjectured that, although the splice sites were now functional, something about the particular orientation of the UVW (SEQ ID NO: 44 and SEQ ID NO: 45) -XYZ (SEQ ID NO: 42 and SEQ ID NO: 43) stuffer fragments in the svp (SEQ ID NO: 36 and SEQ ID NO: 37) construct (since that orientation differed from the orientation in the Opie2 (SEQ ID NO: 34 and SEQ ID NO: 35) construct) still prevented proper splicing. (Our suspicions were later largely confirmed when, during post-IScel cleavage, we found a fly line that expressed both Opie2 (SEQ ID NO: 34 and SEQ ID NO: 35) -dsRed (SEQ ID NO: 48 and SEQ ID NO: 49) and svp (SEQ ID NO: 36 and SEQ ID NO: 37) -GFP (SEQ ID NO: 46 and SEQ ID NO: 47); the cleavage must have led to removal of part or all of the stuffer fragment, which permitted for proper splicing.) Nevertheless, since only one reporter was needed—because in principle, individuals with one translocation chromosome must carry the other one to survive—it was decided to proceed with fly experiments. Transformants bearing each of the translocation alleles were crossed with each other and with a heat shock driven I-SceI line from the Bloomington Stock Center (Bloomington, Ill.) to create a stock with both translocation alleles and a source of ISceI. Adult flies from this stock were then heat shocked repeatedly as they were mating and producing eggs, and progeny received numerous heat shocks during early larval development. These progeny, a number of which had clonal groups of cells that showed the translocation phenotype (i.e., spots of GFP (SEQ ID NO: 46 and SEQ ID NO: 47) expression), were further out crossed to each other, and their offspring were screened for ubiquitous GFP (SEQ ID NO: 46 and SEQ ID NO: 47) expression.

For the first combination of insertion sites, numerous suspected translocation-bearing individuals were identified by Opie2 (SEQ ID NO: 34 and SEQ ID NO: 35) -GFP (SEQ ID NO: 46 and SEQ ID NO: 47) expression (as expected, they did not have svp (SEQ ID NO: 36 and SEQ ID NO: 37) -driven dsRed (SEQ ID NO: 48 and SEQ ID NO: 49) expression, since svp (SEQ ID NO: 36 and SEQ ID NO: 37) -GFP (SEQ ID NO: 46 and SEQ ID NO: 47) was not visible in parent flies). These individuals were first outcrossed to white minus flies for several generations, and then balanced and crossed to each other to generate homozygous translocation individuals. Homozygotes were obtained at expected ratios and appeared quite healthy and robust, and a homozygous stock was established. The type of genomic PCR confirmation that could be used to verify that reciprocal translocations were actually present in these flies was limited: both translocation constructs had large areas of sequence flanking the specific allele components in such a way that PCR amplifying across the entire insertion, or even from a specific promoter to its novel 3' chromosome end, was not possible. However, it was confirmed that each promoter was now associated with a different reporter, and that flies had insertions at both non-homologous attP sites (which wasn't visually clear, since only one of the translocation allele reporters was visible) via PCR. Outcrosses of translocation heterozygotes to white minus also showed that roughly half of the resulting embryos died, which would be expected from a true translocation heterozygote.

For the second combination of sites, numerous Opie2 (SEQ ID NO: 34 and SEQ ID NO: 35) -GFP (SEQ ID NO: 46 and SEQ ID NO: 47) expressing individuals were also found, and the presence of translocation chromosomes confirmed by PCR analysis and heterozygous outcrosses as above. In the interest of time, outcrosses were performed of all of these to balancer lines without carrying out multiple generations of outcrossing to white minus (which was done for the translocation discussed previously), and then to each other to obtain translocation homozygotes.

Example 6—Drive Experiments Using attP Lines with Reciprocal Translocations

Drive experiments were set against wildtype at different introduction ratios. Each line represents a biological replicate in which releases of homozygous male and female translocation individuals occurred at various frequencies (from 30%-80%) (FIG. 8A and FIG. 8B). Each line represents a biological replicate. Translocations show threshold-dependent drive behavior, with those introduced at greater than 50% spreading to high frequency. In contrast, those translocations introduced at low frequency were rapidly eliminated from the population, demonstrating the reversibility of translocation-based gene drive. These low frequency releases can be considered s examples in which a high frequency of wildtypes was introduced into a translocation-bearing replaced population, thereby driving the elimination of translocations from the population.

Example 7—Reciprocal Drive Experiments

Reciprocal translocation flies display expected lethality and viability patterns in embryos and adults (FIG. 16). Crosses between parents of specific genotypes—wild-type (+/+; +/+), translocation heterozygotes (T1/+; T2/+), and translocation homozygotes (T1/T1; T2/T2),—were carried out, and embryo survival (fifth column from right) and percentage of translocation-bearing adults (rightmost column) were independently quantified. The top number in each column shows results for the 51C/68E translocation; the bottom number shows the results for the 51C/9741 (70A2) translocation (FIG. 16).

Example 8—*Drosophila* Translocation

In some embodiments, translocations can be generated in *Drosophila* based on the system design provided in FIG. 9. The baclovirus Opie2 (SEQ ID NO: 34 and SEQ ID NO: 35) promoter in Construct A properly expresses dsRed (SEQ ID NO: 48 and SEQ ID NO: 49) in the absence of recombination and in the presence of recombination expresses eGFP. This is likely due to the fact that this promoter is strongly expressing and works at many places in the genome as tested by me. Construct B does not express the eGFP marker from the SVP promoter (SEQ ID NO: 36 and SEQ ID NO: 37) in the absence of recombination. Also, the SVP promoter (SEQ ID NO: 36 and SEQ ID NO: 37) does not express dsRed (SEQ ID NO: 48 and SEQ ID NO: 49) in the presence of recombination. It is likely that the intron is not being spliced properly. The w+ marker is used to characterize in a w-background and then these transformant lines are balanced on separate chromosomes using balancers. In *Drosophila* this is fine due to the help of balancers, however in *Aedes* this will be challenging. Therefore, each construct should be marked by a unique marker to make genetics possible.

Example 9—*Aedes* Translocation A

Figure 10:
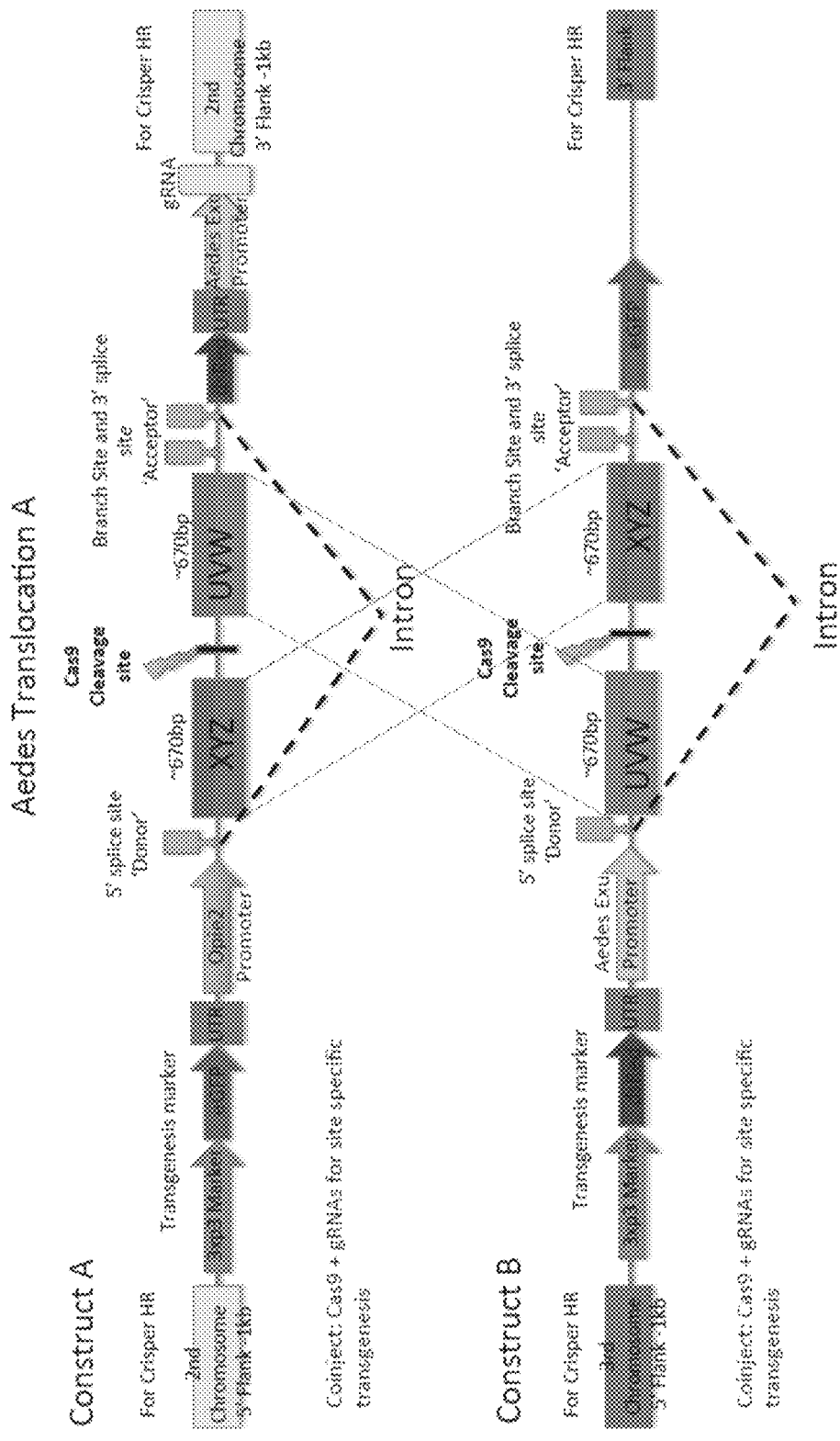
FIG. 10 shows an illustration of an embodiment of reciprocal chromosomal translocation in *Aedes*.

Translocations can be generated in *Aedes* mosquitoes based on the system design provided in FIG. 10. An embodiment of a gene drive system for *Aedes* is provided in FIG. 10. The system comprises a first construct (construct A). The first construct is inserted in chromosome 2. Cas9 nuclease and a first guide RNA are provided for the insertion of the first construct in chromosome 2. The system comprises a second construct (construct B). The second construct is inserted in chromosome 3. Cas9 nuclease and a second guide RNA are provided for the insertion of the second construct in chromosome 3. The first and second constructs have a Cas9 nuclease cutting site. DSBs are generated in the first and second constructs by Cas9 nuclease which cuts at Cas9 cleavage sites in the first and second constructs. A sequence encoding a third guide RNA is provided in the first construct. The third guide RNA directs the Cas9 nuclease to the Cas9 cleavage sites in the first and second constructs. The first and second constructs are also provided with a 3xP3 marker, which is a universal marker used to screen and identify transgenic individuals. The first construct has a 3xP3-eGFP marker which can be used to screen and identify transgenic individuals in which the first construct has been inserted in chromosome 2. The second construct has a 3xP3-dsRed (SEQ ID NO: 48 and SEQ ID NO: 49) marker which can be used to screen and identify transgenic individuals in which the second construct has been inserted in chromosome 3. The ubiquitous promoter Opie2 (SEQ ID NO: 34 and SEQ ID NO: 35) is provided on the first construct. The non-ubiquitous promoter *Aedes* Exu is provided on the second construct. Generation of DSB by Cas9 cleave of the Cas9 cleave on the first and second construct would result in homologous recombination between chromosomes 2 and 3 and result in the generation of reciprocal translocation chromosomes.

Example 10—*Aedes* Translocation B

Figure 11:
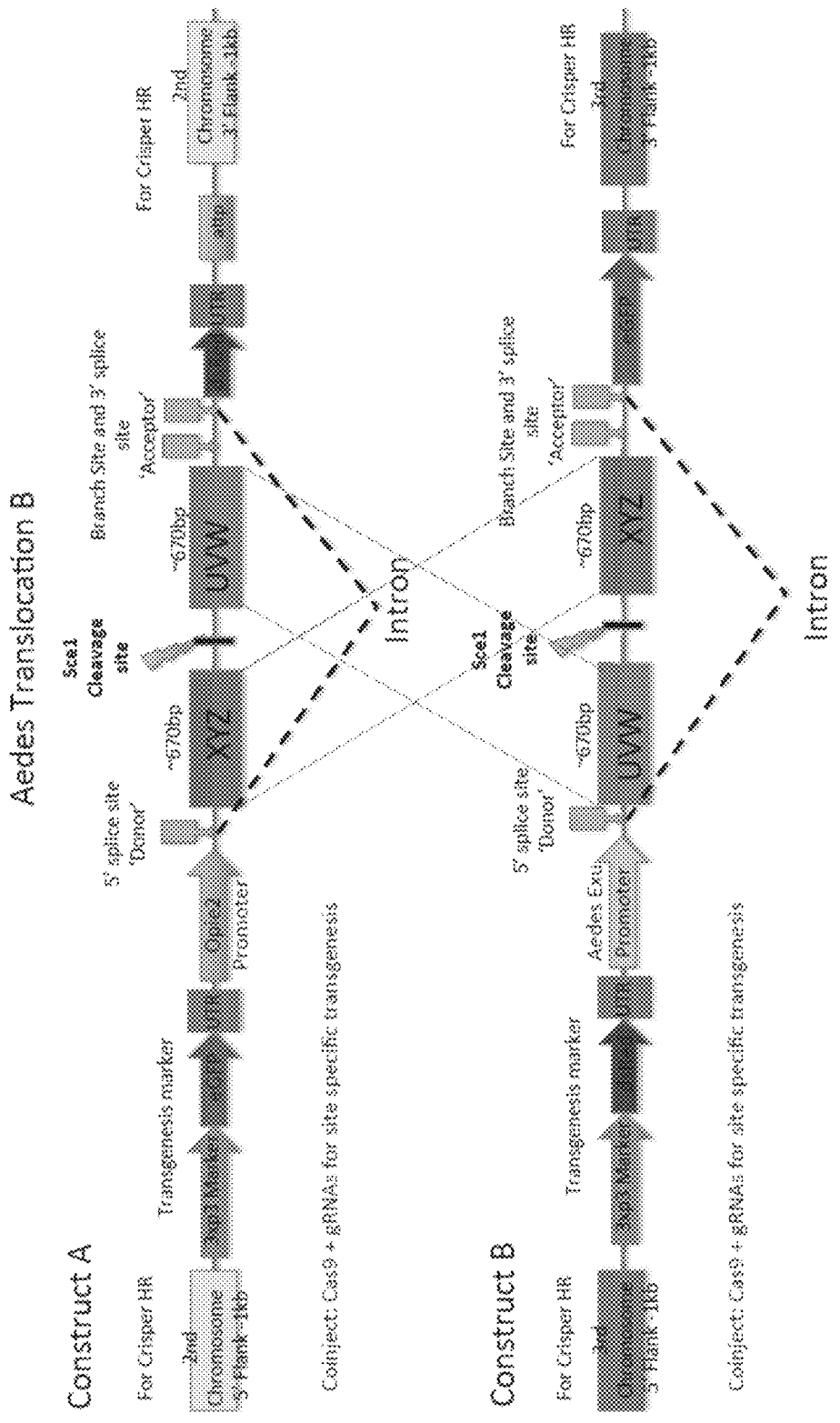
FIG. 11 shows an illustration of an embodiment of reciprocal chromosomal translocation in *Aedes*.

Translocations can be generated in *Aedes* mosquitoes based on the system design provided in FIG. 11. An embodiment of a gene drive system for *Aedes* is provided in FIG. 11. The system of FIG. 11 comprises a first construct (construct A). The first construct is inserted in chromosome 2. The system comprises a second construct (construct B), The second construct is inserted in chromosome 3. CRISPR/Cas9 is employed for the insertion of the first and second constructs in chromosomes 2 and 3, respectively. In the system of FIG. 11, the first and second constructs have a SceI nuclease cutting sites instead of Cas9 nuclease cutting sites. DSBs are generated in the first and second constructs by SceI nuclease which cuts at SceI cleavage sites in the first and second constructs. The first and second constructs are also provided with a 3xP3 marker, which is a universal marker used to screen and identify transgenic individuals. The first construct has a 3xP3-eGFP marker which can be used to screen and identify transgenic individuals in which the first construct has been inserted in chromosome 2. The second construct has a 3xP3-dsRed (SEQ ID NO: 48 and SEQ ID NO: 49) marker which can be used to screen and identify transgenic individuals in which the second construct has been inserted in chromosome 3, The ubiquitous promoter Opie2 (SEQ ID NO: 34 and SEQ ID NO: 35) is provided on the first construct. The non-ubiquitous promoter *Aedes* Exu is provided on the second construct. Generation of DSB by SceI on the first and second constructs would result in homologous recombination between chromosomes 2 and 3 and result in the generation of reciprocal translocation chromosomes.

Example 11—*Aedes* Translocation C

Figure 12:
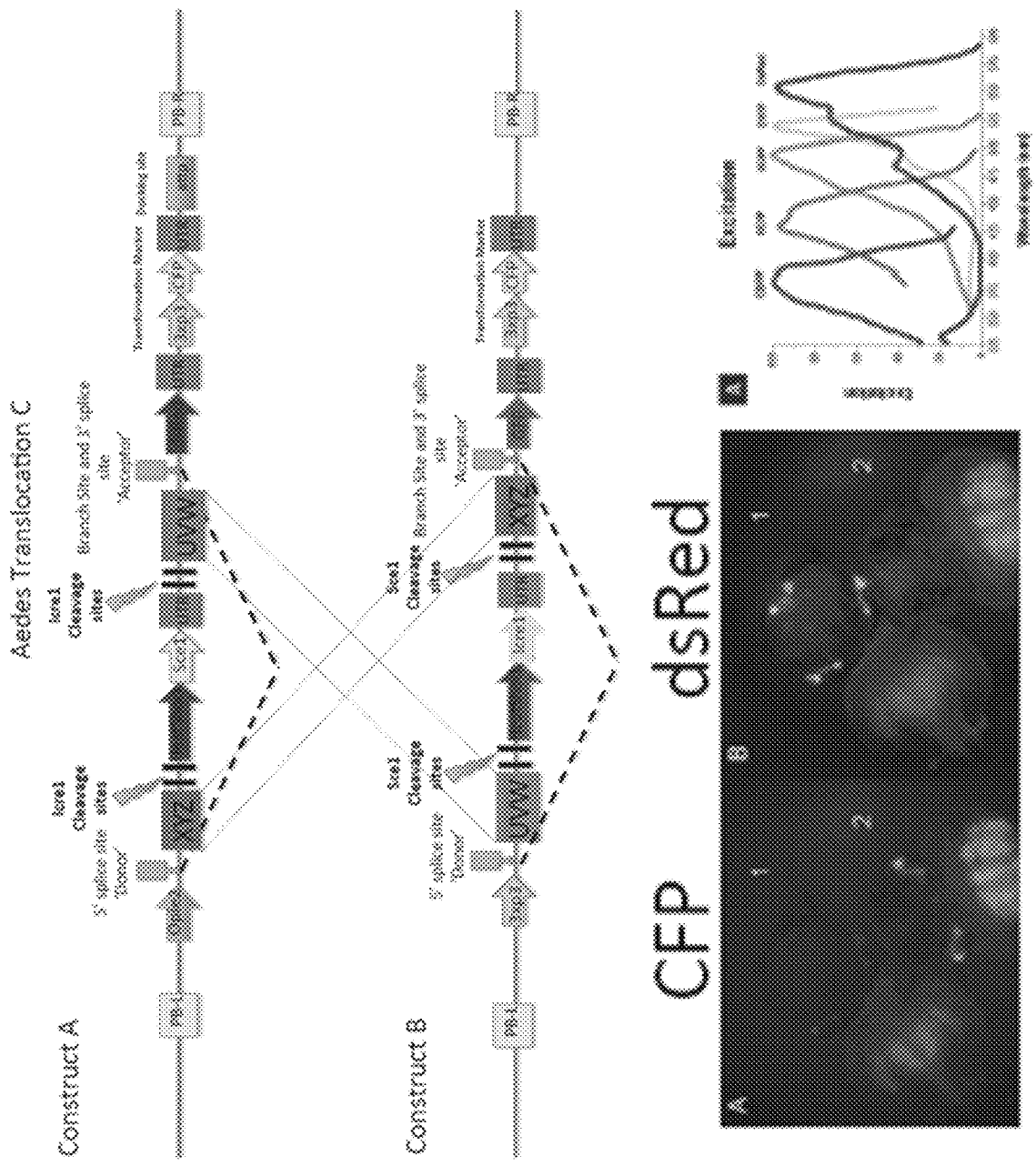
FIG. 12 shows an illustration of an embodiment of reciprocal chromosomal translocation in *Aedes*.

Translocations can be generated in *Aedes* mosquitoes based on the system design provided in FIG. 12, An embodiment of a gene drive system for *Aedes* is provided in FIG. 12. The system comprises a first construct (construct A) and a second construct (construct B). The first and second constructs are inserted in a first chromosome and a second chromosome, respectively, by employing the piggyBac transposon. Insertion sites PB-R and PB-L of the piggyBac transposon are provided in the first and second constructs, PB-L and PB-R allow the first and second constructs are to be inserted in a first chromosome and a second chromosome, respectively. The first and second constructs are also provided with a 3xP3 marker, which is a universal marker used to screen and identify transgenic individuals. The first and second constructs have a 3xP3-CFP marker which can be used to screen and identify transgenic individuals in which the first and second constructs have been inserted the first and second chromosomes. The coding sequence for SceI is provided on the first construct. The coding sequence for SceI is operably linked to, and therefore under the regulation of, a heat shock promoter. The coding sequence for IcreI is provided on the second construct. The coding sequence for IcreI is operably linked to, and therefore under the regulation of, a heat shock promoter. In the system of FIG. 12, the first construct has two cutting sites for a first nuclease and the second construct has two cutting sites for a second nuclease. For example, the first construct has two IcreI nuclease cutting sites and the second construct has two SceI nuclease cutting sites (FIG. 12). DSB is generated in the first construct by the IcreI nuclease which cuts at the two IcreI cleavage sites in the first construct. DSB is generated in the second construct by SceI nuclease which cuts at the two SceI cleavage site in the second construct. By providing the first construct with a first nuclease cutting site and the coding sequence of the first nuclease on the second construct, and the second construct with a second nuclease cutting site and the coding sequence of the second nuclease on the first construct, the system is made operational only in those insects in which both constructs are present. The two cutting sites for the first nuclease on the first construct are provided flanking the sequence encoding the second nuclease and the two cutting sites for the second nuclease on the second construct are provided flanking the sequence encoding the first nuclease. By proving the two cutting sites for the first nuclease on the first construct flanking the sequence encoding the second nuclease and the two cutting sites for the second nuclease on the second construct flanking the sequence encoding the first nuclease, generation of DSB when the first and second nucleases cut at both of their cutting sites results in the elimination of the sequences encoding the two nucleases and therefore eliminates any lingering effect of the nucleases. The ubiquitous promoter Opie2 (SEQ ID NO: 34 and SEQ ID NO: 35) is provided on the first construct. The non-ubiquitous promoter 3xP3 is provided on the second construct. Generation of DSB by IcreI and SceI on the first and second constructs, respectively, would result in homologous recombination between the first and second chromosomes and result in the generation of reciprocal translocation chromosomes. Ubiquitous and non-ubiquitous expression of CFP and dsRed (SEQ ID NO: 48 and SEQ ID NO: 49) are shown in FIG. 12 (bottom).

Example 12—*Aedes* Translocation Conservative A

Figure 13:
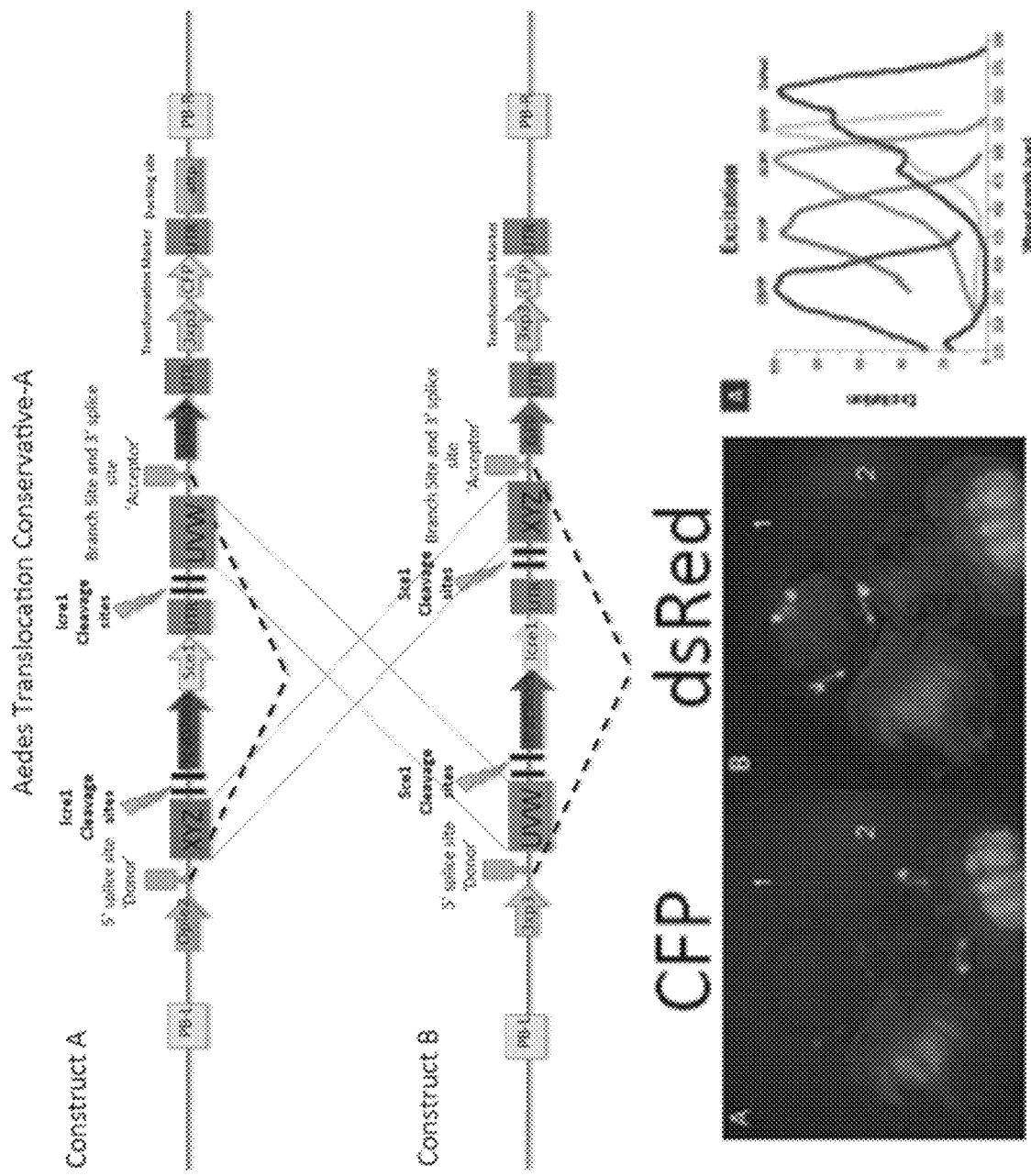
FIG. 13 shows an illustration of an embodiment of reciprocal chromosomal translocation in *Aedes*.

Translocations can be generated in *Aedes* mosquitoes based on the system design provided in FIG. 13, An embodiment of a gene drive system for *Aedes* is provided in FIG. 13. The system comprises a first construct (construct A) and a second construct (construct B). The first and second constructs are inserted in a first chromosome and a second chromosome, respectively, by employing the piggyBac transposon. Insertion sites PB-R and PB-L of the piggyBac transposon are provided in the first and second constructs. PB-L and PB-R allow the first and second constructs are to be inserted in a first chromosome and a second chromosome, respectively. The first and second constructs are also provided with a 3xP3 marker, which is a universal marker used to screen and identify transgenic individuals. The first and second constructs have a 3xP3-CFP marker which can be used to screen and identify transgenic individuals in which the first and second constructs have been inserted the first and second chromosomes. The coding sequence for SceI is provided on the first construct. The coding sequence for SceI is operably linked to, and therefore under the regulation of, a heat shock promoter. The coding sequence for IcreI is provided on the second construct. The coding sequence for IcreI is operably linked to, and therefore under the regulation of, a heat shock promoter. In the system of FIG. 13, the first construct has two cutting sites for a first nuclease and the second construct has two cutting sites for a second nuclease. For example, in some embodiments, the first construct has two IcreI nuclease cutting sites and the second construct has two SceI nuclease cutting sites (FIG. 13). DSB is generated in the first construct by the IcreI nuclease which cuts at the two IcreI cleavage sites in the first construct. DSB is generated in the second construct by SceI nuclease which cuts at the two SceI cleavage site in the second construct. By providing the first construct with a first nuclease cutting site and the coding sequence of the first nuclease on the second construct, and the second construct with a second nuclease cutting site and the coding sequence of the second nuclease on the first construct, the system is made operational only in those insects in which both constructs are present. The two cutting sites for the first nuclease on the first construct are provided flanking the sequence encoding the second nuclease and the two cutting sites for the second nuclease on the second construct are provided flanking the sequence encoding the first nuclease. By proving the two cutting sites for the first nuclease on the first construct flanking the sequence encoding the second nuclease and the two cutting sites for the second nuclease on the second construct flanking the sequence encoding the first nuclease, generation of DSB when the first and second nucleases cut at both of their cutting sites results in the elimination of the sequences encoding the two nucleases and therefore eliminates any lingering effect of the nucleases. The ubiquitous promoter Opie2 (SEQ ID NO: 34 and SEQ ID NO: 35) is provided on the first construct The non-ubiquitous promoter 3xP3 is provided on the second construct. Generation of DSB by IcreI and SceI on the first and second constructs, respectively would result in homologous recombination between the first and second chromosomes and result in the generation of reciprocal translocation chromosomes. Ubiquitous and non-ubiquitous expression of CFP and dsRed (SEQ ID NO: 48 and SEQ ID NO: 49) are shown in FIG. 13 (bottom).

In some embodiments, two-transgene translocation approaches can be used by using two different rare enconucleases from lists: *Anopheles*.homingsites.summary, *Drosophila*_GCA_000001215,homingsites.summary and following the system design *Aedes* Translocation Conservative-A provided in Example 12.

Example 13—*Aedes* Translocation D

Figure 14:
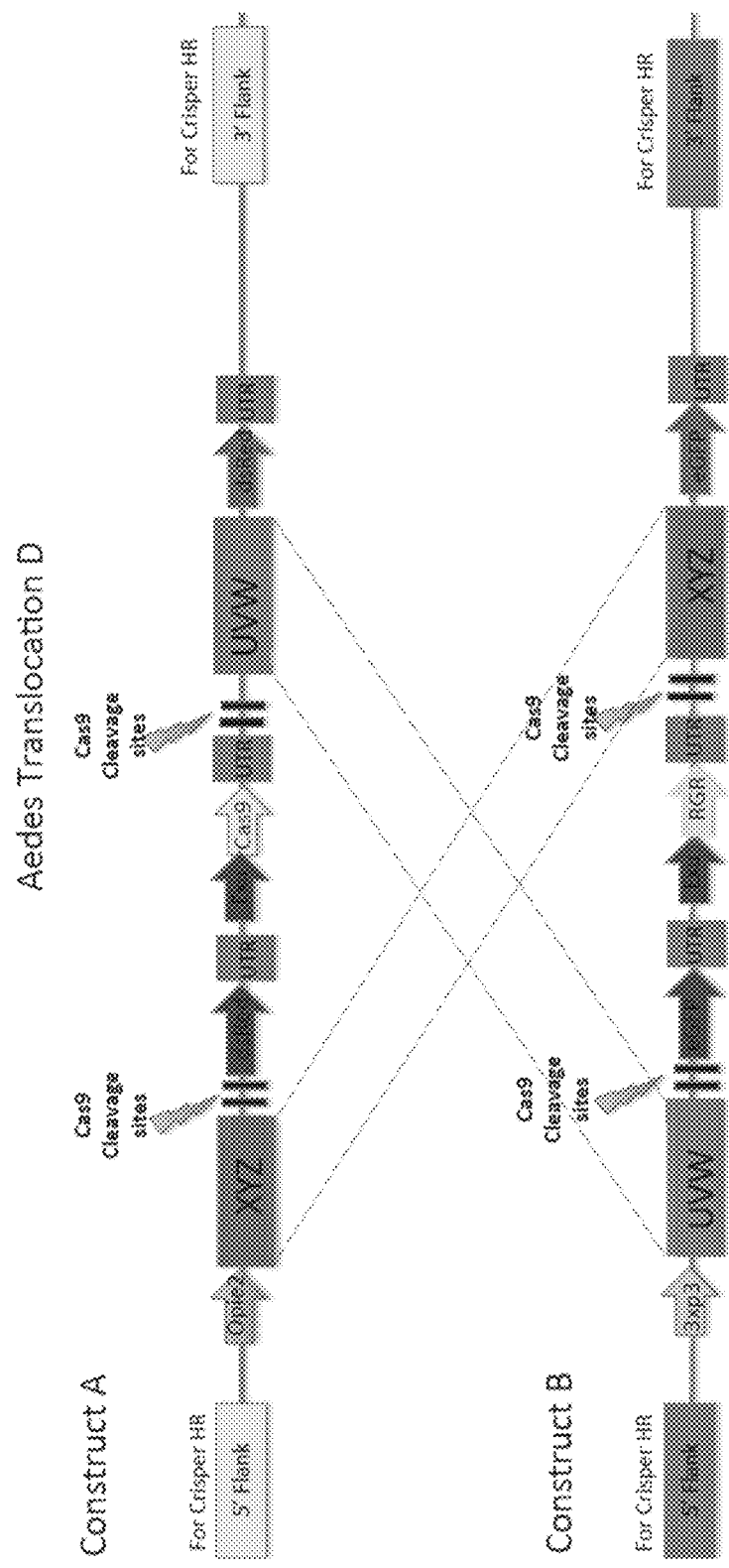
FIG. 14 shows an illustration of an embodiment of reciprocal chromosomal translocation in *Aedes*.

Translocations can be generated in *Aedes* mosquitoes based on the system design provided in FIG. 14. An embodiment of a gene drive system for *Aedes* is provided in FIG. 14. The system comprises a first construct (construct A) and a second construct (construct B). The first construct is inserted in a first chromosome. Cas9 nuclease and a first guide RNA are provided for the insertion of the first construct in the first chromosome. The second construct is inserted in a second chromosome. Cas9 nuclease and a second guide RNA are provided for the insertion of the second construct in the second chromosome. The first and second constructs each have two Cas9 nuclease cutting sites. In some embodiments, the coding sequence for Cas9 nuclease is provided on the first construct. The coding sequence for SceI is operably linked to, and therefore under the regulation of, the Exu promoter. The coding sequence for RGR is provided on the second construct. The coding sequence for RGR is operably linked to, and therefore under the regulation of, the Exu promoter. In the system of FIG. 14, the first and second constructs each have two cutting sites for Cas9 nuclease. DSB is generated in the first and second constructs by Cas9 nuclease which cuts at the two Cas9 cleave sites in the first and second constructs. The two cutting sites for Cas9 nuclease on the first and second constructs are provided flanking the sequence encoding the Cas9 nuclease on the first construct and flanking the sequence encoding RGR. By proving the two cutting sites for Cas9 nuclease on the first and second constructs flanking the sequence encoding Cas9 nuclease on the first construct and flanking the sequence encoding RGR on the second construct, generation of DSB when Cas9 cuts the first and second constructs results in the elimination of the sequences encoding Cas9 nuclease and RGR and therefore eliminates any lingering effect of Cas9 nuclease and RGR. The ubiquitous promoter Opie2 (SEQ ID NO: 34 and SEQ ID NO: 35) is provided on the first construct. The non-ubiquitous promoter 3xP3 is provided on the second construct. In some embodiments, generation of DSB by Cas9 nuclease on the first and second constructs would result in homologous recombination between the first and second chromosomes and result in the generation of reciprocal translocation chromosomes.

Example 14—*Aedes* Translocation E

Figure 15:
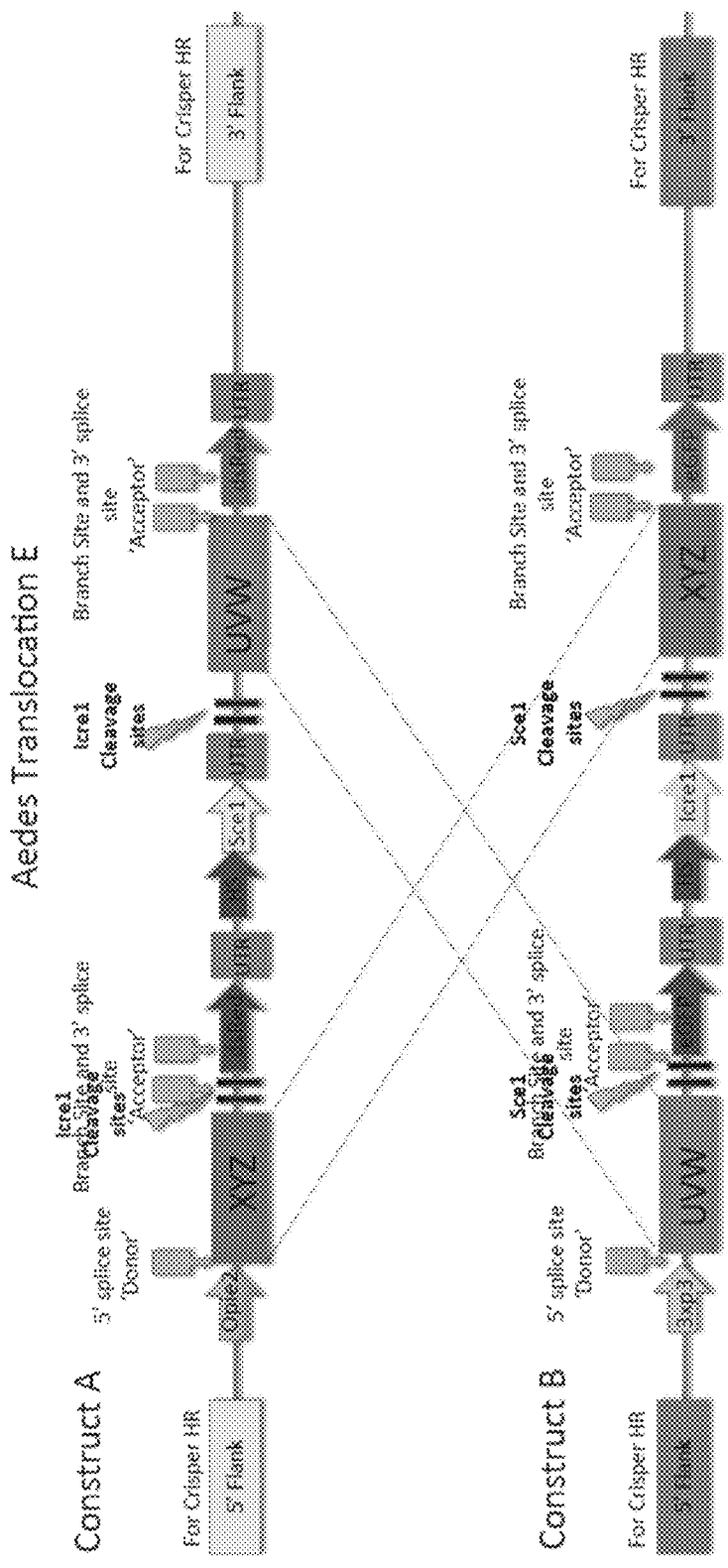
FIG. 15 shows an illustration of an embodiment of reciprocal chromosomal translocation in *Aedes*.

Translocations can be generated in *Aedes* mosquitoes based on the system design provided in FIG. 15. An embodiment of a gene drive system for *Aedes* is provided in FIG. 15. The system comprises a first construct (construct A) and a second construct (construct B). The first construct is inserted in a first chromosome. Cas9 nuclease and a first guide RNA are provided for the insertion of the first construct in the first chromosome. The second construct is inserted in a second chromosome. Cas9 nuclease and a second guide RNA are provided for the insertion of the second construct in the second chromosome. The coding sequence for SceI is provided on the first construct. The coding sequence for SceI is operably linked to, and therefore under the regulation of, a heat shock promoter. The coding sequence for IcreI is provided on the second construct. The coding sequence for IcreI is operably linked to, and therefore under the regulation of, a heat shock promoter. In some embodiments of the system of FIG. 15, the first construct has two cutting sites for a first nuclease and the second construct has two cutting sites for a second nuclease. For example, the first construct has two IcreI nuclease cutting sites and the second construct has two SceI nuclease cutting sites (FIG. 15). DSB is generated in the first construct by the IcreI nuclease which cuts at the two IcreI cleavage sites in the first construct. DSB is generated in the second construct by SceI nuclease which cuts at the two SceI cleavage site in the second construct. By providing the first construct with a first nuclease cutting site and the coding sequence of the first nuclease on the second construct, and the second construct with a second nuclease cutting site and the coding sequence of the second nuclease on the first construct, the system is made operational only in those insects in which both constructs are present. The two cutting sites for the first nuclease on the first construct are provided flanking the sequence encoding the second nuclease and the two cutting sites for the second nuclease on the second construct are provided flanking the sequence encoding the first nuclease. By proving the two cutting sites for the first nuclease on the first construct flanking the sequence encoding the second nuclease and the two cutting sites for the second nuclease on the second construct flanking the sequence encoding the first nuclease, generation of DSB when the first and second nucleases cut at both of their cutting sites results in the elimination of the sequences encoding the two nucleases and therefore eliminates any lingering effect of the nucleases. The ubiquitous promoter Opie2 (SEQ ID NO: 34 and SEQ ID NO: 35) is provided on the first construct. The non-ubiquitous promoter 3xP3 is provided on the second construct. In some embodiments, generation of DSB by IcreI and SceI on the first and second constructs, respectively, would result in homologous recombination between the first and second chromosomes and result in the generation of reciprocal translocation chromosomes.

Example 15—Methods

Example 15.1—Construct Assembly

Gibson enzymatic assembly (EA) cloning method was used for all cloning (Gibson et al., 2009). For both constructs (A and B), translocation allele components were cloned into the multiple cloning site (MCS) of a commonly used plasmid in the lab for *Drosophila melanogaster* transformation that contains the white gene as a marker and an attB-docking site. For construct A (FIG. 5, the oenocyte-specific svp enhancer fragments (SEQ ID NO: 36 and SEQ ID NO: 37) (Gutierrez et al. 2007) and hsp70 basal promoter fragments (SEQ ID NO: 38 and SEQ ID NO: 39) were amplified from *Drosophila melanogaster* genomic DNA using primers P16 (SEQ ID NO: 16) and P17 (SEQ ID NO: 17) (svp (SEQ ID NO: 36 and SEQ ID NO: 37)) and P18 (SEQ ID NO: 18) and P19 (SEQ ID NO: 19) (hsp70 (SEQ ID NO: 38 and SEQ ID NO: 39)). The GFP (SEQ ID NO: 46 and SEQ ID NO: 47) fragment was amplified from template pAAV-GFP (SEQ ID NO: 46 and SEQ ID NO: 47) (addgene plasmid #32395) using primers P26 (SEQ ID NO: 26) and P27 (SEQ ID NO: 27), with a Kozak sequence (CAACAAA (SEQ ID NO: 73)) directly 5' of the GFP (SEQ ID NO: 46 and SEQ ID NO: 47) start codon added with primer P26 (SEQ ID NO: 26), and the SV40 3'UTR fragment (SEQ ID NO: 50 and SEQ ID NO: 51) was amplified from template pMos-3xP3-DsRed-attp (addgene plasmid #52904) using primers P28 (SEQ ID NO: 28) and P10 (SEQ ID NO: 10). The 5' and 3' CTCF insulator fragments (SEQ ID NO: 52 and SEQ ID NO: 53) were amplified from *Drosophila melanogaster* genomic DNA using primers P11 (SEQ ID NO: 11) and P15 (SEQ ID NO: 15) (for the 5' CTCF (SEQ ID NO: 52 and SEQ ID NO: 53) fragment) and P13 (SEQ ID NO: 13) and P14 (SEQ ID NO: 14) (for the 3' CTCF (SEQ ID NO: 52 and SEQ ID NO: 53) fragment). The XYZ (SEQ ID NO: 42 and SEQ ID NO: 43) and UVW (SEQ ID NO: 44 and SEQ ID NO: 45) fragments were amplified as above with primers P22 (SEQ ID NO: 22) and P23 (SEQ ID NO: 23) (XYZ (SEQ ID NO: 42 and SEQ ID NO: 43)) and P20 (SEQ ID NO: 20) and P21 (SEQ ID NO: 21) (UVW (SEQ ID NO: 44 and SEQ ID NO: 45)). The 5' and 3' splice sites utilized were the same as above; the 5' splice site was added to the 5' end of the UVW (SEQ ID NO: 44 and SEQ ID NO: 45) fragment via PCR with primer P24 (SEQ ID NO: 24), and the 3' splice site was added to the 3' end of fragment XYZ (SEQ ID NO: 42 and SEQ ID NO: 43) via PCR with primer P25 (SEQ ID NO: 25). Two I-SceI recognition sequences, arranged as described above, were added to the 3' end of the UVW (SEQ ID NO: 44 and SEQ ID NO: 45) fragment with primer P21 (SEQ ID NO: 21) and the 5' end of the XYZ (SEQ ID NO: 42 and SEQ ID NO: 43) fragment with primer P22 (SEQ ID NO: 22). The construct was assembled in two steps, as above, with the first (5') CTCF (SEQ ID NO: 52 and SEQ ID NO: 53), the svp (SEQ ID NO: 36 and SEQ ID NO: 37) and hsp70 fragments (SEQ ID NO: 38 and SEQ ID NO: 39), the UVW (SEQ ID NO: 44 and SEQ ID NO: 45) fragment, and the XYZ (SEQ ID NO: 42 and SEQ ID NO: 43) fragment cloned in via a first EA cloning step, and the GFP (SEQ ID NO: 46 and SEQ ID NO: 47) fragment, the SV40 3'UTR fragment (SEQ ID NO: 50 and SEQ ID NO: 51), and the second (3') CTCF (SEQ ID NO: 52 and SEQ ID NO: 53) cloned in via a second EA cloning step. For construct B (FIG. 5, the Opie2 (SEQ ID NO: 34 and SEQ ID NO: 35) promoter fragment was amplified from plasmid pIZ/V5-His/CAT (Invitrogen) using primers P1 (SEQ ID NO: 1) and P2 (SEQ ID NO: 2). The 667 bp XYZ (SEQ ID NO: 42 and SEQ ID NO: 43) and 668 bp UVW (SEQ ID NO: 44 and SEQ ID NO: 45) translocation fragments (labeled XYZ (SEQ ID NO: 42 and SEQ ID NO: 43) and UVW (SEQ ID NO: 44 and SEQ ID NO: 45), for clarity), were amplified from plasmid pFUSEss-CHIg-mG1 (Invivogen, San Diego, Calif.) using primers P3 (SEQ ID NO: 3) and P4 (SEQ ID NO: 4) (XYZ (SEQ ID NO: 42 and SEQ ID NO: 43)) and P5 (SEQ ID NO: 5) and P6 (SEQ ID NO: 6) (UVW (SEQ ID NO: 44 and SEQ ID NO: 45)). The 18 bp I-SceI recognition sequence is ATTACCCTGT-TATCCCTA (SEQ ID NO: 29). Two 18 bp I-SceI recognition sequences (ATTACCCTGTTATCCCTA-CTAG-TAGGGATAACAGGGTAAT (SEQ ID NO: 74)) were added to the 3' end of the XYZ (SEQ ID NO: 42 and SEQ ID NO: 43) fragment and the 5' end of the UVW (SEQ ID NO: 44 and SEQ ID NO: 45) fragment in inverse orientation to each other separated by a 4 bp linker sequence (CTAG (SEQ ID NO: 75)) by aforementioned primers P4 (SEQ ID NO: 4) (for XYZ (SEQ ID NO: 42 and SEQ ID NO: 43)) and P5 (SEQ ID NO: 5) (for UVW (SEQ ID NO: 44 and SEQ ID NO: 45)). The 5' and 3' splice sites utilized were from a 67 bp intron located in the *Drosophila melanogaster* Myosin Heavy Chain (Mhc) gene ID CG17927; the 5' splice site was added to the 5' end of the XYZ (SEQ ID NO: 42 and SEQ ID NO: 43) fragment via PCR with primer P7 (SEQ ID NO: 7), and the 3' splice site was added to the 3' end of fragment UVW (SEQ ID NO: 44 and SEQ. ID NO: 45) via PCR with primer P8 (SEQ ID NO: 8). The dsRed (SEQ ID NO: 48 and SEQ ID NO: 49) fragment, together with the SV40 3'UTR (SEQ ID NO: 50 and SEQ ID NO: 51), were amplified from template pMos-3xP3-DsRed-attp (addgene plasmid #52904) using primers P9 (SEQ ID NO: 9) and P10 (SEQ ID NO: 10), with a Kozak sequence (CAACAAA (SEQ ID NO: 73)) directly 5' of the DsRed (SEQ ID NO: 48 and SEQ ID NO: 49) start codon added with primer P9. The 5' and 3' CTCF (SEQ ID NO: 52 and SEQ ID NO: 53) insulator fragments (Kyrchanova et al., 2008) were amplified from *Drosophila melanogaster* genomic DNA using primers P11 (SEQ ID NO: 11) and P12 (SEQ ID NO: 12) (for the 5' CTCF (SEQ ID NO: 52 and SEQ ID NO: 53) fragment) and P13 (SEQ ID NO: 13) and P14 (SEQ ID NO: 14) (for the 3' CTCF (SEQ ID NO: 52 and SEQ ID NO: 53) fragment). The construct was assembled in two steps. First, the *Drosophila melanogaster* attB stock plasmid was digested with AscI and XbaI, and the first (5') CTCF (SEQ ID NO: 52 and SEQ ID NO: 53), the Opie2 (SEQ ID NO: 34 and SEQ ID NO: 35) promoter, the XYZ (SEQ ID NO: 42 and SEQ ID NO: 43) fragment, and the UVW (SEQ ID NO: 44 and SEQ ID NO: 45) fragments were cloned in via EA cloning. Then, the resulting plasmid was digested with XhoI, and the dsRed (SEQ ID NO: 48 and SEQ ID NO: 49) -SV40 3'UTR (SEQ ID NO: 50 and SEQ ID NO: 51) fragment and the second (3') CTCF (SEQ ID NO: 52 and SEQ ID NO: 53) were cloned in via EA cloning. All sequences were analyzed with NNSPLICE 0.9 (available at fruitfly.org/seq_tools/splice.html to confirm strength of splice signals and to check for cryptic splice sites. A list of primer sequences used in the above construct assembly can be found in FIG. 17-FIG. 19.

Example 15.2—Construct Assembly

Translocation allele components were cloned into a multiple cloning site (MCS)-containing *Drosophila* attB backbone using the enzymatic assembly (EA) cloning method described by Gibson et al. 2009. For construct A (FIG. 3), the Opie2 (SEQ ID NO: 34 and SEQ ID NO: 35) promoter fragment was PCR amplified from plasmid OA791 (provided by O. Akbari), and dsRed (SEQ ID NO: 48 and SEQ ID NO: 49) and SV40 3'UTR (SEQ ID NO: 50 and SEQ ID NO: 51) were amplified from various constructs (AB Buchman Thesis) The UVW (SEQ ID NO: 44 and SEQ ID NO: 45) and XYZ (SEQ ID NO: 42 and SEQ ID NO: 43) stuffer fragments were PCR amplified from a plasmid provided by J. Li, which she generated by cloning an IgG variable region (Nath 2003) upstream of the mouse IgG heavy chain constant region contained in plasmid pFUSEss-CHIg-mG1 (Invivogen, San Diego, Calif.). Two I-SceI recognition sites were added between the fragments via PCR, 5' and 3' splice sites from an Rpl35a intron (SEQ ID NO: 30 and SEQ ID NO: 31) were also PCR amplified onto the fragment ends, and the resulting stuffer region was then inserted between Opie2 (SEQ ID NO: 34 and SEQ ID NO: 35) and dsRed (SEQ ID NO: 48 and SEQ ID NO: 49). For construct B, this process was identical except that the UVW (SEQ ID NO: 44 and SEQ ID NO: 45) and XYZ (SEQ ID NO: 42 and SEQ ID NO: 43) fragments were arranged on opposite sides (UVW (SEQ ID NO: 44 and SEQ ID NO: 45) on the left, XYZ (SEQ ID NO: 42 and SEQ ID NO: 43) on the right). The svp enhancer (SEQ ID NO: 36 and SEQ ID NO: 37) plus hsp70 basal promoter (SEQ ID NO: 38 and SEQ ID NO: 39), GFP (SEQ ID NO: 46 and SEQ ID NO: 47), and SV40 3'UTR (SEQ ID NO: 50 and SEQ ID NO: 51) for construct B were PCR amplified from plasmids described in Chapter (AB Buchman thesis) Both GFP (SEQ ID NO: 46 and SEQ ID NO: 47) and dsRed (SEQ ID NO: 48 and SEQ ID NO: 49) had a Kozak sequence (CAACAAA (SEQ ID NO: 73)) directly 5' of the start codon. Both translocation alleles were flanked by CTCF (SEQ ID NO: 52 and SEQ ID NO: 53) insulators, which were PCR amplified from constructs described in Chapter 3. (AB Buchman thesis)

To test splicing of the above constructs in S2 culture, the tissue-specific promoters were replaced by Actin5 (SEQ ID NO: 40 and SEQ ID NO: 41), which was PCR amplified from pAc5.1-HisB. To replace the Rpl35a splicing signals, 5' and 3' splice sites from the MHC16 intron (SEQ ID NO: 32 and SEQ ID NO: 33) (Pfeiffer et al, 2010) were PCR amplified onto each stuffer region, and these regions were inserted in place of the original ones by EA. After these were shown to splice properly in S2 culture, the Actin5 promoter (SEQ ID NO: 40 and SEQ ID NO: 41) was replaced by the original tissue-specific promoters. All sequences were analyzed with NNSPLICE 0.9 (available at fruitfly.org/seq_tools/splice.html) to confirm strength of splice signals and to check for cryptic splice sites.

The full sequences of the I-SceI recognition site, Rpl35a intron 5' and 3' splice signals (SEQ ID NO: 30 and SEQ ID NO: 31), and MHC16 intron 5' and 3' signals (SEQ ID NO: 32 and SEQ ID NO: 33), along with the first and last 30 base pairs (bps) of all longer DNA fragments used in the described constructs, are listed in FIG. 17-FIG. 19.

Example 15.3—Fly Culture and Strains

Fly husbandry and crosses were performed under standard conditions at 25° C., Rainbow Transgenics (Camarillo, Calif.) carried out all of the fly injections. Bloomington Stock Center (BSC) fly strains utilized to generate translocations were attP lines 68E (BSC #24485: y1 M{vas-int.Dm}ZH-2A w*; M{3xP3-RFP.attP'}ZH-68E), 51C (BSC #24482; y[1] M{vas-int.Dm}ZH-2A w[*]; M{3xP3-RFP.attP'}ZH-51C), and 9741 (BSC #9741: y[1] w[1118]; PBac {y[+]-attP-9A}VK00023). Fly Stock BSC#6935 (y[1]

w[*]; P{ry[+t7.2]=70FLP}23 P{v[+t1.8]-70I-SceI}4A/TM) was used as the source of heat shock induced I-SceI. For balancing chromosomes, fly stocks BSC#39631 (w[*]; wg[Sp-1]/CyO; P{ry[+t7.2]=neoFRT}82B lsn[SS6]/TM6C, Sb[1]) BSC#2555 (CyO/sna[Sco]) were used. For introgression into wildtype background we used the Canton-S stock BSC#1. Both translocation transgenes (A and B) were inserted into three sites-51C, 68E and 9741 (genotypes described above) using phiC31 mediated attP/attB integration. These site combinations allowed for the generation of two distinct translocation types (51C/68E and 51C/9741 combinations). Homozygous stocks were first generated for both 51C/68E and 51C/9741 site combinations to determine whether the translocations would be viable in the homozygous state by crossing translocation heterozygotes and identifying homozygous progeny by eye color (light orange eyes for homozygotes versus yellow for heterozygotes for the 51C/68E site combination; light red eyes for homozygotes versus orange for heterozygotes for the 51C/9741 site combination). After confirming homozygous viability, introgressed stocks were generated for both site combinations (to remove any background deleterious alleles) by outcrossing crossing heterozygous translocation males to Canton-S virgin females for eight consecutive generations, and then crossing heterozygous males and virgin females five times consecutively to generate a homozygous stock in the Canton-S background for each site combination. Homozygosity was confirmed by outcrossing. Drive experiments for these stocks were set up against the wild type Canton-S stock. Heat shocks were conducted by submerging fly vials in a water bath set to 38° C. for one hour. Larvae were heat shocked at minimum five times during development. Offspring of heat-shocked larvae were screened for translocation specific marker expression.

Example 15.4—Fly Culture and Strains

Fly husbandry and crosses were performed under standard conditions at 25° C. BestGene (Chino Hills, Calif.) and Rainbow Transgenics (Camarillo, Calif.) carried out all of the fly injections, with Rainbow Transgenics performing the vast majority of them with consistent reliability.

Additional fly strains utilized in this study were attP lines 22A (Bloomington Stock Center #24481), 68E (#24485), 96E (#24487), 51C (#24482), and #9741. Stock #6935 was used as the source of heat shock I-SceI. Stocks #39631 #2555 were used for all balancing.

The translocation constructs were inserted into three sites—51C on the second chromosome and 68E and 70A2 on the third chromosome—so that two distinct translocation types could be generated (one from the 51C/68E combination, the other from the 51C/9741(70A2) combination). Healthy homozygous stocks were generated for both target site combinations.

Heat shocks were initially carried out by placing fly vials in a fly incubator set at 38° C. for one hour. However, after only one translocation individual was recovered, heat shocks were subsequently performed by placing fly vials in a 38° C. water bath for one hour, in hopes of increasing the efficiency of heat shock. Larvae were heat shocked ~five times during early development. Offspring of heat-shocked larvae were screened for ubiquitous expression of GFP (SEQ ID NO: 46 and SEQ ID NO: 47).

The crossing scheme used to bring both translocation alleles and the I-SceI source into a single fly line is detailed in Appendix C (AB Buchman thesis). The process of setting up drive experiments is also described in Appendix C (AB Buchman thesis).

Example 15.5—Cell Culture

Drosophila S2 cells were maintained in Schneider's medium with 10% FBS, 1% penicillin and streptomycin at 27.5° C., and passaged every ~four days. Transfections were performed with the FuGENE6 reagent (Promega, Madison, Wis.), using a ratio of 2.5 µl: 1 µg of FuGENE to DNA. A GFP (SEQ ID NO: 46 and SEQ ID NO: 47) or RFP marker was always used as a transfection control, and usually made up 20% of the DNA transfected, DNA used for transfection was typically prepared using Zyppy™ Plasmid Miniprep Kit (Zymo Research, Irvine, Calif.) and eluted in endotoxin-free TE buffer.

Example 15.6—Embryo and Adult Viability Determination

For embryo viability counts (FIG. 16; Example 7), 2-4 day old adult virgin females were mated with males of the relevant genotypes for 2-3 days in egg collection chambers, supplemented with yeast paste. On the following day, a 3 hr egg collection was carried out, after first having cleared old eggs from the females through a pre-collection period on a separate plate for 3 hrs. Embryos were isolated into groups and kept on an agar surface at 25° C. for 48-72 hrs. The % survival was then determined by counting the number of unhatched embryos. One group of 100-200 embryos per cross was scored in each experiment, and each experiment was carried out in biological triplicate. The results presented are averages from these three experiments. Embryo survival was normalized with respect to the % survival observed in parallel experiments carried out with the Canton-S wild-type strain, which was 93.00% sd. 1.82%. For adult fly counts (FIG. 16; Example 7), individual flies for each genotype cross were singly mated. For each genotype cross, we set up 10-15 individual fly crosses, and the results presented are averages from all these experiments.

Example 15.7—Population Cage Experiments

All fly experiments were carried out at 25° C., 12 hour-12 hour day night cycle, with ambient humidity in 250 ml bottles containing Lewis medium supplemented with live, dry yeast. Starting populations for above threshold were as follows: 60%, 70%, 80% ($T_1/T_1$; $T_2/T_2$) for above threshold, and 20%, 30%, 40% ($T_1/T_1$; $T_2/T_2$) for below threshold, with the remainder of all these populations composed of wild type Canton-S (+/+; +/+). The total number of flies for each starting population was 100. All experiments were conducted in triplicate. All populations were initiated as half male and half female, with all females being virgins. After being placed together, adult flies were removed after exactly seven days. After another seven days, progeny were collected and separated in half arbitrarily. One half was counted, while the other half was placed in a new bottle to continue the simulation, and this process continued throughout the duration of the experiment.

Example 15.8—Genomic PCR

Genomic DNA was extracted from whole flies using Qiagen's DNeasy Blood and Tissue Kit (Qiagen, Valencia, Calif.). To determine the orientation of attP landing sites in each insertion line, a forward or reverse oligonucleotide primer inside the attP site (SEQ ID NO: 54, SEQ ID NO: 55, SEQ ID NO: 56 and SEQ ID NO: 57) was paired with a forward or reverse primer from the genomic region surrounding the insertion site (for a total of four PCR reactions per site), and PCR products from successful reactions were sequenced to confirm site orientation. As mentioned previously, three sites—51C on the second chromosome and 68E and 9741 (70A2) on the third chromosome—were chosen for generating transformants. Sequences of the forward and reversed primers used above for 51C (SEQ ID NO: 60 and SEQ ID NO: 61), 68E (SEQ ID NO: 62 and SEQ ID NO: 63) and 9741 (SEQ ID NO: 66 and SEQ ID NO: 67) are listed in FIG. 17-FIG. 19. Sequences of the forward and reversed primers used for 22A (SEQ ID NO: 58 and SEQ ID NO: 59) and 96E (SEQ ID NO: 64 and SEQ ID NO: 65) are listed in FIG. 17-FIG. 19.

To verify that isolated translocation-bearing individuals had expected construct architecture, a forward primer from each promoter was tested with reverse primers from both fluorescent reporters to check whether the promoters were now associated with novel reporters (i.e., Opie2 (SEQ ID NO: 34 and SEQ ID NO: 35) with GFP (SEQ ID NO: 46 and SEQ ID NO: 47), svp (SEQ ID NO: 36 and SEQ ID NO: 37) with dsRed (SEQ ID NO: 48 and SEQ ID NO: 49) and hsp70 (SEQ ID NO: 38 and SEQ ID NO: 39) with dsRed (SEQ ID NO: 48 and SEQ ID NO: 49)), and obtained PCR products were sequenced to confirm the expected loss of one stuffer fragment (XYZ (SEQ ID NO: 42 and SEQ ID NO: 43) or UVW (SEQ ID NO: 44 and SEQ ID NO: 45)). A forward primer at the very 3' end of the constructs was used with a reverse primer from the neighboring genomic region to confirm that translocation individuals had insertions at both attP sites, since only one of the translocation-associated markers (Opie2 (SEQ ID NO: 34 and SEQ ID NO: 35) -GFP (SEQ ID NO: 46 and SEQ ID NO: 47)) could be seen. Sequences of the primers used above (Opie2-F (SEQ ID NO: 68), GFP-R (SEQ ID NO: 69), Hsp70-F (SEQ ID NO: 70), dsRed-R (SEQ ID NO: 71) and SV40-F (SEQ ID NO: 72)) are listed in FIG. 17-FIG. 19.

Example 15.9—Theoretical Framework

The model of Curtis and Robinson (1971) was applied to describe the spread of reciprocal translocations through a population. This is a discrete-generation, deterministic population frequency model assuming random mating and an infinite population size. The first chromosome was denoted with a translocated segment by "T" and the wild-type version of this chromosome by "t." Similarly, the second chromosome was denoted with a translocated segment by "R" and the wild-type version of this chromosome by "r." As a two-locus system, there are nine possible genotypes; however, only individuals carrying the full chromosome complement are viable, which corresponds to the genotypes TTRR, TtRr and ttrr, the proportion of the kth generation of which are denoted by $p_k^{TTRR}$, $p_k^{TtRr}$ and $p_k^{ttrr}$. The four haplotypes that determine the genotype frequencies in the next generation—TR, tR, Tr and tr—are described by the following frequencies:

$f_k^{TR} = p_k^{TTRR}(1-s) + 0.25 p_k^{TtRr}(1-hs)$ $f_k^{tR} = f_k^{Tr} = 0.25 p_k^{TtRr}(1-hs)$ $f_k^{tr} = p_k^{ttrr} + 0.25 p_k^{TtRr}(1-hs)$ Here, s denotes the reduced fecundity of TTRR individuals and hs denotes the reduced fecundity of TtRr individuals relative to wild-type individuals, where h∈[0,1] By considering all possible mating pairs, the genotype frequencies in the next generation are:

$p_{k+1}^{TTRR} = (f_k^{TR})^2 / \sigma_k$ $p_{k+1}^{TtRr} = 2(f_k^{TR} f_k^{tr} + f_k^{tR} f_k^{Tr}) / \sigma_k$ $p_{k+1}^{ttrr} = (f_k^{tr})^2 / \sigma_k$ where $\sigma_k$ is a normalizing term given by, $\sigma_k = (f_k^{TR})^2 + 2(f_k^{TR} f_k^{tr} + f_k^{tR} f_k^{Tr}) + (f_k^{tr})^2$ A number of different fitness cost models were investigated and the one that provided the best fit to the data was selected. The simplest model is one in which the fitness of each genotype stays constant over time. Another model considers fitness costs that depend on the population frequency of the genotype. For linear frequency-dependence, this is given by, $s = (s_0 - s_1) p_k^{ttrr} + s_1$ Here, $s_0$ represents the fitness cost of a translocation homozygote in an almost fully wild-type population, and $s_1$ represents the fitness cost in an almost fully transgenic population. An alternative model is that fitness is time-dependent, as could be explained by introgression of introduced genotypes. For linear time-dependence, this is given by, $$s = \left(\frac{s_1 - s_0}{t_f}\right) t + s_0$$

Here, $s_0$ represents the fitness cost in the first generation and $s_1$ represents the fitness cost in the final generation, denoted by $t_f$. For sigmoidal time-dependence, it is given by, $$s = (s_0 - s_1)\left(1 - \frac{1}{1 + e^{-\alpha(1-\tau)}}\right) + s_1$$

Here, $s_0$ and $s_1$ are as before, $\tau$ denotes the time of intermediate fitness cost, and $\alpha$ denotes the speed of transition between the two fitness costs. For step-function time-dependence, it is given by, $$s = \begin{cases} s_0, & t \leq t_C \\ s_1, & t > t_C \end{cases}$$

Here, $s_0$ and $s_1$ are as before, and $t_C$ denotes the time of transition between the two fitness costs. And for exponential time-dependence, it is given by, $s = \alpha 2^{-t/t_{1/2}} + (s_0 - \alpha)$ Here, $s_0$ represents the fitness cost in the first generation, $S_1$ represents the fitness cost after many generations, $t_{1/2}$ denotes the time at which the fitness cost is halfway between the two, and $\alpha$ is given by, $$a = \frac{s_0 - s_1}{1 - 2^{-t_f/t_{1/2}}}$$

The fitness parameters were estimated for each model and compared models according to their Akaike Information Criterion (AIC) values. This was done using population count data for the 18 drive experiments conducted for each translocation system (three for each of the 80%, 70%, 60%, 40%, 30% and 20% release frequencies). AIC is calculated as 2 k−2 log L, where k denotes the number of model parameters, and the preferred model is the one with the smallest AIC value. The likelihood of this data was calculated, given fitness costs s and hs, assuming a binomial distribution of the two phenotypes (individuals homozygous or heterozygous for the translocation were considered as the same phenotype to match the experimental counts). Model predictions were used to generate expected genotype proportions over time for each fitness cost, and the log likelihood had the form, $$\log L(h, s) = \sum_{i=1}^{18} \sum_{k=1}^{14} \log\left(\frac{TTRR_{i,k} + TtRr_{i,k} + ttrr_{i,k}}{TTRR_{i,k} + TtRr_{i,k}}\right) + ttrr_{i,k} \log(p_{i,k}^{ttrr}(h, s)) + (TTRR_{i,k} + TtRr_{i,k})\log(1 - p_{i,k}^{ttrr}(h, s))$$

Here, $TTRR_{i,k}$, $TtRr_{i,k}$ and $ttrr_{i,k}$ represent the number of TTRR, TtRr and ttrr individuals at generation k in experiment i, and the corresponding expected genotype frequencies are fitness cost-dependent. The best estimate of the fitness cost is that having the highest log-likelihood. A 95% credible interval was estimated using a Markov Chain Monte Carlo sampling procedure. Matlab and R code implementing these equations is available upon request. The AIC values for each of the fitness cost models are shown in Table 1.

TABLE 1

| Fitness cost model: | AIC (Translocation system 1): | AIC (Translocation system 2): |
|---|---|---|
| Constant fitness costs | 6317.6 | 7225.0 |
| Linear, frequency-dependent fitness costs | 6011.2 | 6808.6 |
| Linear, time-dependent fitness costs | 4399.3 | 4388.6 |
| Sigmoidal, time-dependent fitness costs | 3518.1 | 3643.8 |
| Step function, time-dependent fitness costs | 3515.71 | 3641.7 |
| Exponential, time-dependent fitness costs | 3515.72 | 3641.7 |

In summary, the best fitting model for the translocation dynamics is one in which fitness costs are time-dependent, varying according to a step function. This could be consistent with a change in relative fitness once the introduced chromosomes have introgressed into the population. Calculations of fitness parameters for translocation system 1 suggest equal relative fitness for translocation homozygotes and heterozygotes with an initial relative fitness of transgenic individuals of 0.29 (95% CrI: 0.28-0.30) relative to wild-type individuals, rising to a relative fitness of 1.44 (95% CrI: 1.42-1.46) after the first generation. Calculations for translocation system 2 also suggest equal relative fitness for translocation homozygotes and heterozygotes with an initial relative fitness of transgenic individuals of 0.27 (95% CrI: 0.26-0.28) relative to wild-type individuals, rising to a relative fitness of 1.47 (95% CrI: 1.45-1.48) after the first generation.

The examples set forth above are provided to give those of ordinary skill in the art a complete disclosure and description of how to make and use the embodiments of translocation gene drive systems, methods and systems of the disclosure, and are not intended to limit the scope of what the inventors regard as their disclosure. Modifications of the above-described modes for carrying out the disclosure that are obvious to persons of skill in the art are intended to be within the scope of the disclosure. All publications mentioned in the specification are indicative of the levels of skill of those skilled in the art to which the disclosure pertains.

Additional Embodiments

The present disclosure demonstrates, as proof of concept, that translocations can be specifically generated and used as modulators of gene drive in insects.

The present disclosure clearly shows that choice of insertion sites is crucial to generating utilizable translocation individuals. In *Drosophila*, it can be worthwhile to attempt to create translocation stocks using completely fit insertion sites, so that drive experiments can be conducted against wild types in an unambiguous proof of principle experiment that conforms to predicted thresholds. If there is a dearth of existing fit insertion lines, in some embodiments, such lines can be created using one of the emerging genome editing technologies, such as the CRISPR-Cas9 system (reviewed in Ran et al. 2013). In fact, in some embodiments, this might be preferable to using pre-existing lines, as insertion sites can be specifically created in locations deemed optimal in terms of minimizing effects on local gene expression.

Many of the fragments used here, including the Opie2 (SEQ ID NO: 34 and SEQ ID NO: 35) promoter and fluorescent markers, are directly transferable to *Aedes aegypti*, for example).

In some embodiments, insertion sites must be chosen carefully, the various components (promoters, introns, etc.) must be tested empirically to make sure they function properly, and extensive crossing and screening must be done to isolate translocation individuals, since many vector species do not have balancer chromosomes to simplify crossing schemes. However, if the appropriate components are generated, it should be possible to build transgenic translocation-bearing vector populations capable of driving genes of interest into wild populations.

It is to be understood that the disclosures are not limited to particular compositions or biological systems, which can, of course, vary. It is also to be understood that the terminology used herein is for the purpose of describing particular embodiments only, and is not intended to be limiting. As used in this specification, the singular forms "a," "an," and "the" include plural referents unless the content clearly dictates otherwise. Unless defined otherwise, all technical and scientific terms used herein have the same meaning as commonly understood by one of ordinary skill in the art to which the disclosure pertains. Any methods and materials similar or equivalent to those described herein can be used in the practice for testing of the specific examples of appropriate materials and methods are described herein. A number of embodiments of the disclosure have been described. Nevertheless, it will be understood that various modifications may be made without departing from the spirit and scope of the present disclosure. Accordingly, other embodiments are within the scope of the following disclosure.

BIBLIOGRAPHY

All references cited in this disclosure are incorporated by reference to the same extent as if each reference had been incorporated by reference in its entirety individually. The entire disclosure of each document cited (including patents, patent applications, journal articles, abstracts, laboratory manuals, books, or other disclosures) is hereby incorporated herein by reference, Akbari, O. S., Chen, C. H., Marshall, J. M., Huang, H., Antoshechkin, and Hay, B. A. (2014). Novel synthetic Medea selfish genetic elements drive population replacement in *Drosophila*; a theoretical exploration of Medea-dependent population suppression. ACS synthetic biology 3, 915-928.

Akbari, O. S., Matzen, K. D., Marshall, J. M., Huang, H., Ward, C. M., and Hay, B. A. (2013). A synthetic gene drive system for local, reversible modification and suppression of insect populations. Current biology: CB 23, 671-677.

Altrock, P. M., Traulsen, A., and Reed, F. A. (2011). Stability properties of underdominance in finite subdivided populations. PLoS computational biology 7, e1002260, Altrock, P. M., Traulsen, A., Reeves, R. G., and Reed, F. A. (2010). Using underdominance to bistably transform local populations. Journal of theoretical biology 267, 62-75.

Asman, S. M., McDonald, P. T., and Prout, T. (1981). Field studies of genetic control systems for mosquitoes. Annual review of entomology 26, 289-318.

Baker, R. H. (1984). Chromosome Rearrangements in the Control of Mosquitos. Prev Vet Med 2, 529-540.

Beumer, Pimpinelli, S., and Golic, K. G. (1998). Induced chromosomal exchange directs the segregation of recombinant chromatids in mitosis of *Drosophila*. Genetics 150, 173-188.

Bier, V. M. G. a. E. (2015). The mutagenic chain reaction: A method for converting heterozygous to homozygous mutations. Science.

Chen, C. H., Huang, H., Ward, C. M., Su, J. T., Schaeffer, L. V., Guo, M., and Hay, B. A. (2007). A synthetic maternal-effect selfish genetic element drives population replacement in *Drosophila*. Science 316, 597-600.

Curtis, C. F. (1968). Possible use of translocations to fix desirable genes in insect pest populations. Nature 218, 368-369.

Davis, S., Bax, N., and Grewe, P. (2001). Engineered underdominance allows efficient and economical introgression of traits into pest populations. Journal of theoretical biology 212, 83-98.

de La Rocque, S., Balenghien, T., Halos, L., Dietze, K., Claes, F., Ferrari, G., Guberti, V., and Slingenbergh, J. (2011). A review of trends in the distribution of vector-borne diseases: is international trade contributing to their spread? Revue scientifique et technique 30, 119-130.

Deredec, A., Burt, A., and Godfray, H. C. (2008). The population genetics of using homing endonuclease genes in vector and pest management. Genetics 179, 2013-2026.

Egli, D., Hafen, E., and Schaffner, W. (2004). An efficient method to generate chromosomal rearrangements by targeted DNA double-strand breaks in *Drosophila melanogaster*. Genome research 14, 1382-1393.

Esvelt, K. M., Smidler, A. L., Catteruccia, F., and Church, G. M. (2014). Concerning RNA-guided gene drives for the alteration of wild populations. eLife, e03401.

Forster, A., Pannell, R., Drynan, L., Cano, F., Chan, N., Codrington, R., Daser, A., Lobato, N., Metzler, M., Nam, C. H., et al. (2005). Chromosomal translocation engineering to recapitulate primary events of human cancer. Cold Spring Harbor symposia on quantitative biology 70, 275-282.

Gibson, D. G., Young, L., Chuang, R. Y., Venter, J. C., Hutchison, C. A., 3rd, and Smith, H. O. (2009). Enzymatic assembly of DNA molecules up to several hundred kilobases. Nature methods 6, 343-345, Gould, F., and Schliekelman, P. (2004). Population genetics of autocidal control and strain replacement. Annual review of entomology 49, 193-217.

Gutierrez, E., Wiggins, D., Fielding, B., and Gould, A. P. (2007). Specialized hepatocyte-like cells regulate *Drosophila* lipid metabolism. Nature 445, 275-280.

Hay, B. A., Chen, C. H., Ward, C. M., Huang, H., Su, J. T., and Guo, M. (2010). Engineering the genomes of wild insect populations: challenges, and opportunities provided by synthetic Medea selfish genetic elements. Journal of insect physiology 56, 1402-1413.

Jansen, V. A., Turelli, M., and Godfray, H. C. (2008). Stochastic spread of *Wolbachia*. Proceedings Biological sciences/The Royal Society 275, 2769-2776, Kaiser, P. E., Seawright, J. A., Benedict, M. Q., Narang, S., and Suguna, S. G. (1982). Radiation induced reciprocal translocations and inversions in *Anopheles albimanus*. Canadian journal of genetics and cytology Journal canadien de genetique et de cytologic 24, 177-188.

Knots, B. G., Bossin, H. C., Mukabana, W. R., and Robinson, A. S. (2007), Transgenic mosquitoes and the fight against malaria: managing technology push in a turbulent GMO world. The American journal of tropical medicine and hygiene 77, 232-242.

Krafsur, E. S. (1998). Sterile insect technique for suppressing and eradicating insect populations: 55 years and counting. J Agr Entomol 15, 303-317.

Kyrchanova, O., Chetverina, D., Maksimenko, O., Kullyev, A., and Georgiev, P. (2008). Orientation-dependent interaction between *Drosophila* insulators is a property of this class of regulatory elements. Nucleic acids research 36, 7019-7028.

Lambrechts, L., Koella, J. C., and Boete, C. (2008), Can transgenic mosquitoes afford the fitness cost? Trends in parasitology 24, 4-7.

Magori, K., and Gould, F. (2006). Genetically engineered underdominance for manipulation of pest populations: a deterministic model. Genetics 172, 2613-2620.

Marshall, J. M. (2009). The effect of gene drive on containment of transgenic mosquitoes. Journal of theoretical biology 258, 250-265.

Marshall, J. M. (2010). The Cartagena Protocol and genetically modified mosquitoes. Nature biotechnology 28, 896-897.

Marshall, J. M., and Hay, B. A. (2012a). Confinement of gene drive systems to local populations: a comparative analysis. Journal of theoretical biology 294, 153-171.

Marshall, J. M., and Hay, B. A. (2012b). General principles of single-construct chromosomal gene drive. Evolution; international journal of organic evolution 66, 2150-2166.

Marshall, J. M., Pittman, G. W., Buchman, A. B., and Hay, B. A. (2011). Semele: a killer-male, rescue-female system for suppression and replacement of insect disease vector populations. Genetics 187, 535-551.

Nicholson, G. M. (2007). Fighting the global pest problem: preface to the special Toxicon issue on insecticidal toxins and their potential for insect pest control. Toxicon official journal of the International Society on Toxinology 49, 413-422.

Oye, K. A., Esvelt, K., Appleton, E., Catteruccia, F., Church, G., Kuiken, T., Lightfoot, S. B., McNamara, J., Smidler, A., and Collins, J. P. (2014), Biotechnology. Regulating gene drives. Science 345, 626-628.

Randolph, S. E., and Rogers, D. J. (2010). The arrival, establishment and spread of exotic diseases: patterns and predictions. Nature reviews Microbiology 8, 361-371.

Robinson, A. S., and Curtis, C. F. (1973). Controlled Crosses and Cage Experiments with a Translocation in *Drosophila*. Genetica 44, 591-601.

Rong, Y. S., and Golic, K. G. (2003). The homologous chromosome is an effective template for the repair of mitotic DNA double-strand breaks in *Drosophila*. Genetics 165, 1831-1842, Schmid-Hempel, P. (2005), Evolutionary ecology of insect immune defenses. Annual review of entomology 50, 529-551.

Sherizen, D., Jang, J. K., Bhagat, R., Kato, N., and McKim, K. S. (2005), Meiotic recombination in *Drosophila* females depends on chromosome continuity between genetically defined boundaries, Genetics 169, 767-781.

Sinkins, S T., and Gould, F. (2006). Gene drive systems for insect disease vectors. Nature reviews Genetics 7, 427-435.

Tatem, A. J., Rogers, D. J., and Hay, S. I. (2006), Global transport networks and infectious disease spread. Advances in parasitology 62, 293-343.

Theilmann, D. A., and Stewart, S. (1992). Molecular analysis of the trans-activating IE-2 gene of *Orgyia pseudotsugata* multicapsid nuclear polyhedrosis virus, Virology 187, 84-96.

Tripet, F., Aboagye-Antwi, F., and Hurd, H. (2008). Ecological immunology of mosquito-malaria interactions, Trends in parasitology 24, 219-227.

Uemura, M., Niwa, Y., Kakazu, N., Adachi, N., and Kinoshita, K. (2010).

Chromosomal manipulation by site-specific recombinases and fluorescent protein-based vectors. PloS one 5, e9846.

Willis, N. L., Seawright, J. A., Nickel, C., and Joslyn, D. J. (1981). Reciprocal translocations and partial correlation of chromosomes in the stable fly. The Journal of heredity 72, 104-106.

Windbichler, N., Menichelli, M., Papathanos, P. A., Thyme, S. B., Li, H., Ulge, U. Y., Hovde, B. T., Baker, D., Monnat, R. J., Jr., Burt, A., et al. (2011). A synthetic homing endonuclease-based gene drive system in the human malaria mosquito. Nature 473, 212-215.

Yu, Y., and Bradley, A. (2001). Engineering chromosomal rearrangements in mice. Nature reviews Genetics 2, 780-790.

Akbari, O. S., Matzen, K. D., Marshall, J. M., Huang, H., Ward, C. M., & Hay, B. A. (2013). A synthetic gene drive system for local, reversible modification and suppression of insect populations. Current Biology, 23(8), 671-77.

Alphey, L., Beard, C. B., Billingsley, P., et al. (2002), Malaria Control with Genetically Manipulated Insect. Nature, 415, 702.

Altrock, P. M., Traulsen, A., Reeves, R. G., & Reed, F. A. (2010). Using underdominance to bi-stably transform local populations. J Theor Biol, 267(1), 62-75, Altrock, P. M., Traulsen, A., & Reed, F. A. (2011). Stability properties of underdominance in finite subdivided populations. PLoS Comput Biol, 7(11), e1002260.

Arndt, K. M., MuEller, K. M., & PluEckthun, A. (2001). Helix-stabilized Fv (hsFv) antibody fragments: substituting the constant domains of a Fab fragment for a heterodimeric coiled-coil domain. Journal of molecular biology, 312(1), 221-228.

Asman, S. M., McDonald, P. T., & Prout, T. (1981). Field studies of genetic control systems for mosquitoes. Annual Review of Entomology, 26(1), 289-318, Baker, R. H. (1984). Chromosome rearrangements in the control of mosquitoes. Preventive Veterinary Medicine, 2(1), 529-540.

Bergmann, A., Agapite, J., McCall, K., & Steller, H. (1998). The *Drosophila* gene hid is a direct molecular target of Ras-dependent survival signaling. Cell, 95(3), 331-341.

Beumer, K. J., Pimpinelli, S., & Golic, K. G. (1998). Induced chromosomal exchange directs the segregation of recombinant chromatids in mitosis of *Drosophila*. Genetics, 150(1), 173-188.

Billeter, J. C., Atallah, J., Krupp, J. J., Millar, J. G., & Levine, J. D. (2009). Specialized cells tag sexual and species identity in *Drosophila melanogaster*. Nature, 461 (7266), 987-991.

Boete, C., & Koella, J. C. (2002). A theoretical approach to predicting the success of genetic manipulation of malaria mosquitoes in malaria control. Malar J, 1, 3.

Boete, C., & Koella, J. C. (2003). Evolutionary ideas about genetically manipulated mosquitoes and malaria control. Trends Parasitol, 19(1), 32-38.

Bohannon, J. (2002). Zambia rejects GM corn on scientists' advice. Science, 298(5596): 1153-1154.

Borycz, J., Borycz, J. A., Kubow, A., Lloyd, V., & Meinertzhagen, I. A. (2008). *Drosophila* ABC transporter mutants white, brown and scarlet have altered contents and distribution of biogenic amines in the brain. Journal of Experimental Biology, 211(21), 3454-3466.

Braig, H. R., & Yan, G. (2001). The spread of genetic constructs in natural insect populations. In D. K. Letourneau & B. E. Burrows (Eds.) Genetically Engineered Organisms: Assessing Environmental and Human Health Effects (pp. 251-314). Cleveland, Ohio/Boca Raton, Fla.: CRC Press.

Carvajal-Vallejos, P., Pallisse, R., Mootz, H. D., & Schmidt, S. R. (2012). Unprecedented rates and efficiencies revealed for new natural split inteins from metagenomic sources. J Biol Chem, 287(34), 28686-28696.

Carvalho, D. O., Costa-da-Silva, A. L., Lees, R. S., & Capurro, M. L. (2013). Two step male release strategy using transgenic mosquito lines to control transmission of vector-borne diseases. Acta Tropica 132S, S170-S177.

Centers for Disease Control and Prevention (2014). About malaria. Retrieved Apr. 30, 2014, from cdc.gov/malaria/about/facts.html.

Centers for Disease Control and Prevention (2012). Dengue fact sheet. Retrieved Apr. 30, 2014, from cdc.gov/Dengue/faqFacts/fact.html.

Chen, C. H., Huang, H., Ward, C. M., Su, J. T., Schaeffer, L. V., Guo, M., & Hay, B. A. (2007). A synthetic maternal-effect selfish genetic element drives population replacement in *Drosophila*. Science, 316(5824), 597-600.

Cheriyan, M., Pedamallu, C. S., Tori, K., & Perler, F. (2013). Faster protein splicing with the *Nostoc punctiforme* DnaE intein using non-native extein residues. Journal of Biological Chemistry, 288(9), 6202-6211.

Cook, R. K., Christensen, S. J., Deal, J. A., Coburn, R. A., Deal, M. E., Gresens, J. M., Cook, K. R. (2012). The generation of chromosomal deletions to provide extensive coverage and subdivision of the *Drosophila melanogaster* genome. Genome Biol, 13(3), R21.

Corby-Harris, V., Drexler, A., Watkins. de Jong, L., et al. (2010). Activation of Akt signaling reduces the prevalence and intensity of malaria parasite infection and lifespan in *Anopheles stephensi* mosquitoes. PLoS Pathog, 6(7), e1001003.

Crompton, P. D., Moebius, J., Portugal, S., Waisberg, M., Hart, G., Garver, L. S., . . . & Pierce, S. K. (2014). Malaria immunity in man and mosquito: insights into unsolved mysteries of a deadly infectious disease. *Annual Review of Immunology,* 32(1), 157-187.

Curtis, C. F. (1968), Possible use of translocations to fix desirable genes in insect pest populations. *Nature,* 218 (5139), 368-369.

Curtis C. F., & Robinson, A. S. (1971). Computer simulation of the use of double translocations for pest control. *Genetics* (69), 97-113.

Dantuma, N. P., Lindsten, K., Glas, R., Jellne, M., & Masucci, M. G. (2000). Short-lived green fluorescent proteins for quantifying ubiquitin/proteasome-dependent proteolysis in living cells. *Nature biotechnology,* 18(5), 538-543.

Davis, S., Bax, N., & Grewe, P. (2001). Engineered underdominance allows efficient and economical introgression of traits into pest populations. *J Theor Biol,* 212(1), 83-98.

De, N., Young, L., Lau, P. W., Meisner, N. C., Morrissey, D. V., & MacRae, I. J. (2013). Highly complementary target RNAs promote release of guide RNAs from human Argonaute2. *Molecular cell,* 50(3), 344-355.

de Jesus, C., & Rego, T. M. (2013), Use of genetic modified mosquitoes to fight dengue in Brazil. *International Journal of Research in Pharmaceutical and Nano Sciences.* 2(6), 811-816.

de Lara Capurro, M., Coleman, J., Beerntsen, B. T., et al. (2000). Virus-expressed, recombinant single-chain antibody blocks sporozoite infection of salivary glands in *Plasmodium gallinaceum*-infected *Aedes aegypti. Am J Trop Med Hyg,* 62(4), 427-433.

Deredec, A., Burt, A., & Godfray, H. C. J. (2008). The population genetics of using homing endonuclease genes in vector and pest management. *Genetics,* 179(4), 2013-2026.

Dhar, T., & Mootz, H. D. (2011). Modification of transmembrane and GPI-anchored proteins on living cells by efficient protein trans-splicing using the Npu DnaE intein. *Chem Commun* (Camb), 47(11), 3063-3065.

Egli, D., Hafen, E., & Schaffner, W. (2004). An efficient method to generate chromosomal rearrangements by targeted DNA double-strand breaks in *Drosophila melanogaster. Genome research,* 14(7), 1382-1393.

Engler, C., Kandzia, R., & Marillonnet, S. (2008). A one pot, one step, precision cloning method with high throughput capability. *PLoS one,* 3(11), e3647.

Engler, C., Gruetzner, R., Kandzia, R., & Marillonnet, S. (2009). Golden gate shuffling: a one-pot DNA shuffling method based on type IIs restriction enzymes. *PLoS one,* 4(5), e5553.

Enayati, A., & Hemingway, J. (2010). Malaria management: past, present, and future. *Annual review of entomology,* 55, 569-591.

Eppstein, M. J., Payne, J. L., & Goodnight, C. J. (2009). Underdominance, multiscale interactions, and self-organizing barriers to gene flow. *Journal of Artificial Evolution and Applications* 5, 1-13.

Fields, S., & Song, O. (1989). A novel genetic system to detect protein-protein interactions. *Nature,* 340(6230), 245-246, Filipowicz, W., Jaskiewicz, L., Kolb, F. A., & Pillai, R. S. (2005). Post-transcriptional gene silencing by siRNAs and miRNAs. *Current opinion in structural biology,* 15(3), 331-341.

Foster, G. G., Whitten, M. J., Prout, T., & Gill, R. (1972). Chromosome rearrangements for the control of insect pests. *Science,* 176(4037), 875-880.

Franz, A. W., Sanchez-Vargas, I., Adelman, Z. N., Blair, C. D., Beaty, B. J., James, A. A., & Olson, K. E. (2006). Engineering RNA interference-based resistance to dengue virus type 2 in genetically modified *Aedes aegypti. Proc Natl Acad Sci USA,* 103(11), 4198-4203.

Fu, G., Lees, R, S., Nimmo, D., Aw, D., Jin, L., Gray, P., et al. (2010). Female-specific flightless phenotype for mosquito control. *Proceedings of the National Academy of Sciences,* 107(10), 4550-4554.

Gallup, J. L., & Sachs, J. D. (2001). The economic burden of malaria. *Am J Trop Med Hyg* 64(1-2 Suppl), 85-96.

Gdula, D. A., Gerasimova, T. I., & Corces, V. G. (1996). Genetic and molecular analysis of the gypsy chromatin insulator of *Drosophila. Proc Natl Acad Sci USA* 93(18), 9378-83.

Gibson, D. G., Young, L., Chuang, R, Y., Venter, J. C., Hutchison, C. A., & Smith, H. O. (2009). Enzymatic assembly of DNA molecules up to several hundred kilobases. *Nature methods,* 6(5), 343-345.

Githeko, A. K., Lindsay, S. W., Confalonieri, U. E., & Patz, J. A. (2000). Climate change and vector-borne diseases: a regional analysis. *Bulletin of the World Health Organization,* 78(9), 1136-1147.

Gong, W. J., & Golic, K. G. (2003). Ends-out, or replacement, gene targeting in *Drosophila. Proceedings of the National Academy of Sciences,* 100(5), 2556-2561.

Gould, F., & Schliekelman, P. (2004). Population genetics of autocidal control and strain replacement. *Annu Rev Entomol,* 49, 193-217.

Gould, F., Magori, K., & Huang, Y, (2006). Genetic strategies for controlling mosquitoborne diseases: engineered genes that block the transmission of malaria and dengue can hitch a ride on selfish DNA and spread into wild populations. *American scientist,* 238-246.

Gould, F., Huang, Y., Legros, M., & Lloyd, A. L. (2008). A Killer-Rescue system for selflimiting gene drive of antipathogen constructs. *Proceedings of the Royal Society B: Biological Sciences,* 275(1653), 2823-2829.

Groth, A. C., Fish, M., Nusse, R., & Calos, M. P. (2004), Construction of transgenic *Drosophila* by using the site-specific integrase from phage φC31. *Genetics,* 166(4), 1775-1782.

Gubler, D. J. (1998). Resurgent vector-borne diseases as a global health problem. *Emerging infectious diseases,* 4(3), 442.

Gubler, D. J., Reiter, P., Ebi, K. L., Yap, W., Nasci, R., & Patz, J, A. (2001). Climate variability and change in the United States: potential impacts on vector- and rodent-borne diseases, Environmental health perspectives, 109 (Suppl 2), 223.

Gutierrez, E., Wiggins, D., Fielding, B., & Gould, A. P. (2007). Specialized hepatocytelike cells regulate *Drosophila* lipid metabolism. *Nature,* 445(7125), 275-280.

Han, Z., & Olson, E. N. (2005). Hand is a direct target of Tinman and GATA factors during *Drosophila* cardiogenesis and hematopoiesis, *Development,* 132(15), 3525-3536.

Harris, A. F., Nimmo, D., McKemey, A, R., et al. (2011). Field performance of engineered male mosquitoes. *Nature biotechnology,* 29(11), 1034-1037.

Harris, A. F., McKemey, A. R., Nimmo, D., Curtis, Z., Black, I., Morgan, S. A., & Alphey, L. (2012). Successful suppression of a field mosquito population by sustained release of engineered male mosquitoes. *Nature biotechnology,* 30(9), 828-830.

Hard, D. L., & Clark, A. G. (1997). *Principles of Population Genetics.* Sunderland, Mass.: Sinauer Associates, Inc.

Hay, B. A., Chen, C. H., Ward, C. M., Huang, H., Su, J. T., & Guo, M, (2010). Engineering the genomes of wild insect populations: challenges, and opportunities provided by synthetic Medea selfish genetic elements. *J Insect Physiol*, 56(10), 1402-1413.

Hoffmann, A. A., Montgomery, B. L., Popovici, J., et al. (2011). Successful establishment of *Wolbachia* in *Aedes* populations to suppress dengue transmission. *Nature*, 476(7361), 454-457.

Ito, J., Ghosh, A., Moreira, L, A., Wimmer, E. A., & Jacobs-Lorena, M. (2002), Transgenic anopheline mosquitoes impaired in transmission of a malaria parasite, *Nature*, 417(6887), 452-455.

Jacobs-Lorena, M. (2004). Genetic approached for malaria control. In Bogers, R. J. (ed.), *Bridging Laboratory and Field Research for Genetic Control of Disease Vectors* (pp. 52-65). Retrieved from library.wur.nl/frontis/.

James, A. A, (2005). Gene drive systems in mosquitoes: rules of the road. *Trends Parasitol*, 21(2), 64-67.

Kim, W., Koo, H., Richman, A. M., Seeley, D., Vizioli, J., Klocko, A. D., & O'Brochta, D. A. (2004). Ectopic expression of a cecropin transgene in the human malaria vector mosquito *Anopheles gambiae* (Diptera: Culicidae): effects on susceptibility to Plasmodium. *Journal of medical entomology*, 41(3), 447-455.

Knols, B. G., Bossin, H. C., Mukabana, W. R., & Robinson, A. S. (2007). Transgenic mosquitoes and the fight against malaria: managing technology push in a turbulent GMO world. *Am J Trop Med Hyg*. 77(6 Suppl), 232-42.

Krafsur, E. S. (1998). Sterile insect technique for suppressing and eradicating insect populations: 55 years and counting. *J. Agric. Entomol*, 15, 303-317.

Krstic, D., Boll, W., & Noll, M. (2013). Influence of the White Locus on the Courtship Behavior of *Drosophila* Males. *PLoS one*, 8(10), e77904.

Kwit, C., Moon, H. S., Warwick, S. I., & Stewart, C. N., Jr. (2011). Transgene introgression in crop relatives: molecular evidence and mitigation strategies. *Trends Biotechnol*, 29(6), 284-293.

Kyrchanova, O., Chetverina, D., Maksimenko, O., Kullyev, A., & Georgiev, P. (2008). Orientation-dependent interaction between *Drosophila* insulators is a property of this class of regulatory elements. *Nucleic acids research*, 36(22), 7019-7028.

Lemon, S. M., Sparling, P. F., Hamburg, M. A., Reiman, D. A., Choffnes, E. R., & Mack, A. (2008). Vector-Borne Diseases: Understanding the Environmental, Human Health, and Ecological Connections, Workshop Summary (Forum on Microbial Threats). National Academies Press.

Lin, H., McGrath, J., Wang, P., & Lee, T. (2007). Cellular toxicity induced by SRFmediated transcriptional squelching. *Toxicological sciences*, 96(1), 83-91.

Lo, P. C., & Frasch, M. (2001). A role for the COUP-TF-related gene seven-up in the diversification of cardioblast identities in the dorsal vessel of *Drosophila*. *Mech Dev*, 104(1-2), 49-60.

Lockless, S. W., & Muir, T. W. (2009). Traceless protein splicing utilizing evolved split inteins. *Proc Natl Acad Sci USA*, 106(27), 10999-11004.

Luan, H., Peabody, N. C., Vinson, C. R., & White, B. H. (2006). Refined spatial manipulation of neuronal function by combinatorial restriction of transgene expression. *Neuron*, 52(3), 425-436.

Lyon, M. F., Phillips, R. J., & Bailey, H, J. (1972). Mutagenic effects of repeated small radiation doses to mouse spermatogonia I. Specific-locus mutation rates. *Mutation Research/Fundamental and Molecular Mechanisms of Mutagenesis*, 15(2), 185-190.

Magori, K., & Gould, F. (2006). Genetically engineered underdominance for manipulation of pest populations: a deterministic model. *Genetics*, 172(4), 2613-2620.

Marris, E. (2010). Transgenic fish go large. *Nature*, 467 (7313), 259.

Marshall, J. M. (2009). The effect of gene drive on containment of transgenic mosquitoes. *Journal of theoretical biology*, 258(2), 250-265.

Marshall, J. M. (2010). The Cartagena Protocol and genetically modified mosquitoes. *Nature biotechnology*, 28(9), 896-897.

Marshall, J. M., & Hay, B. A. (2011). Inverse Medea as a novel gene drive system for local population replacement: a theoretical analysis. *J Hered*, 102(3), 336-341.

Marshall, J. M., & Hay, B. A. (2012). Confinement of gene drive systems to local populations: a comparative analysis. *J Theor Biol*, 294, 153-171.

Marshall, J. M., Touré, M. B., Traore, M. M., Famenini, S., & Taylor, C. E. (2010a), Perspectives of people in *Mali* toward genetically-modified mosquitoes for malaria control. *Malar J*, 9, 128.

Marshall, J. M., Touré, M. B., Traore, M. M., & Taylor, C. E. (2010b). Towards a quantitative assessment of public attitudes to transgenic mosquitoes: Questions based on a qualitative survey in Mali. *Asia Pacific J Mol. Biol, Biotechnol*, 18, 251-273.

Marygold, S. J., Roote, J., Reuter, G., et al. (2007). The ribosomal protein genes and Minute loci of *Drosophila melanogaster*. *Genome Biol*, 8(10), R216, Matzen, K. J. (2012). Engineering of Dengue virus refractoriness in *Aedes aegypti* and development of an underdominant gene drive system (Doctoral dissertation). California Institute of Technology, Pasadena, Calif.

McManus, M. T., Petersen, C. P., Haines, B. B., Chen, J., & Sharp, P. A. (2002). Gene silencing using micro-RNA designed hairpins. RNA, 8(6), 842-850.

Miller, T. A. (2011). Let high-tech genetically modified insects counter dengue. *BioScience*, 61(8), 586-587.

Miller, L. H., & Pierce, S. K. (2009). Perspective on malaria eradication: is eradication possible without modifying the mosquito? *Journal of Infectious Diseases*, 200(11), 1644-1645.

Moreira, L. A., Ito, J., Ghosh, A., Devenport, M., Zieler, H., Abraham, E. G., . . . Jacobs-Lorena, M. (2002). Bee venom phospholipase inhibits malaria parasite development in transgenic mosquitoes. *J Biol Chem*, 277(43), 40839-40843.

Moreno, E. (2012). Design and construction of "synthetic species". *PLoS One*, 7(7), e39054.

Morrison, N. I., Franz, G., Koukidou, M., et al. (2010). Genetic improvements to the sterile insect technique for agricultural pests. *Asia-Pacific Journal of Molecular Biology and Biotechnology*, 18(2), 275-295.

Mumford, J. D, (2012). Science, regulation, and precedent for genetically modified insects. *PLoS neglected tropical diseases*, 6(1), e1504.

Murray, C. J., Rosenfeld, L. C., Lim, S. S., et al. (2012). Global malaria mortality between 1980 and 2010: a systematic analysis. *The Lancet*, 379(9814), 413-431.

Nath, R. (2003). Generation and characterisation of plant produced recombinant antibodies specific to LHRH for treatment of sex hormone dependent diseases. (MS thesis). Fachhochschule Aachen, Aachen, Germany.

Ndiath, M. O., Sougoufara, S., Gaye, A., et al. (2012). Resistance to DDT and pyrethroids and increased kdr mutation frequency in *An. gambiae* after the implementation of permethrin-treated nets in Senegal. *PloS one,* 7(2), e31943.

Neely, G. G., Kuba, K., Cammarato, A., et al, (2010). A Global In Vivo *Drosophila* RNAi Screen Identifies NOT3 as a Conserved Regulator of Heart Function. *Cell,* 141(1), 142-153.

Nern, A., Pfeiffer, B. D., Svoboda, K., & Rubin, G. M. (2011). Multiple new site-specific recombinases for use in manipulating animal genomes. Proceedings of the National Academy of Sciences, 108(34), 14198-14203.

Ni, J. Q., Zhou, R., Czech, B., et al. (2011). A genome-scale shRNA resource for transgenic RNAi in *Drosophila. Nat Methods,* 8(5), 405-407.

Pardo, R., Engelhard, M., Hagen, K., et al. (2009). The role of means and goals in technology acceptance. A differentiated landscape of public perceptions of pharming. *EMBO Rep,* 10(10), 1069-1075.

Parvy, J. P., Napal, L., Rubin, T., Poidevin, M., Perrin, L., Wicker-Thomas, C., & Montagne, J. (2012). *Drosophila melanogaster* Acetyl-CoA-Carboxylase Sustains a Fatty Acid-Dependent Remote Signal to Waterproof the Respiratory System. *PLoS genetics,* 8(8), el 002925.

Perrimon, N., Ni, J. Q., & Perkins, L. (2010). In vivo RNAi: today and tomorrow. *Cold Spring Harbor perspectives in biology,* 2(8), a003640.

Pfeiffer, B. D., Ngo, T. T. B., Hibbard, K. L., Murphy, C., Jenett, A., Truman, J. W., & Rubin, G. M. (2010). Refinement of tools for targeted gene expression in *Drosophila. Genetics,* 186(2), 735-755.

Pfeiffer, B. D., Truman, J. W., & Rubin, G. M. (2012). Using translational enhancers to increase transgene expression in *Drosophila. Proc Natl Acad Sci USA,* 109(17), 6626-6631.

Ran, F. A., Hsu, P. D., Wright, J., Agarwala, V., Scott, D. A., & Zhang, F. (2013). Genome engineering using the CRISPR-Cas9 system. *Nature protocols,* 8(11), 2281-2308.

Riehle, M. M., Xu, J., Lazzaro, B. P., et al. (2008). *Anopheles gambiae* APL1 is a family of variable LRR proteins required for Rel1-mediated protection from the malaria parasite, *Plasmodium berghei. PLoS One,* 3(11), e3672.

Ringrose, L., Chabanis, S., Angrand, P. O., Woodroofe, C., & Stewart, A. F. (1999). Quantitative comparison of DNA looping in vitro and in vivo: chromatin increases effective DNA flexibility at short distances. *The EMBO Journal,* 18(23), 6630-6641.

Robinson A. S. (1975). A reassessment of the use of chromosome inversions for insect control. *Journal of Heredity* (66):35-37.

Robinson, A. S. (1976). Progress in the use of chromosomal translocations for the control of insect pests. *Biological Reviews,* 51(1), 1-24.

Robinson, A, S., Franz, G., & Atkinson, P. W. (2004). Insect transgenesis and its potential role in agriculture and human health, *Insect biochemistry and molecular biology,* 34(2), 113-120.

Rong, Y. S., & Golic, K. G. (2003). The homologous chromosome is an effective template for the repair of mitotic DNA double-strand breaks in *Drosophila. Genetics,* 165(4), 1831-1842.

Rørth, P. (1998). Ga14 in the *Drosophila* female germline. *Mechanisms of development,* 78(1), 113-118.

Serebrovskii, A. S. (1940). On the possibility of a new method for the control of insect pests. *Zool. Zh.* 19:618-90.

Schmid-Hempel, P. (2005). Evolutionary ecology of insect immune defenses. *Annu Rev Entomol,* 50, 529-551.

Schnutgen, F., & Ghyselinck, N. B. (2007). Adopting the good reFLEXes when generating conditional alterations in the mouse genome. *Transgenic research,* 16(4), 405-413.

Schwartz, E, C., Saez, L., Young, M. W., & Muir, T. W. (2007). Post-translational enzyme activation in an animal via optimized conditional protein splicing. *Nat Chem Biol,* 3(1), 50-54.

Sellin, J., Albrecht, S., Kolsch, V., & Paululat, A. (2006). Dynamics of heart differentiation, visualized utilizing heart enhancer elements of the *Drosophila melanogaster* bHLH transcription factor Hand. *Gene Expr Patterns,* 6(4), 360-375.

Sherizen, D., Jang, J. K., Bhagat, R., Kato, N., & McKim, K, S. (2005). Meiotic recombination in *Drosophila* females depends on chromosome continuity between genetically defined boundaries. *Genetics,* 169(2), 767-781.

Sinkins, S. P., & Gould, F. (2006). Gene drive systems for insect disease vectors. *Nat Rev Genet,* 7(6), 427-435.

Spradling, A. C., & Rubin, G. M. (1982). Transposition of cloned P elements into *Drosophila* germ line chromosomes. *Science,* 218(4570), 341-347.

Szymczak, A. L., Workman, C. J., Wang, Y., Vignali, K. M., Dilioglou, S., Vanin, E. F., & Vignali, D. A. (2004). Correction of multi-gene deficiency in vivo using a single 'self-cleaving' 2A peptide-based retroviral vector. Nature biotechnology, 22(5), 589-594.

Theilmann, D. A., & Stewart, S. (1992). Molecular analysis of the trans-activating IE-2 gene of *Orgyia pseudotsugata* multicapsid nuclear polyhedrosis virus. *Virology* 187(1), 84-96.

Thomas, D. D., Donnelly, C. A., Wood, R. J., & Alphey, L. S. (2000). Insect population control using a dominant, repressible, lethal genetic system. *Science,* 287(5462), 2474-2476.

Thorpe, H. M., Wilson, S. E., & Smith, M. (2000). Control of directionality in the sitespecific recombination system of the *Streptomyces* phage φC31. *Molecular microbiology,* 38(2), 232-241.

Tolle, M. A. (2009), Mosquito-borne diseases. *Current problems in pediatric and adolescent health care,* 39(4), 97-140.

Uemura, M., Niwa, Y., Kakazu, N., Adachi, N., & Kinoshita, K. (2010). Chromosomal manipulation by site-specific recombinases and fluorescent protein-based vectors. *PLoS one,* 5(3), e9846.

Van Dyke, D. L., Weiss, L., Roberson, J. R., & Babu, V. R. (1983). The frequency and mutation rate of balanced autosomal rearrangements in man estimated from prenatal genetic studies for advanced maternal age. *American journal of human genetics,* 35(2), 301.

Walker, T., Johnson, P. H., Moreira, L. A., et al. (2011). The wMel *Wolbachia* strain blocks dengue and invades caged *Aedes aegypti* populations. *Nature,* 476(7361), 450-453.

Wang, S., & Jacobs-Lorena, M. (2013). Genetic approaches to interfere with malaria transmission by vector mosquitoes. *Trends in biotechnology,* 31(3), 185-193.

Weber, E., Engler, C., Gruetzner, R., Werner, S., & Marillonnet, S. (2011). A modular cloning system for standardized assembly of multigene constructs. *PLoS one,* 6(2), e16765.

Whitten, M. J. (1971). Insect control by genetic manipulation of natural populations. *Science,* 171(3972), 682-684.

Windbichler, N., Menichelli, M., Papathanos, P. A., et al. (2011). A synthetic homing endonuclease-based gene drive system in the human malaria mosquito. *Nature*, 473(7346), 212-215.

World Health Organization (2000). Global Burden of Disease Study. Retrieved Apr. 30, 2014, from who.int/evidence/bod.

World Health Organization (2014a). Malaria factsheet, Retrieved Apr. 30, 2014, from who.int/mediacentre/factsheets/fs094/en/index.html World Health Organization (2014b). Dengue factsheet. Retrieved Apr. 30, 2014, from who.int/mediacentre/factsheets/fs117/en/index.html Yu, Y., & Bradley, A. (2001). Engineering chromosomal rearrangements in mice, *Nature Reviews Genetics*, 2(10), 780-790.

Zettler, J., Schutz, V., & Mootz, H. D. (2009). The naturally split Npu DnaE intein exhibits an extraordinarily high rate in the protein trans-splicing reaction. *FEBS Lett*, 583(5), 909-914.

Zhou, X., Vink, M., Klaver, B., Berkhout, B., & Das, A. T. (2006). Optimization of the Tet-On system for regulated gene expression through viral evolution. *Gene therapy*, 13(19), 1382-1390.

Zhu, X. D., & Sadowski, P. D. (1995). Cleavage-dependent ligation by the FLP recombinase; characterization of a mutant flp protein with an alteration in a catalytic amino acid, *Journal of Biological Chemistry*, 270(39), 23044-23054.

---

What is claimed is:

1. A translocation mediated gene drive system, the gene drive system comprising:

a first construct, configured to be positionable at a first insertion site in a first chromosome, wherein the first construct comprises:
   a) a first location to insert a first gene of interest;
   b) a first promoter;
   c) a first fragment of foreign stuffer DNA;
   d) a second fragment of foreign stuffer DNA;
   e) a first target site of a pair of target sites for an endonuclease positioned between the first and second fragments of foreign stuffer DNA;
   f) a first splice acceptor site, positioned downstream from a-e; and
   g) a first splice donor site, positioned between b and c, and a second construct, configured to be positionable at a second insertion site in a second chromosome, wherein the second construct comprises:
   h) a second location to insert a second gene of interest;
   i) a second promoter;

j) a third fragment of foreign stuffer DNA, wherein the third fragment is homologous to the second fragment;
k) a fourth fragment of foreign stuffer DNA, wherein the fourth fragment is homologous to the first fragment;
l) a second target site of the pair of target sites for an endonuclease positioned between the third and fourth fragments of foreign stuffer DNA;
m) a second splice acceptor site, positioned downstream from h-l, and
n) a second splice donor site, positioned between i and j, wherein the first and second chromosomes are non-homologous chromosomes,
wherein the first fragment of foreign stuffer DNA is homologous to the fourth fragment of foreign stuffer DNA and the second fragment of foreign stuffer DNA is homologous to the third fragment of foreign stuffer DNA,
wherein a double stranded break created at the first, and second target sites of the pair of target sites allows for homologous recombination between the first and fourth fragments, and between the second and third fragments upon a repair of the double stranded break (DSB),
wherein the repair of the DSB induces a chromosomal translocation and generates a first translocation chromosome and a second translocation chromosome.

2. The system of claim 1, wherein the size of the first fragment of foreign stuffer DNA is about 50 bp to about 10 kb.

3. The system of claim 1, wherein the size of the second fragment of foreign stuffer DNA is about 50 bp to about 10 kb.

4. The system of claim 1, wherein the size of the third fragment of foreign stuffer DNA is about 50 bp to about 10 kb.

5. The system of claim 1, wherein the size of the fourth fragment of foreign stuffer DNA is about 50 bp to about 10 kb.

6. The system of claim 1, wherein the first insertion site and second insertion site comprise an insertion site combination.

7. The system of claim 1, wherein an insertion site is located at least 500 bp from a gene.

8. The system of claim 1, wherein the first and second constructs inserted in the first and second insertion sites, respectively are oriented in the same direction with respect to the centromere of the first and second chromosomes.

9. The system of claim 1, wherein the construct is transferable to a mosquito.

10. The system of claim 1, wherein the system is self-perpetuating or self-propagating or both when present at a high frequency.

11. The system of claim 1, wherein the gene drive system is configured to be spread in a first population comprising wildtype individuals comprising non-translocation-bearing chromosomes that do not carry the gene drive system to obtain a second population comprising a high frequency of translocation-bearing individuals that carry the gene drive system, and wherein the gene drive system can be eliminated from the second population by introducing a high frequency of the wildtype individuals.

12. The system of claim 1, wherein creation of a translocation can occur through the repair of the DSB by a non-homologous end joining of broken DNA ends instead of by homologous recombination.

* * * * *

SEQUENCE LISTING

```
<160> NUMBER OF SEQ ID NOS: 75

<210> SEQ ID NO 1
<211> LENGTH: 63
<212> TYPE: DNA
<213> ORGANISM: Artificial
<220> FEATURE:
<223> OTHER INFORMATION: Synthetic; P1

<400> SEQUENCE: 1
cctaacaact cacaccttgc agcgccacct ggccctagag atccaccaac tttttttgcac    60 tgc                                                                   63

<210> SEQ ID NO 2
<211> LENGTH: 60
<212> TYPE: DNA
<213> ORGANISM: Artificial
<220> FEATURE:
<223> OTHER INFORMATION: Synthetic; P2

<400> SEQUENCE: 2
attcctaagc atcagtggtt gaacctacct tgttggcgtg accagagaca ggttgcggcg    60

<210> SEQ ID NO 3
<211> LENGTH: 50
<212> TYPE: DNA
<213> ORGANISM: Artificial
<220> FEATURE:
<223> OTHER INFORMATION: Synthetic; P3

<400> SEQUENCE: 3
aggttcaacc actgatgctt aggaataggc catgtgaagc tgaaggaatc                50

<210> SEQ ID NO 4
<211> LENGTH: 64
<212> TYPE: DNA
<213> ORGANISM: Artificial
<220> FEATURE:
<223> OTHER INFORMATION: Synthetic; P4

<400> SEQUENCE: 4
tattaccctg ttatccctac tagtagggat aacagggtaa tactagaatc cctgggcaca    60
attt                                                                  64

<210> SEQ ID NO 5
<211> LENGTH: 64
<212> TYPE: DNA
<213> ORGANISM: Artificial
```

<220> FEATURE:
<223> OTHER INFORMATION: Synthetic; P5

<400> SEQUENCE: 5
ctagtattac cctgttatcc ctactagtag ggataacagg gtaatagtgg ttgtaagcct    60
tgca                                                                64

<210> SEQ ID NO 6
<211> LENGTH: 60
<212> TYPE: DNA
<213> ORGANISM: Artificial
<220> FEATURE:
<223> OTHER INFORMATION: Synthetic; P6

<400> SEQUENCE: 6
aaaggataag aatttagggtt agtcgtttcg gtgtgcctag tttaccagga gagtgggaga    60

<210> SEQ ID NO 7
<211> LENGTH: 60
<212> TYPE: DNA
<213> ORGANISM: Artificial
<220> FEATURE:
<223> OTHER INFORMATION: Synthetic; P7

<400> SEQUENCE: 7
cgcccacgcc atccaaccgc cgccgcaacc tgtctctggt cacgccaaca aggtaggttc    60

<210> SEQ ID NO 8
<211> LENGTH: 60
<212> TYPE: DNA
<213> ORGANISM: Artificial
<220> FEATURE:
<223> OTHER INFORMATION: Synthetic; P8

<400> SEQUENCE: 8
atgacgttct tggaggagcg caccattttg ttgctaaagg aaaggataag aatttagggtt    60

<210> SEQ ID NO 9
<211> LENGTH: 60
<212> TYPE: DNA
<213> ORGANISM: Artificial
<220> FEATURE:
<223> OTHER INFORMATION: Synthetic; P9

<400> SEQUENCE: 9
aaacgactaa ccctaattct tatcctttcc tttagcaaca aaatggtgcg ctcctccaag    60

<210> SEQ ID NO 10
<211> LENGTH: 60
<212> TYPE: DNA
<213> ORGANISM: Artificial
<220> FEATURE:
<223> OTHER INFORMATION: Synthetic; P10

<400> SEQUENCE: 10
aatggaactc ttcgcggcca ggtggcgctg caaggctcga gggtcgactg atcataatca    60

<210> SEQ ID NO 11
<211> LENGTH: 60
<212> TYPE: DNA
<213> ORGANISM: Artificial
<220> FEATURE:
<223> OTHER INFORMATION: Synthetic; P11

<400> SEQUENCE: 11
ggatccggga attgggaatt gggcaatatt taaatggcgg ccttgcagcg ccacctggcc    60

<210> SEQ ID NO 12
<211> LENGTH: 60
<212> TYPE: DNA
<213> ORGANISM: Artificial
<220> FEATURE:
<223> OTHER INFORMATION: Synthetic; P12

<400> SEQUENCE: 12
agcgtgtttt tttgcagtgc aaaaaagttg gtggatctct agggccaggt ggcgctgcaa    60

<210> SEQ ID NO 13
<211> LENGTH: 60
<212> TYPE: DNA
<213> ORGANISM: Artificial
<220> FEATURE:
<223> OTHER INFORMATION: Synthetic; P13

<400> SEQUENCE: 13
tacaaatgtg gtatggctga ttatgatcag tcgaccctcg agccttgcag cgccacctgg    60

<210> SEQ ID NO 14
<211> LENGTH: 60
<212> TYPE: DNA
<213> ORGANISM: Artificial
<220> FEATURE:
<223> OTHER INFORMATION: Synthetic; P14

<400> SEQUENCE: 14
gagaccgtga cctacatcgt cgacactagt ggatctctag ggccaggtgg cgctgcaagg    60

<210> SEQ ID NO 15
<211> LENGTH: 60
<212> TYPE: DNA
<213> ORGANISM: Artificial
<220> FEATURE:
<223> OTHER INFORMATION: Synthetic; P15

<400> SEQUENCE: 15
ccaacgcatt ttccaagctt gtttaaacgt ggatctctag ggccaggtgg cgctgcaagg    60

<210> SEQ ID NO 16
<211> LENGTH: 60
<212> TYPE: DNA
<213> ORGANISM: Artificial
<220> FEATURE:
<223> OTHER INFORMATION: Synthetic; P16

<400> SEQUENCE: 16
ccttgcagcg ccacctggcc ctagagatcc acgtttaaac aagcttggaa aatgcgttgg    60

<210> SEQ ID NO 17
<211> LENGTH: 60
<212> TYPE: DNA
<213> ORGANISM: Artificial
<220> FEATURE:
<223> OTHER INFORMATION: Synthetic; P17

<400> SEQUENCE: 17
cgaagcgcct ctatttatac tccggcgctc gtttaaacaa agtggcaggg cccatgtgtt    60

<210> SEQ ID NO 18
<211> LENGTH: 60
<212> TYPE: DNA
<213> ORGANISM: Artificial

```
<220> FEATURE:
<223> OTHER INFORMATION: Synthetic; P18

<400> SEQUENCE: 18
gagtggagca caaacacatg ggccctgcca ctttgtttaa acgagcgccg gagtataaat      60

<210> SEQ ID NO 19
<211> LENGTH: 60
<212> TYPE: DNA
<213> ORGANISM: Artificial
<220> FEATURE:
<223> OTHER INFORMATION: Synthetic; P19

<400> SEQUENCE: 19
aagcatcagt ggttgaacct accttgttgg cgtgtctgat gcagattgtt tagcttgttc      60

<210> SEQ ID NO 20
<211> LENGTH: 60
<212> TYPE: DNA
<213> ORGANISM: Artificial
<220> FEATURE:
<223> OTHER INFORMATION: Synthetic; P20

<400> SEQUENCE: 20
gccaacaagg taggttcaac cactgatgct taggaatagg cgtggttgta agccttgcat      60

<210> SEQ ID NO 21
<211> LENGTH: 60
<212> TYPE: DNA
<213> ORGANISM: Artificial
<220> FEATURE:
<223> OTHER INFORMATION: Synthetic; P21

<400> SEQUENCE: 21
ccctgttatc cctactagta gggataacag ggtaatacta gtttaccagg agagtgggag      60

<210> SEQ ID NO 22
<211> LENGTH: 60
<212> TYPE: DNA
<213> ORGANISM: Artificial
<220> FEATURE:
<223> OTHER INFORMATION: Synthetic; P22

<400> SEQUENCE: 22
tattaccctg ttatccctac tagtagggat aacagggtaa tacatgtgaa gctgaaggaa      60

<210> SEQ ID NO 23
<211> LENGTH: 60
<212> TYPE: DNA
<213> ORGANISM: Artificial
<220> FEATURE:
<223> OTHER INFORMATION: Synthetic; P23

<400> SEQUENCE: 23
aaaggataag aattagggtt agtcgtttcg gtgtgcctag aatccctggg cacaattttc      60

<210> SEQ ID NO 24
<211> LENGTH: 60
<212> TYPE: DNA
<213> ORGANISM: Artificial
<220> FEATURE:
<223> OTHER INFORMATION: Synthetic; P24

<400> SEQUENCE: 24
caagcgcagc tgaacaagct aaacaatctg catcagacac gccaacaagg taggttcaac      60
```

```
<210> SEQ ID NO 25
<211> LENGTH: 62
<212> TYPE: DNA
<213> ORGANISM: Artificial
<220> FEATURE:
<223> OTHER INFORMATION: Synthetic; P25

<400> SEQUENCE: 25
acctacatcg tcgacactag tggatctcta gctcgagcta aaggaaagga taagaattag      60
gg                                                                    62

<210> SEQ ID NO 26
<211> LENGTH: 60
<212> TYPE: DNA
<213> ORGANISM: Artificial
<220> FEATURE:
<223> OTHER INFORMATION: Synthetic; P26

<400> SEQUENCE: 26
ccctaattct tatcctttcc tttaggaatt ccaacaaaat ggtgagcaag ggcgaggagc      60

<210> SEQ ID NO 27
<211> LENGTH: 60
<212> TYPE: DNA
<213> ORGANISM: Artificial
<220> FEATURE:
<223> OTHER INFORMATION: Synthetic; P27

<400> SEQUENCE: 27
ttcactgcat tctagttgtg gtttgtccaa actcatcaat gtttacttgt acagctcgtc      60

<210> SEQ ID NO 28
<211> LENGTH: 60
<212> TYPE: DNA
<213> ORGANISM: Artificial
<220> FEATURE:
<223> OTHER INFORMATION: Synthetic; P28

<400> SEQUENCE: 28
gccgccggga tcactctcgg catggacgag ctgtacaagt aaacattgat gagtttggac      60

<210> SEQ ID NO 29
<211> LENGTH: 18
<212> TYPE: DNA
<213> ORGANISM: Artificial
<220> FEATURE:
<223> OTHER INFORMATION: Syntehtic; I-SceI site

<400> SEQUENCE: 29
attaccctgt tatcccta                                                   18

<210> SEQ ID NO 30
<211> LENGTH: 74
<212> TYPE: DNA
<213> ORGANISM: Artificial
<220> FEATURE:
<223> OTHER INFORMATION: Synthetic; Rpl35a Intron 5'

<400> SEQUENCE: 30
ccatcctcaa ggtatgtcta tacttcaatg tgatgggtcc ggacttcaca gagttttca      60 aataataatt aata                                                       74

<210> SEQ ID NO 31
<211> LENGTH: 71
```

-continued

```
<212> TYPE: DNA
<213> ORGANISM: Artificial
<220> FEATURE:
<223> OTHER INFORMATION: Synthetic; Rpl35a Intron 3'

<400> SEQUENCE: 31
cattccagtt ctgtaaaaac attttagtaa tgtaattgat taaccaacat attacattgc    60
agattgaggg c                                                        71

<210> SEQ ID NO 32
<211> LENGTH: 43
<212> TYPE: DNA
<213> ORGANISM: Artificial
<220> FEATURE:
<223> OTHER INFORMATION: Synthetic; MHC16 Intron 5'

<400> SEQUENCE: 32
cacgccaaca aggtaggttc aaccactgat gcttaggaat agg                     43

<210> SEQ ID NO 33
<211> LENGTH: 47
<212> TYPE: DNA
<213> ORGANISM: Artificial
<220> FEATURE:
<223> OTHER INFORMATION: Synthetic; MHC16 Intron 3'

<400> SEQUENCE: 33
ctaggcacac cgaaacgact aaccctaatt cttatccttt cctttag                 47

<210> SEQ ID NO 34
<211> LENGTH: 30
<212> TYPE: DNA
<213> ORGANISM: Artificial
<220> FEATURE:
<223> OTHER INFORMATION: Synthetic; Opie2 5'end

<400> SEQUENCE: 34
caccaacttt tttgcactgc aaaaaaacac                                    30

<210> SEQ ID NO 35
<211> LENGTH: 30
<212> TYPE: DNA
<213> ORGANISM: Artificial
<220> FEATURE:
<223> OTHER INFORMATION: Synthetic; Opie2 3'end

<400> SEQUENCE: 35
atccaaccgc cgccgcaacc tgtctctggt                                    30

<210> SEQ ID NO 36
<211> LENGTH: 30
<212> TYPE: DNA
<213> ORGANISM: Artificial
<220> FEATURE:
<223> OTHER INFORMATION: Synthetic; SVP 5'end

<400> SEQUENCE: 36
aagcttggaa aatgcgttgg agtaatagcc                                    30

<210> SEQ ID NO 37
<211> LENGTH: 30
<212> TYPE: DNA
<213> ORGANISM: Artificial
<220> FEATURE:
<223> OTHER INFORMATION: Synthetic; SVP 3'end
```

-continued

<400> SEQUENCE: 37
ggagcacaaa cacatgggcc ctgccacttt                30

<210> SEQ ID NO 38
<211> LENGTH: 30
<212> TYPE: DNA
<213> ORGANISM: Artificial
<220> FEATURE:
<223> OTHER INFORMATION: Synthetic; Hsp70 basal 5'end

<400> SEQUENCE: 38
agcgccggag tataaataga ggcgcttcgt                30

<210> SEQ ID NO 39
<211> LENGTH: 30
<212> TYPE: DNA
<213> ORGANISM: Artificial
<220> FEATURE:
<223> OTHER INFORMATION: Synthetic; Hsp70 basal 3'end

<400> SEQUENCE: 39
aagcgcagct gaacaagcta aacaatctgc                30

<210> SEQ ID NO 40
<211> LENGTH: 30
<212> TYPE: DNA
<213> ORGANISM: Artificial
<220> FEATURE:
<223> OTHER INFORMATION: Synthetic; Actin5 5'end

<400> SEQUENCE: 40
taaaaaaaat catgaatggc atcaactctg                30

<210> SEQ ID NO 41
<211> LENGTH: 30
<212> TYPE: DNA
<213> ORGANISM: Artificial
<220> FEATURE:
<223> OTHER INFORMATION: Synthetic; Actin5 3'end

<400> SEQUENCE: 41
catcagccag cagtcgtcta atccagagac                30

<210> SEQ ID NO 42
<211> LENGTH: 30
<212> TYPE: DNA
<213> ORGANISM: Artificial
<220> FEATURE:
<223> OTHER INFORMATION: Synthetic; XYZ 5'end

<400> SEQUENCE: 42
catgtgaagc tgaaggaatc tggccctggg                30

<210> SEQ ID NO 43
<211> LENGTH: 30
<212> TYPE: DNA
<213> ORGANISM: Artificial
<220> FEATURE:
<223> OTHER INFORMATION: Synthetic; XYZ 3'end

<400> SEQUENCE: 43
aggtggacaa gaaaattgtg cccagggatt                30

<210> SEQ ID NO 44
<211> LENGTH: 30

```
<212> TYPE: DNA
<213> ORGANISM: Artificial
<220> FEATURE:
<223> OTHER INFORMATION: Synthetic; UVW 5'end

<400> SEQUENCE: 44
gtggttgtaa gccttgcata tgtacagtcc                                30

<210> SEQ ID NO 45
<211> LENGTH: 30
<212> TYPE: DNA
<213> ORGANISM: Artificial
<220> FEATURE:
<223> OTHER INFORMATION: Synthetic; UVW 3'end

<400> SEQUENCE: 45
gagaagagcc tctcccactc tcctggtaaa                                30

<210> SEQ ID NO 46
<211> LENGTH: 30
<212> TYPE: DNA
<213> ORGANISM: Artificial
<220> FEATURE:
<223> OTHER INFORMATION: Synthetic; GFP 5'end

<400> SEQUENCE: 46
atggtgagca agggcgagga gctgttcacc                                30

<210> SEQ ID NO 47
<211> LENGTH: 30
<212> TYPE: DNA
<213> ORGANISM: Artificial
<220> FEATURE:
<223> OTHER INFORMATION: Synthetic; GFP 3'end

<400> SEQUENCE: 47
actctcggca tggacgagct gtacaagtaa                                30

<210> SEQ ID NO 48
<211> LENGTH: 30
<212> TYPE: DNA
<213> ORGANISM: Artificial
<220> FEATURE:
<223> OTHER INFORMATION: Synthetic; dsRed 5'end

<400> SEQUENCE: 48
atggtgcgct cctccaagaa cgtcatcaag                                30

<210> SEQ ID NO 49
<211> LENGTH: 30
<212> TYPE: DNA
<213> ORGANISM: Artificial
<220> FEATURE:
<223> OTHER INFORMATION: Synthetic; dsRed 3'end

<400> SEQUENCE: 49
ctacaggaac aggtggtggc ggccctcggt                                30

<210> SEQ ID NO 50
<211> LENGTH: 30
<212> TYPE: DNA
<213> ORGANISM: Artificial
<220> FEATURE:
<223> OTHER INFORMATION: Synthetic; SV40 3'UTR 5'end

<400> SEQUENCE: 50
```
acattgatga gtttggacaa accacaacta                                           30

<210> SEQ ID NO 51
<211> LENGTH: 30
<212> TYPE: DNA
<213> ORGANISM: Artificial
<220> FEATURE:
<223> OTHER INFORMATION: Synthetic; SV40 3'UTR 3'end

<400> SEQUENCE: 51
tgtggtatgg ctgattatga tcagtcgacc                                           30

<210> SEQ ID NO 52
<211> LENGTH: 30
<212> TYPE: DNA
<213> ORGANISM: Artificial
<220> FEATURE:
<223> OTHER INFORMATION: Synthetic; CTCF 5'end

<400> SEQUENCE: 52
ccttgcagcg ccacctggcc gcgaagagtt                                           30

<210> SEQ ID NO 53
<211> LENGTH: 30
<212> TYPE: DNA
<213> ORGANISM: Artificial
<220> FEATURE:
<223> OTHER INFORMATION: Synthetic; CTCF 3'end

<400> SEQUENCE: 53
ggccaggtgg cgctgcaagg tgtgagttgt                                           30

<210> SEQ ID NO 54
<211> LENGTH: 26
<212> TYPE: DNA
<213> ORGANISM: Artificial
<220> FEATURE:
<223> OTHER INFORMATION: Synthetic; attP1-F

<400> SEQUENCE: 54
agagtcgtcg acgtcaaaat caccac                                               26

<210> SEQ ID NO 55
<211> LENGTH: 24
<212> TYPE: DNA
<213> ORGANISM: Artificial
<220> FEATURE:
<223> OTHER INFORMATION: Synthetic; attP1-R

<400> SEQUENCE: 55
gcatacatta tacgaagtta tgag                                                 24

<210> SEQ ID NO 56
<211> LENGTH: 26
<212> TYPE: DNA
<213> ORGANISM: Artificial
<220> FEATURE:
<223> OTHER INFORMATION: Synthetic; attP2-F

<400> SEQUENCE: 56
aggttacccc agttggggca ctactc                                               26

<210> SEQ ID NO 57
<211> LENGTH: 28
<212> TYPE: DNA
<213> ORGANISM: Artificial

```
<220> FEATURE:
<223> OTHER INFORMATION: Synthetic; attP2-R

<400> SEQUENCE: 57
taacctttga gttctctcag ttgggggc                                        28

<210> SEQ ID NO 58
<211> LENGTH: 24
<212> TYPE: DNA
<213> ORGANISM: Artificial
<220> FEATURE:
<223> OTHER INFORMATION: Synthetic; 22A-F

<400> SEQUENCE: 58
aatggattcg tgctcatctt ctgg                                            24

<210> SEQ ID NO 59
<211> LENGTH: 25
<212> TYPE: DNA
<213> ORGANISM: Artificial
<220> FEATURE:
<223> OTHER INFORMATION: Synthetic; 22A-R

<400> SEQUENCE: 59
agtgaagtca aacttcttgt gagtc                                           25

<210> SEQ ID NO 60
<211> LENGTH: 24
<212> TYPE: DNA
<213> ORGANISM: Artificial
<220> FEATURE:
<223> OTHER INFORMATION: Synthetic; 51C-F

<400> SEQUENCE: 60
ctcgcaaatg ccagcagggt aatg                                            24

<210> SEQ ID NO 61
<211> LENGTH: 24
<212> TYPE: DNA
<213> ORGANISM: Artificial
<220> FEATURE:
<223> OTHER INFORMATION: Synthetic; 51C-R

<400> SEQUENCE: 61
tagcgaatga aaactgcgaa gaag                                            24

<210> SEQ ID NO 62
<211> LENGTH: 24
<212> TYPE: DNA
<213> ORGANISM: Artificial
<220> FEATURE:
<223> OTHER INFORMATION: Synthetic; 68E-F

<400> SEQUENCE: 62
caattacatt tcgattgatt ttca                                            24

<210> SEQ ID NO 63
<211> LENGTH: 25
<212> TYPE: DNA
<213> ORGANISM: Artificial
<220> FEATURE:
<223> OTHER INFORMATION: Synthetic; 688-R

<400> SEQUENCE: 63
gcaaacatga cgtatggaaa atatc                                           25
```

```
<210> SEQ ID NO 64
<211> LENGTH: 24
<212> TYPE: DNA
<213> ORGANISM: Artificial
<220> FEATURE:
<223> OTHER INFORMATION: Synthetic; 96E-F

<400> SEQUENCE: 64
ggtgccgtgt gtcaaatgtg tcgc                                        24

<210> SEQ ID NO 65
<211> LENGTH: 24
<212> TYPE: DNA
<213> ORGANISM: Artificial
<220> FEATURE:
<223> OTHER INFORMATION: Synthetic; 96E-R

<400> SEQUENCE: 65
gattaacgtg ctgcacggct cacg                                        24

<210> SEQ ID NO 66
<211> LENGTH: 27
<212> TYPE: DNA
<213> ORGANISM: Artificial
<220> FEATURE:
<223> OTHER INFORMATION: Synthetic; 9741-F

<400> SEQUENCE: 66 tactttttcgt aaaccatatt gagatac                                    27

<210> SEQ ID NO 67
<211> LENGTH: 28
<212> TYPE: DNA
<213> ORGANISM: Artificial
<220> FEATURE:
<223> OTHER INFORMATION: Synthetic; 9741-R

<400> SEQUENCE: 67
taaaatggac ctgtaggaat ttacttac                                    28

<210> SEQ ID NO 68
<211> LENGTH: 30
<212> TYPE: DNA
<213> ORGANISM: Artificial
<220> FEATURE:
<223> OTHER INFORMATION: Synthetic; Opie2-F

<400> SEQUENCE: 68 caccaactttt tttgcactgc aaaaaaacac                                 30

<210> SEQ ID NO 69
<211> LENGTH: 30
<212> TYPE: DNA
<213> ORGANISM: Artificial
<220> FEATURE:
<223> OTHER INFORMATION: Synthetic; GFP-R

<400> SEQUENCE: 69
actctcggca tggacgagct gtacaagtaa                                  30

<210> SEQ ID NO 70
<211> LENGTH: 25
<212> TYPE: DNA
<213> ORGANISM: Artificial
<220> FEATURE:
<223> OTHER INFORMATION: Synthetic; Hsp70-F
```

```
<400> SEQUENCE: 70
tcaaacaagc aaagtgaaca catcg                                           25

<210> SEQ ID NO 71
<211> LENGTH: 30
<212> TYPE: DNA
<213> ORGANISM: Artificial
<220> FEATURE:
<223> OTHER INFORMATION: Synthetic; dsRed-R

<400> SEQUENCE: 71
ctacaggaac aggtggtggc ggccctcggt                                      30

<210> SEQ ID NO 72
<211> LENGTH: 30
<212> TYPE: DNA
<213> ORGANISM: Artificial
<220> FEATURE:
<223> OTHER INFORMATION: Synthetic; SV40-F

<400> SEQUENCE: 72
acattgatga gtttggacaa accacaacta                                      30

<210> SEQ ID NO 73
<211> LENGTH: 7
<212> TYPE: DNA
<213> ORGANISM: Artificial
<220> FEATURE:
<223> OTHER INFORMATION: Synthetic; Kozak

<400> SEQUENCE: 73 caacaaa                                                                7

<210> SEQ ID NO 74
<211> LENGTH: 40
<212> TYPE: DNA
<213> ORGANISM: Artificial
<220> FEATURE:
<223> OTHER INFORMATION: Synthetic; Two 18bp I-SceI recognition
      sequences with linker

<400> SEQUENCE: 74
attaccctgt tatccctact agtagggata acagggtaat                           40

<210> SEQ ID NO 75
<211> LENGTH: 4
<212> TYPE: DNA
<213> ORGANISM: Artificial
<220> FEATURE:
<223> OTHER INFORMATION: Synthetic; Linker

<400> SEQUENCE: 75 ctag                                                                   4
```